(12) United States Patent
Bertinato et al.

(10) Patent No.: US 7,482,368 B2
(45) Date of Patent: *Jan. 27, 2009

(54) TRIAMIDE-SUBSTITUTED HETEROBICYCLIC COMPOUNDS

(75) Inventors: Peter Bertinato, Old Lyme, CT (US); Brian Bronk, Gales Ferry, CT (US); Alan E. Blize, New London, CT (US); Hengmiao Cheng, East Lyme, CT (US); Jin Li, Pawcatuck, CT (US); Hiep Huatan, Maidstone (GB); Clive Mason, Deal (GB)

(73) Assignee: Pfizer Inc, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/196,563

(22) Filed: Aug. 2, 2005

(65) Prior Publication Data

US 2005/0288335 A1  Dec. 29, 2005

Related U.S. Application Data

(62) Division of application No. 10/639,855, filed on Aug. 13, 2003, now Pat. No. 6,949,572, which is a division of application No. 10/177,858, filed on Jun. 20, 2002, now Pat. No. 6,720,351.

(60) Provisional application No. 60/301,644, filed on Jun. 28, 2001.

(51) Int. Cl.
A61K 31/44 (2006.01)

(52) U.S. Cl. ..................................................... 514/339

(58) Field of Classification Search ................ 514/415, 514/339; 548/492
See application file for complete search history.

(56) References Cited

U.S. PATENT DOCUMENTS

| | | | |
|---|---|---|---|
| 4,022,900 A | 5/1977 | Mathison ................... 424/258 |
| 4,397,855 A | 8/1983 | Sircar ....................... 424/250 |
| 5,416,009 A | 5/1995 | Lazzeri et al. ............. 435/69.3 |
| 5,712,279 A | 1/1998 | Biller et al. ................. 514/252 |
| 5,731,340 A | 3/1998 | Bras et al. .................. 514/415 |
| 5,741,804 A | 4/1998 | Keenan et al. .............. 514/394 |
| 5,919,795 A | 7/1999 | Chang et al. ............... 514/310 |
| 5,968,950 A | 10/1999 | Quallich et al. ............ 514/310 |
| 6,066,653 A | 5/2000 | Gregg et al. ............... 514/325 |
| 6,121,283 A | 9/2000 | Chang et al. ............... 514/307 |
| 6,197,798 B1 | 3/2001 | Fink et al. .................. 514/354 |
| 6,235,730 B1 | 5/2001 | Sato et al. ............. 514/211.11 |
| 6,281,228 B1 | 8/2001 | Tino ........................... 514/319 |
| 6,288,234 B1 | 9/2001 | Griffin ........................ 546/190 |
| 6,337,344 B1 * | 1/2002 | Defossa et al. ............. 514/415 |
| 6,720,351 B2 * | 4/2004 | Bertinato et al. ........... 514/415 |
| 6,818,644 B1 | 11/2004 | Lehmann-Lintz et al. ....................... 514/252.14 |
| 6,821,967 B2 | 11/2004 | Lehmann-Lintz et al. ... 514/218 |
| 6,979,692 B2 * | 12/2005 | Bertinato et al. ............ 514/339 |
| 2002/0032238 A1 | 3/2002 | Priepke et al. .............. 514/616 |
| 2003/0114442 A1 | 6/2003 | Heckel et al. ................ 514/218 |

FOREIGN PATENT DOCUMENTS

| | | |
|---|---|---|
| DE | 19945594 | 3/2001 |
| EP | 0643057 | 3/1995 |
| EP | 1006122 | 6/2000 |
| EP | 1080724 | 3/2001 |
| EP | 1099701 | 5/2001 |
| EP | 1181954 | 2/2002 |
| EP | 0584446 | 6/2002 |
| EP | 1479666 | 11/2004 |
| WO | WO 9727979 | 8/1997 |
| WO | WO9743257 | 11/1997 |
| WO | WO0005201 | 2/2000 |
| WO | WO0076971 | 12/2000 |
| WO | WO0105762 | 1/2001 |
| WO | WO121604 | 3/2001 |
| WO | WO0147898 | 7/2001 |
| WO | WO0147899 | 7/2001 |
| WO | WO0153260 | 7/2001 |
| WO | WO0177077 | 10/2001 |
| WO | WO0192241 | 12/2001 |
| WO | WO0196327 | 12/2001 |

(Continued)

OTHER PUBLICATIONS

Jundong Zhang, et al., Bioorganic & Medicinal Chemistry, "Identification of Inhibitors of Heparin-growth factor interactions from Combinatorial Libraries of Four-Component Condensation Reaction", (2001), vol. 9 No. 4, p. 825-836.

Watterau, J.R., et al., Biochimica et Biophysica Acta, "Localization of Intracellular Triacylglycerol and Cholesteryl Ester Transfer Activity in Rat Tissues", vol. 875 pp. 610-617 (1986).

(Continued)

Primary Examiner—Rei-tsang Shiao
(74) Attorney, Agent, or Firm—Paul M. Misiak; Robert M. Kennedy; Martha A. Gammill

(57) ABSTRACT

The invention relates to triamide MTP/ApoB inhibitors of the formula 1

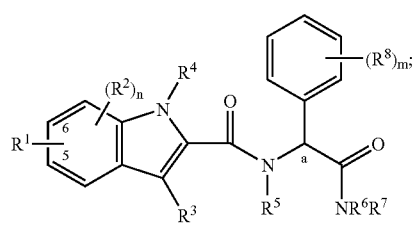

wherein $R^1$-$R^8$ are as defined in the specification, as well as pharmaceutical compositions and uses thereof, and processes for preparing the compounds. The compounds of the invention are useful for the treatment of obesity and lipid disorders.

2 Claims, 6 Drawing Sheets

FOREIGN PATENT DOCUMENTS

| | | |
|---|---|---|
| WO | WO0197810 | 12/2001 |
| WO | WO0204403 | 1/2002 |
| WO | WO0242291 | 5/2002 |
| WO | WO0283658 | 10/2002 |

OTHER PUBLICATIONS

Watterau, J.R., et al., *Science*, "Absence of Microsomal Triglyceride Transfer Protein in Individuals with Abetalipoproteinemia", vol. 258, (Nov. 6, 1992).

* cited by examiner

TRIAMIDE-SUBSTITUTED HETEROBICYCLIC COMPOUNDS

This application is a divisional of U.S. patent application Ser. No. 10/639,855 filed on Aug. 13, 2003, now U.S. Pat. No. 6,949,572 which is a divisional of U.S. patent application Ser. No. 10/177,858 filed on Jun. 20, 2002, now U.S. Pat. No. 6,720,351 which issued on Apr. 13, 2004 and which claims the benefit of U.S. Provisional Patent Application No. 60/301,644 filed on Jun. 28, 2001, all three of which are incorporated herein by reference in their entirety.

FIELD OF THE INVENTION

This invention relates to triamide-substituted heterobicyclic compounds. These compounds are inhibitors of microsomal triglyceride transfer protein (MTP) and/or apolipoprotein B (Apo B) secretion and are useful for the treatment of obesity and related diseases. These compounds are also useful for the prevention and treatment of atherosclerosis and its clinical sequelae, for lowering serum lipids, and in the prevention and treatment of related diseases. The invention further relates to pharmaceutical compositions comprising these compounds and to methods of treating obesity, atherosclerosis, and related diseases and/or conditions with said compounds, either alone or in combination with other medicaments, including lipid lowering agents. Further still, the invention relates to certain processes and intermediates related thereto which are useful in the preparation of the compounds of the instant invention.

BACKGROUND OF THE INVENTION

Microsomal triglyceride transfer protein catalyzes the transport of triglyceride, cholesteryl ester, and phospholipids and has been implicated as a putative mediator in the assembly of Apo B-containing lipoproteins, biomolecules which contribute to the formation of atherosclerotic lesions. Specifically, the subcellular (lumen of the microsomal fraction) and tissue distribution (liver and intestine) of MTP have led to speculation that it plays a role in the assembly of plasma lipoproteins, as these are the sites of plasma lipoprotein assembly. The ability of MTP to catalyze the transport of triglyceride between membranes is consistent with this speculation, and suggests that MTP may catalyze the transport of triglyceride from its site of synthesis in the endoplasmic reticulum membrane to nascent lipoprotein particles within the lumen of the endoplasmic reticulum.

Accordingly, compounds which inhibit MTP and/or otherwise inhibit Apo B secretion are useful in the treatment of atherosclerosis and other conditions related thereto. Such compounds are also useful in the treatment of other diseases or conditions in which, by inhibiting MTP and/or Apo B secretion, serum cholesterol and triglyceride levels may be reduced. Such conditions may include, for example, hypercholesterolemia, hypertriglyceridemia, pancreatitis, and obesity; and hypercholesterolemia, hypertriglyceridemia, and hyperlipidemia associated with pancreatitis, obesity, and diabetes. For a detailed discussion, see for example, Wetterau et al., Science, 258, 999-1001, (1992), Wetterau et al., Biochem. Biophys. Acta., 875, 610-617 (1986), European patent application publication Nos. 0 584 446 A2, and 0 643 057 A1, the latter of which refers to certain compounds which have utility as inhibitors of MTP. Other examples of MTP inhibitors may be found in e.g., U.S. Pat. Nos. 5,712,279, 5,741,804, 5,968,950, 6,066,653, and 6,121,283; PCT International Patent Application publications WO 96/40640, WO 97/43257, WO 98/27979, WO 99/33800 and WO 00/05201; and European patent application publications EP 584446 and EP 643,057.

SUMMARY OF THE INVENTION

The present invention relates to compounds of the formula 1:

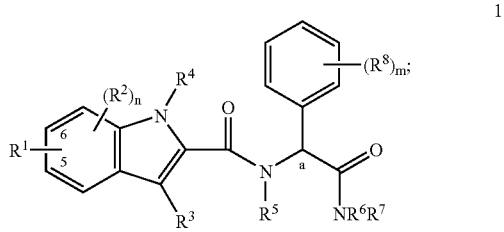

or a pharmaceutically acceptable salt thereof, wherein:

$R^1$ is substituted at the 5 or 6 position of formula 1 and has the structure:

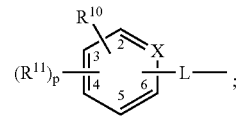

m is an integer from 0 to 5;
n is an integer from 0 to 3;
p is an integer from 0 to 3;
L is —C(O)N($R^9$)—, i.e., L has the structure:

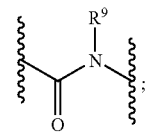

X is N or C($R^c$);
$R^2$, $R^8$, $R^{11}$, $R^{12}$, $R^{13}$ and $R^{16}$ are each independently selected from halo, cyano, nitro, azido, amino, hydroxy, ($C_1$-$C_6$)alkyl, ($C_2$-$C_6$)alkoxy, methoxy, ($C_1$-$C_6$)alkoxy($C_1$-$C_6$)alkyl, mono-, di- or tri-halo($C_2$-$C_6$)alkyl, perfluoro($C_2$-$C_4$)alkyl, trifluoromethyl, trifluoromethyl($C_1$-$C_5$)alkyl, mono-, di- or tri-halo($C_2$-$C_6$)alkoxy, trifluoromethyl($C_1$-$C_5$)alkoxy, ($C_1$-$C_6$)alkylthio, hydroxy($C_1$-$C_6$)alkyl, ($C_3$-$C_8$)cycloalkyl ($CR^aR^b)_q$—, ($C_2$-$C_6$)alkenyl, ($C_2$-$C_6$)alkynyl, ($C_1$-$C_6$)alkylamino-, ($C_1$-$C_6$)dialkylamino, amino($C_1$-$C_6$)alkyl-, —($CR^aR^b)_qNR^aR^{14}$, —C(O)$NR^aR^{14}$, —$NR^{14}$C(O)$R^{15}$, —$NR^{14}$O$R^{15}$, —CH=NO$R^{15}$, —$NR^{14}$C(O)O$R^{15}$, —$NR^{14}$S(O)$_jR^{15}$, —C(O)$R^{15}$, —C(S)$R^{15}$, —C(O)O$R^{15}$, —OC(O)$R^{15}$, —SO$_2NR^aR^{14}$, —S(O)$_jR^{15}$, or —($CR^aR^b)_qS(O)_jR^{15}$;
each $R^a$ and $R^b$ is independently H or ($C_1$-$C_6$)alkyl;
$R^c$ is H or $R^{11}$;
each q is independently an integer from 0 to 6;
each j is independently 0, 1 or 2;
$R^3$ is H, halo, ($C_1$-$C_6$)alkyl, or mono-, di- or tri-halo($C_1$-$C_6$)alkyl;
$R^4$ is H, ($C_1$-$C_6$)alkyl, ($C_3$-$C_8$)cycloalkyl, —C(O)$R^{15}$, —C(S)$R^{15}$, —($CR^aR^b)_rO(C_1$-$C_6$ alkyl), —($CR^aR^b)_rS(C_1$-$C_6$ alkyl), —($CR^aR^b)_rC(O)R^{15}$, —($CR^aR^b)R^{15}$, —SO$_2R^{15}$ or —(CR$^a$R$^b$)$_q$-phenyl, wherein the phenyl moiety is optionally substituted with from one to five independently selected R$^{16}$;

each r is independently an integer from 2 to 5;

each t is independently an integer from 1 to 6;

R$^5$, R$^6$ and R$^9$ are each independently H, (C$_1$-C$_6$)alkyl, (C$_3$-C$_8$)cycloalkyl, —C(O)R$^{15}$, —C(S)R$^{15}$, —(CR$^a$R$^b$)$_t$O (C$_1$-C$_6$ alkyl), —(CR$^a$R$^b$)$_t$S(C$_1$-C$_6$ alkyl), —(CR$^a$R$^b$)$_r$C(O) R$^{15}$, —(CR$^a$R$^b$)$_r$R$^{15}$ or —SO$_2$R$^{15}$;

R$^7$ is phenyl, pyridyl, phenyl-Z$^1$- or pyridyl-Z$^1$-, wherein the phenyl or pyridyl moiety is optionally substituted with one to five independently selected R$^{12}$;

Z$^1$ is —SO$_2$— or —(CR$^a$R$^b$)$_v$—;

v is independently an integer from 1 to 6;

R$^{10}$ is phenyl, pyridyl, phenyl-Z$^2$- or pyridyl-Z$^2$-, wherein the phenyl or pyridyl moiety is optionally substituted with one to five independently selected R$^{13}$;

Z$^2$ is —S(O)$_j$—, —O—, —(CR$^a$R$^b$)$_w$—, or —(O)$_k$(CR$^a$R$^b$)$_w$(O)$_k$(CR$^a$R$^b$)$_q$—;

w is independently an integer from 1 to 6;

each k is independently 0 or 1;

each R$^{14}$ is independently H, (C$_1$-C$_6$)alkyl, (C$_3$-C$_8$)cycloalkyl, —C(O)R$^{15}$, C(S)R$^{15}$, —(CR$^a$R$^b$)$_t$O(C$_1$-C$_6$ alkyl), —(CR$^a$R$^b$)$_t$S(C$_1$-C$_6$ alkyl), —(CR$^a$R$^b$)$_r$C(O)R$^{15}$, —(CR$^a$R$^b$)$_r$R$^{15}$ or —SO$_2$R$^{15}$;

each R$^{15}$ is independently H, (C$_1$-C$_6$)alkyl, (C$_3$-C$_8$)cycloalkyl, trifluoromethyl, trifluoromethyl(C$_1$-C$_5$)alkyl, wherein the alkyl, moieties of the foregoing R$^{15}$ groups are independently optionally substituted with 1 to 3 substituents independently selected from C$_1$-C$_6$ alkyl, C$_1$-C$_6$ alkoxy, amino, hydroxy, halo, cyano, nitro, trifluoromethyl and trifluoromethoxy;

and wherein any of the above "alkyl", "alkenyl" or "alkynyl" moieties comprising a CH$_3$ (methyl), CH$_2$ (methylene), or CH (methine) group which is not substituted with halogen, SO or SO$_2$, or attached to a N, O or S atom, optionally bears on said methyl, methylene or methine group a substituent selected from the group consisting of halo, —OR$^a$, —SR$^a$ and —NR$^a$R$^b$.

In an embodiment of the invention, L is attached to the 2 position of R$^1$ and to the 5 position of formula 1, i.e., the compound of formula 1 has the structure of formula 1a:

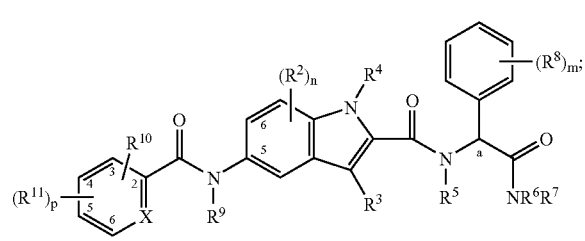

1a

In another embodiment of the invention, L is attached to the 2 position of R$^1$ and to the 5 position of formula 1, and R$^{10}$ is attached at the 3' position.

In another embodiment of the invention, L is attached to the 3 position of R$^1$ and to the 5 position formula 1. In another embodiment of the invention, L is attached to the 3 position of R$^1$ and to the 5 position of formula 1 and X is N. In still another embodiment of the invention, L is attached to the 3 position of R$^1$ and to the 5 position of formula 1, X is N and R$^{10}$ is attached at the 2 position of R$^1$. In other embodiments of the invention, the attachment of L to R$^1$ is selected from the 3, 4, 6 or 6 position and the attachment of L to the compound of formula 1 is selected from the 5 position or 6 position.

In another embodiment of the invention, X is C(R$^c$).

In another embodiment of the invention, X is C(R$^c$), m is 0, n is 0, and p is 0 or 1.

In another embodiment of the invention, X is C(R$^c$), m is 0, n is 0, and p is 0 or 1, and R$^{10}$ is phenyl-Z$^2$- attached at the 3 position of R$^1$, wherein the phenyl moiety of R$^{10}$ is optionally substituted with one to five independently selected R$^{13}$.

In another embodiment of the invention, X is C(R$^c$), m is 0, n is 0, and p is 0 or 1, and R$^{10}$ is phenyl attached at the 3 position of R$^1$, wherein the phenyl moiety of R$^{10}$ is optionally substituted with one to five independently selected R$^{13}$.

In another embodiment of the invention, R$^7$ is phenyl-Z$^1$, wherein the phenyl moiety is optionally substituted with one to five independently selected R$^{12}$. In a preferred embodiment of the invention, Z$^1$ is —(CR$^a$R$^b$)$_v$—, and in a more preferred embodiment, Z$^1$ is methylene, i.e., —CH$_2$—.

In another embodiment of the invention, R$^4$, R$^5$, R$^6$ and R$^9$ are each independently selected from H, (C$_1$-C$_6$)alkyl, —(CR$^a$R$^b$)$_q$O(C$_1$-C$_6$ alkyl) or —(CR$^a$R$^b$)$_r$R$^{15}$.

In another embodiment of the invention, each R$^{12}$ is independently selected from halo, hydroxy, (C$_1$-C$_6$)alkyl, methoxy, (C$_2$-C$_6$)alkoxy, (C$_1$-C$_6$)alkoxy(C$_1$-C$_6$)alkyl, mono-, di- or tri-halo(C$_2$-C$_6$)alkyl, trifluoromethyl, trifluoromethyl(C$_1$-C$_5$)alkyl, mono-, di- or tri-halo(C$_2$-C$_6$)alkoxy, trifluoromethyl(C$_1$-C$_5$)alkoxy, (C$_1$-C$_5$)alkylthio and hydroxy(C$_1$-C$_6$)alkyl.

In another embodiment of the invention, each R$^{13}$ is independently selected from halo, hydroxy, amino, cyano, (C$_1$-C$_6$)alkyl, (C$_2$-C$_6$)alkenyl, methoxy, (C$_2$-C$_6$)alkoxy, (C$_1$-C$_6$)alkoxy(C$_1$-C$_6$)alkyl, mono-, di- or tri-halo(C$_2$-C$_6$)alkyl, trifluoromethyl, trifluoromethyl(C$_1$-C$_5$)alkyl, mono-, di- or tri-halo(C$_2$-C$_6$)alkoxy, trifluoromethyl(C$_1$-C$_5$)alkoxy, (C$_1$-C$_6$)alkylthio, hydroxy(C$_1$-C$_6$)alkyl, —C(O)OR$^{15}$ and —NR$^{14}$C(O)R$^{15}$; wherein R$^{14}$ is H or (C$_1$-C$_6$)alkyl; and wherein R$^{15}$ is H or (C$_1$-C$_6$)alkyl.

In another embodiment of the invention, R$^{10}$ is phenyl attached at the 3 position of R$^1$, wherein the phenyl moiety of R$^{10}$ is optionally substituted with one R$^{13}$. In a preferred embodiment, R$^{10}$ and R$^1$ both are phenyl, such that R$^1$ and R$^{10}$ together form a 1,1'-biphenyl group, wherein R$^{10}$ comprises the 1'-6' positions of the biphenyl group and R$^{13}$ is substituted at the 4' position of the biphenyl.

In another embodiment of the invention, R$^4$ is H, (C$_1$-C$_6$)alkyl or —(CR$^a$R$^b$)$_q$O(C$_1$-C$_6$ alkyl).

In another embodiment of the invention, the carbon designated "a" in formula 1 is in the "(S)" configuration.

In a preferred embodiment of the invention, R$^{13}$ is trifluoromethyl.

In another preferred embodiment of the invention, R$^3$ is H, halo, or (C$_1$-C$_6$)alkyl.

In a more preferred embodiment of the invention, R$^6$ is methyl.

In a particularly preferred embodiment of the invention, the compound of formula 1 is (S)-1-ethyl-5-[(4'-trifluoromethyl-biphenyl-2-carbonyl)-amino]-1H-indole-2-carboxylic acid {2-[benzyl(methyl)amino]-2-oxo-1-phenylethyl} amide.

In another particularly preferred embodiment of the invention, the compound of formula 1 is (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide.

In another more preferred embodiment of the invention R$^3$ is chloro.

In another particularly preferred embodiment of the invention, the compound of formula 1 is selected from the group consisting of:

3-chloro-5-[(4'-trifluoromethyl-biphenyl-2-carbonyl)-amino]-1H-indole-2-carboxylic acid {2-[benzyl(methyl)amino]-2-oxo-1-phenylethyl}amide;

3-chloro-1-methyl-5-[(4'-trifluoromethyl-biphenyl-2-carbonyl)-amino]-1H-indole-2-carboxylic acid {2-[benzyl(methyl)amino]-2-oxo-1-phenylethyl}amide;

4'-trifluoromethyl-biphenyl-2-carboxylic acid [2-({[(benzyl-methylcarbamoyl)phenyl-methyl]-methyl-amino}methyl)-3-chloro-1-methyl-1H-indol-5-yl]-amide, which is alternately named: 3-chloro-1-methyl-5-[(4'-trifluoromethyl-biphenyl-2-carbonyl)amino]-1H-indole-2-carboxylic acid {N-[2-(benzyl(methyl)amino)-2-oxo-1-phenylethyl]methyl}amide;

3-chloro-1-methyl-5-[methyl-(4'-trifluoromethyl-biphenyl-2-carbonyl)-amino]-1H-indole-2-carboxylic acid {2-[benzyl(methyl)amino]-2-oxo-1-phenylethyl}amide; and 3-chloro-1-ethyl-5-[(4'-trifluoromethyl-biphenyl-2-carbonyl)-amino]-1H-indole-2-carboxylic acid {2-[benzyl(methyl)amino]-2-oxo-1-phenylethyl}amide.

In another embodiment of the invention, X is C($R^c$), m is 0, n is 0, and p is 0 or 1, and $R^{10}$ is phenyl-$Z^2$- attached at the 3'-position, wherein the phenyl moiety of $R^{10}$ is optionally substituted with one to five independently selected $R^{13}$ and $Z^2$ is O or S.

In another embodiment of the invention, $R^7$ is phenyl-$Z^1$, wherein the phenyl moiety is optionally substituted with one to five independently selected $R^{12}$ and $Z^1$ is O or S.

In another embodiment of the invention, $R^7$ is pyridyl-$Z^1$, wherein the pyridyl moiety is optionally substituted with from one to five independently selected $R^{12}$. In a preferred embodiment thereof, $Z^1$ is —($CH_2$)—.

In another embodiment of the invention, X is N and $R^{10}$ is phenyl optionally substituted with one to five independently selected $R^{13}$.

In another embodiment of the invention, X is N and $R^{10}$ is phenyl optionally substituted with one to five independently selected $R^{13}$, and $R^7$ is phenyl-$Z^1$, wherein the phenyl moiety is optionally substituted with one to five independently selected $R^{12}$.

The present invention also relates to a compound of the formula 1b:

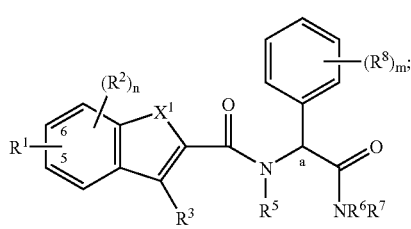

or a pharmaceutically acceptable salt thereof, wherein:

$R^1$ is substituted at the 5 or 6 position of formula 1b and has the structure:

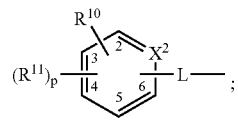

or when $R^7$ is phenyl, pyridyl, phenyl-$Z^1$- or pyridyl-$Z^1$- optionally substituted with one to five independently selected $R^{12}$, $R^1$ is ($C_1$-$C_6$)alkyl, ($C_3$-$C_8$)cycloalkyl, ($C_5$-$C_{10}$)bicycloalkyl, —($CR^aR^b$)$_t$O($C_1$-$C_6$ alkyl), —($CR^aR^b$)$_t$S($C_1$-$C_6$ alkyl), —($CR^aR^b$)$_r$C(O)$R^{15}$, —($CR^aR^b$)$_r$$R^{15}$, —$SO_2R^{15}$, ($C_4$-$C_{10}$)heterocyclyl, ($C_5$-$C_{10}$)heteroaryl, aryl or —($CR^aR^b$)$_q$-aryl, wherein the cycloalkyl, heterocyclyl, heteroaryl or aryl moiety is optionally substituted with from one to five independently selected $R^{16}$;

m is an integer from 0 to 5;
n is an integer from 0 to 3;
p is an integer from 0 to 3;
L is —C(O)N($R^9$)—, as described above;
$X^1$ is N($R^4$), S or O;
$X^2$ is N or C($R^c$);
$R^2$, $R^8$, $R^{11}$, $R^{12}$, $R^{13}$ and $R^{16}$ are each independently selected from halo, cyano, nitro, azido, amino, hydroxy, ($C_1$-$C_6$)alkyl, ($C_2$-$C_6$)alkoxy, methoxy, ($C_1$-$C_6$)alkoxy($C_1$-$C_6$)alkyl, mono-, di- or tri-halo($C_2$-$C_6$)alkyl, perfluoro($C_2$-$C_4$)alkyl, trifluoromethyl, trifluoromethyl($C_1$-$C_5$)alkyl, mono-, di- or tri-halo($C_2$-$C_6$)alkoxy, trifluoromethyl($C_1$-$C_5$)alkoxy, ($C_1$-$C_6$)alkylthio, hydroxy($C_1$-$C_6$)alkyl, ($C_3$-$C_8$)cycloalkyl ($CR^aR^b$)$_q$—, ($C_2$-$C_6$)alkenyl, ($C_2$-$C_6$)alkynyl, ($C_1$-$C_6$)alkylamino-, ($C_1$-$C_6$)dialkylamino, amino($C_1$-$C_6$)alkyl-, —($CR^aR^b$)$_q$$NR^aR^{14}$, —C(O)$NR^aR^{14}$, —$NR^{14}$C(O)$R^{15}$, —$NR^{14}OR^{15}$, —CH=$NOR^{15}$, —$NR^{14}$C(O)$OR^{15}$, —$NR^{14}$S(O)$_j$$R^{15}$, —C(O)$R^{15}$, —C(S)$R^{15}$, —C(O)$OR^{15}$, —OC(O)$R^{15}$, —$SO_2NR^aR^{14}$, —S(O)$_j$$R^{15}$, or —($CR^aR^b$)$_q$S(O)$_j$$R^{15}$;

each $R^a$ and $R^b$ is independently H or ($C_1$-$C_6$)alkyl;
$R^c$ is H or $R^{11}$;
each q is independently an integer from 0 to 6;
each j is independently 0, 1 or 2;
$R^3$ is H, halo, ($C_1$-$C_6$)alkyl, or mono-, di- or tri-halo($C_1$-$C_6$)alkyl;
$R^4$ is H, ($C_1$-$C_6$)alkyl, ($C_3$-$C_8$)cycloalkyl, —C(O)$R^{15}$, —C(S)$R^{15}$, —($CR^aR^b$)$_t$O($C_1$-$C_6$ alkyl), —($CR^aR^b$)$_t$S($C_1$-$C_6$ alkyl), —($CR^aR^b$)$_r$C(O)$R^{15}$, —($CR^aR^b$)$_r$$R^{15}$, —$SO_2R^{15}$ or —($CR^aR^b$)$_q$-phenyl, wherein the phenyl moiety is optionally substituted with from one to five independently selected $R^{16}$;

each r is independently an integer from 2 to 5;
each t is independently an integer from 1 to 6;
$R^5$ and $R^9$ are each independently H, ($C_1$-$C_6$)alkyl, ($C_3$-$C_8$)cycloalkyl, —C(O)$R^{15}$, —C(S)$R^{15}$, —($CR^aR^b$)$_q$O($C_1$-$C_6$ alkyl), —($CR^aR^b$)$_q$S($C_1$-$C_6$ alkyl), —($CR^aR^b$)$_r$C(O)$R^{15}$, —($CR^aR^b$)$_r$$R^{15}$ or —$SO_2R^{15}$;

$R^6$ is H, ($C_1$-$C_6$)alkyl, ($C_3$-$C_8$)cycloalkyl, —C(O)$R^{15}$, —C(S)$R^{15}$, —($CR^aR^b$)$_q$O($C_1$-$C_6$ alkyl), —($CR^aR^b$)$_q$S($C_1$-$C_6$ alkyl), —($CR^aR^b$)$_r$C(O)$R^{15}$, —($CR^aR^b$)$_r$$R^{15}$ or —$SO_2R^{15}$;

y is an integer from 0 to 5;
$R^7$ is ($C_1$-$C_6$)alkyl, ($C_2$-$C_6$)alkenyl, ($C_2$-$C_6$)alkynyl, —($CR^aR^b$)$_q$O($C_1$-$C_6$ alkyl), —($CR^aR^b$)$_q$S($C_1$-$C_6$ alkyl); ($C_3$-$C_8$)cycloalkyl, —C(O)$R^{15}$, —C(S)$R^{15}$, —($CR^aR^b$)$_q$C(O)$R^{15}$, —($CR^aR^b$)$_r$C(S)$R^{15}$, —($CR^aR^b$)$_r$$R^{15}$ or —$SO_2R^{15}$;

or $R^7$ is phenyl, pyridyl, phenyl-$Z^1$- or pyridyl-$Z^1$- optionally substituted with one to five independently selected $R^{12}$;

or $R^6$ and $R^7$ taken together with the nitrogen atom to which they are attached together comprise ($C_4$-$C_{10}$)heterocyclyl, wherein the heterocyclyl moiety is monocyclic;

wherein the alkyl, cycloalkyl, and heterocyclyl moieties of the foregoing $R^6$ and $R^7$ groups are optionally substituted independently with 1 to 3 substituents independently selected from halo, cyano, nitro, trifluoromethyl, trifluoromethoxy, azido, —$OR^{15}$, —$C(O)R^{15}$, —$C(O)OR^{15}$, —$OC(O)R^{15}$, —$NR^{14}C(O)R^{15}$, —$C(O)NR^aR^{14}$, —$NR^aR^{14}$, and —$NR^{14}OR^{15}$, $C_1$-$C_6$ alkyl, $C_2$-$C_6$ alkenyl, and $C_2$-$C_6$ alkynyl; and $R^{10}$ is phenyl, pyridyl, phenyl-$Z^2$- or pyridyl-$Z^2$-, wherein the phenyl or pyridyl moiety is optionally substituted with one to five independently selected $R^{13}$;

$Z^2$ is —$S(O)_j$—, —$O$—, —$(CR^aR^b)_w$—, or —$(O)_k(CR^aR^b)_w(O)_k(CR^aR^b)_q$—;

w is independently an integer from 1 to 6;

each k is independently 0 or 1;

or $R^{10}$ is $OR^{17}$, wherein $R^{17}$ is $(C_1$-$C_6)$alkyl, $(C_1$-$C_6)$alkoxy $(C_1$-$C_6)$alkyl, mono-, di- or tri-halo$(C_2$-$C_6)$alkyl, perfluoro $(C_2$-$C_4)$alkyl, trifluoromethyl$(C_1$-$C_5)$alkyl, hydroxy$(C_1$-$C_6)$alkyl, $(C_3$-$C_8)$cycloalkyl$(CR^aR^b)_q$—, $(C_2$-$C_6)$alkenyl, or $(C_2$-$C_6)$alkynyl;

each $R^{14}$ is independently H, $(C_1$-$C_6)$alkyl, $(C_3$-$C_8)$cycloalkyl, —$C(O)R^{15}$, —$C(S)R^{15}$, —$(CR^aR^b)_tO(C_1$-$C_6$ alkyl), —$(CR^aR^b)_tS(C_1$-$C_6$ alkyl), —$(CR^aR^b)_rC(O)R^{15}$, —$(CR^aR^b)_rR^{15}$ or —$SO_2R^{15}$;

each $R^{15}$ is independently H, $(C_1$-$C_6)$alkyl, $(C_3$-$C_8)$cycloalkyl, trifluoromethyl, trifluoromethyl$(C_1$-$C_5)$alkyl, wherein the alkyl, moieties of the foregoing $R^{15}$ groups are independently optionally substituted with 1 to 3 substituents independently selected from $C_1$-$C_6$ alkyl, $C_1$-$C_6$ alkoxy, amino, hydroxy, halo, cyano, nitro, trifluoromethyl and trifluoromethoxy;

and wherein any of the above "alkyl", "alkenyl" or "alkynyl" moieties comprising a $CH_3$ (methyl), $CH_2$ (methylene), or CH (methine) group which is not substituted with halogen, SO or $SO_2$, or attached to a N, O or S atom, optionally bears on said methyl, methylene or methine group a substituent selected from the group consisting of halo, —$OR^a$, —$SR^a$ and —$NR^aR^b$.

In an embodiment of the invention, $X^2$ is $C(R^c)$.

In another embodiment of the invention, $X^2$ is $C(R^c)$ and L is attached to the 2 position of $R^1$ and to the 5 position of formula 1b.

In another embodiment of the invention, $X^2$ is $C(R^c)$ and L is attached to the 2 position of $R^1$ and to the 5 position of formula 1b, $R^{10}$ is $OR^{17}$ and $R^7$ is phenyl-$Z^1$, wherein the phenyl moiety is optionally substituted with one to five independently selected $R^{12}$. In a preferred embodiment thereof, $Z^1$ is —$(CR^aR^b)_t$—.

In another embodiment of the invention, $X^2$ is $C(R^c)$ and L is attached to the 2 position of $R^1$ and to the 5 position of formula 1b, and $R^{10}$ is phenyl attached at the 3 position of $R^1$, wherein the phenyl moiety of $R^{10}$ is optionally substituted with one to five independently selected $R^{13}$. In a preferred embodiment of the invention, $R^6$ in formula 1b is H or $(C_1$-$C_4)$alkyl.

In another preferred embodiment of the invention, the carbon designated "a" in formula 1b is in the (S) absolute configuration.

In another embodiment of the invention, $R^{13}$ in formula 1b is H or trifluoromethyl.

In another preferred embodiment of the invention, $R^3$ in formula 1b is H, halo, or $(C_1$-$C_6)$alkyl In another preferred embodiment of the invention, $R^7$ in formula 1b is $(C_1$-$C_6)$alkyl, $(C_2$-$C_6)$alkenyl or $(C_2$-$C_6)$alkynyl.

In a particularly preferred embodiment of the invention, the compound is selected from the group consisting of:

3-Chloro-1-methyl-5-[(4'-trifluoromethyl-biphenyl-2-carbonyl)amino]-1H-indole-2-carboxylic acid [2-oxo-1-phenyl-2-(prop-2-ynylamino)ethyl]amide;

3-Chloro-1-methyl-5-[(4'-trifluoromethyl-biphenyl-2-carbonyl)-amino]-1H-indole-2-carboxylic acid [2-(isopropylamino-2-oxo-1-phenylethyl]amide;

3-Chloro-1-methyl-5-[(4'-trifluoromethyl-biphenyl-2-carbonyl)-amino]-1H-indole-2-carboxylic acid [2-oxo-1-phenyl-2-(propylamino)ethyl]amide;

3-Chloro-1-methyl-5-[methyl-(4'-trifluoromethyl-biphenyl-2-carbonyl)-amino]-1H-indole-2-carboxylic acid [2-(ethylamino)-2-oxo-1-phenylethyl]amide;

3-Chloro-1-methyl-5-[methyl-(4'-trifluoromethyl-biphenyl-2-carbonyl)-amino]-1H-indole-2-carboxylic acid [2-(isopropylamino-2-oxo-1-phenylethyl]amide;

5-[(Biphenyl-2-carbonyl)amino]-3-chloro-1-methyl-1H-indole-2-carboxylic acid [2-oxo-1-phenyl-2-(propylamino)ethyl]amide; and 5[(Biphenyl-2-carbonyl)amino]-3-chloro-1-methyl-1H-indole-2-carboxylic acid [2-(isopropylamino-2-oxo-1-phenylethyl]amide.

In an embodiment of the invention, $R^6$ and $R^7$ in formula 1b taken together with the nitrogen atom to which they are attached together comprise $(C_4$-$C_{10})$heterocyclyl, wherein the heterocyclyl is optionally substituted independently with 1 or 2 substituents independently selected from $(C_1$-$C_6)$alkyl, $(C_2$-$C_6)$alkenyl, and $(C_2$-$C_6)$alkynyl and trifluoromethyl. In a preferred embodiment thereof, the heterocyclyl is selected from pyrrolidinyl, piperidinyl, morpholino and thiomorpholino. In a particularly preferred embodiment thereof, the heterocyclyl is pyrrolidinyl or morpholino.

The present invention also relates to compounds of the formula 2:

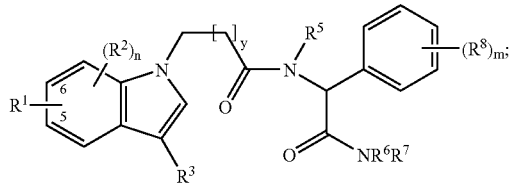

or a pharmaceutically acceptable salt thereof, wherein:

$R^1$ is substituted at the 5 or 6 position of formula 1 and has the structure:

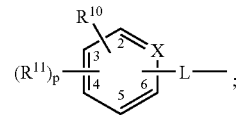

m is an integer from 0 to 5;

n is an integer from 0 to 3;

p is an integer from 0 to 3;

L is —$C(O)N(R^9)$—;

X is N or $C(R^c)$;

$R^2$, $R^8$, $R^{11}$, $R^{12}$ and $R^{13}$ are each independently selected from halo, cyano, nitro, azido, amino, hydroxy, $(C_1$-$C_6)$alkyl, $(C_2$-$C_6)$alkoxy, methoxy, $(C_1$-$C_6)$alkoxy$(C_1$-$C_6)$alkyl, mono-, di- or tri-halo$(C_2$-$C_6)$alkyl, perfluoro$(C_2$-$C_4)$alkyl, trifluoromethyl, trifluoromethyl$(C_1$-$C_5)$alkyl, mono-, di- or tri-halo$(C_2$-$C_6)$alkoxy, trifluoromethyl$(C_1$-$C_5)$alkoxy, $(C_1$-

$C_6$)alkylthio, hydroxy($C_1$-$C_6$)alkyl, ($C_3$-$C_8$)cycloalkyl (CR$^a$R$^b$)$_q$—, ($C_2$-$C_6$)alkenyl, ($C_2$-$C_6$)alkynyl, ($C_1$-$C_6$)alkylamino-, ($C_1$-$C_6$)dialkylamino, amino($C_1$-$C_6$)alkyl-, —(CR$^a$R$^b$)$_q$NR$^a$R$^{14}$, —C(O)NR$^a$R$^{14}$, —NR$^{14}$C(O)R$^{15}$, —NR$^{14}$OR$^{15}$, —CH=NOR$^{15}$, —NR$^{14}$C(O)OR$^{15}$, —NR$^{14}$S(O)$_j$R$^{15}$, —C(O)R$^{15}$, —C(S)R$^{15}$, —C(O)OR$^{15}$, —OC(O)R$^{15}$, —SO$_2$NR$^a$R$^{14}$, —S(O)$_j$R$^{15}$, or —(CR$^a$R$^b$)$_q$S(O)$_j$R$^{15}$;

each R$^a$ and R$^b$ is independently H or ($C_1$-$C_6$)alkyl;
R$^c$ is H or R$^{11}$;
each q is independently an integer from 0 to 6;
each j is independently 0, 1 or 2:
R$^3$ is H, halo, ($C_1$-$C_6$)alkyl, or mono-, di- or tri-halo($C_1$-$C_6$)alkyl;
each r is independently an integer from 2 to 5;
each t is independently an integer from 1 to 6;
R$^5$ and R$^9$ are each independently H, ($C_1$-$C_6$)alkyl, ($C_3$-$C_8$)cycloalkyl, —C(O)R$^{15}$, —C(S)R$^{15}$, —(CR$^a$R$^b$)$_r$O($C_1$-$C_6$ alkyl), —(CR$^a$R$^b$)$_r$S($C_1$-$C_6$ alkyl), —(CR$^a$R$^b$)$_r$C(O)R$^{15}$, —(CR$^a$R$^b$)$_r$R$^{15}$ or —SO$_2$R$^{15}$;
R$^6$ is H, ($C_1$-$C_6$)alkyl, ($C_3$-$C_8$)cycloalkyl, —C(O) R$^{15}$, —C(S)R$^{15}$, —(CR$^a$R$^b$)$_q$O($C_1$-$C_6$ alkyl), —(CR$^a$R$^b$)$_q$S($C_1$-$C_6$ alkyl), —(CR$^a$R$^b$)$_r$C(O)R$^{16}$, —(CR$^a$R$^b$)$_r$R$^{15}$ or —SO$_2$R$^{15}$;
y is an integer from 0 to 5;
R$^7$ is ($C_1$-$C_6$)alkyl, ($C_2$-$C_6$)alkenyl, ($C_2$-$C_6$)alkynyl, —(CR$^a$R$^b$)$_q$O($C_1$-$C_6$ alkyl), —(CR$^a$R$^b$)$_q$S($C_1$-$C_6$ alkyl); ($C_3$-$C_8$)cycloalkyl, —C(O)R$^{15}$, —C(S)R$^{15}$, —(CR$^a$R$^b$)$_r$C(O)R$^{15}$, (CR$^a$R$^b$)$_r$C(S)R$^{15}$, —(CR$^a$R$^b$)$_r$R$^{15}$ or —SO$_2$R$^{15}$;
or R$^7$ is phenyl, pyridyl, phenyl-Z$^1$- or pyridyl-Z$^1$- optionally substituted with one to five independently selected R$^{12}$;
or R$^6$ and R$^7$ taken together with the nitrogen atom to which they are attached together comprise ($C_4$-$C_{10}$)heterocyclyl, wherein the heterocyclyl moiety is monocyclic;
wherein the alkyl, cycloalkyl, and heterocyclyl moieties of the foregoing R$^6$ and R$^7$ groups are optionally substituted independently with 1 to 3 substituents independently selected from halo, cyano, nitro, trifluoromethyl, trifluoromethoxy, azido, —OR$^{15}$, —C(O)R$^{15}$, —C(O)OR$^{15}$, —OC(O)R$^{15}$, —NR$^{14}$C(O)R$^{15}$, —C(O)NR$^a$R$^{14}$, —NR$^a$R$^{14}$, and —NR$^{14}$R$^{15}$, $C_1$-$C_6$ alkyl, $C_2$-$C_6$ alkenyl, and $C_2$-$C_6$ alkynyl; and
R$^{10}$ is phenyl, pyridyl, phenyl-Z$^2$- or pyridyl-Z$^2$-, wherein the phenyl or pyridyl moiety is optionally substituted with one to five independently selected R$^{13}$;
Z$^2$ is —S(O)$_j$—, —O—, —(CR$^a$R$^b$)$_w$—, or —(O)$_k$(CR$^a$R$^b$)$_w$(O)$_k$(CR$^a$R$^b$)$_q$—;
w is independently an integer from 1 to 6;
each k is independently 0 or 1;
or R$^{10}$ is OR$^{17}$, wherein R$^{17}$ is ($C_1$-$C_6$)alkyl, ($C_1$-$C_6$)alkoxy($C_1$-$C_6$)alkyl, mono-, di- or tri-halo($C_2$-$C_6$)alkyl, perfluoro($C_2$-$C_4$)alkyl, trifluoromethyl($C_1$-$C_5$)alkyl, hydroxy($C_1$-$C_6$) alkyl, ($C_3$-$C_8$)cycloalkyl(CR$^a$R$^b$)$_q$—, ($C_2$-$C_6$)alkenyl, or ($C_2$-$C_6$)alkynyl;
each R$^{14}$ is independently H, ($C_1$-$C_6$)alkyl, ($C_3$-$C_8$)cycloalkyl, —C(O)R$^{15}$, —C(S)R$^{15}$, —(CR$^a$R$^b$)$_r$O($C_1$-$C_6$ alkyl), —(CR$^a$R$^b$)$_r$S($C_1$-$C_6$ alkyl), —(CR$^a$R$^b$)$_r$C(O)R$^{15}$, —(CR$^a$R$^b$)$_r$R$^{15}$ or —SO$_2$R$^{15}$;
each R$^{15}$ is independently H, ($C_1$-$C_6$)alkyl, ($C_3$-$C_8$)cycloalkyl, trifluoromethyl, trifluoromethyl($C_1$-$C_5$)alkyl, wherein the alkyl, moieties of the foregoing R$^{15}$ groups are independently optionally substituted with 1 to 3 substituents independently selected from $C_1$-$C_6$ alkyl, $C_1$-$C_6$ alkoxy, amino, hydroxy, halo, cyano, nitro, trifluoromethyl and trifluoromethoxy;
and wherein any of the above "alkyl", "alkenyl" or "alkynyl" moieties comprising a CH$_3$ (methyl), CH$_2$ (methylene), or CH (methine) group which is not substituted with halogen, SO or SO$_2$, or attached to a N, O or S atom, optionally bears on said methyl, methylene or methine group a substituent selected from the group consisting of halo, —OR$^a$, —SR$^a$ and —NR$^a$R$^b$.

In an embodiment of the invention, X in formula 2 is C(R$^c$).
In another embodiment of the invention, L in formula 2 is attached to the 2 position of R$^1$ and to the 5 position of formula 2.
In another embodiment of the invention, wherein y is 1 or 2.
In another embodiment of the invention, R$^{10}$ in formula 2 is phenyl attached at the 3 position of R$^1$, wherein the phenyl moiety of R$^{10}$ is optionally substituted with one to five independently selected R$^{13}$.
In another embodiment of the invention, R$^7$ in formula 2 is phenyl-Z$^1$, wherein the phenyl moiety is optionally substituted with one to five independently selected R$^{12}$. In a preferred embodiment thereof, Z$^1$ is —(CR$^a$R$^b$)$_t$—.
In another embodiment of the invention, R$^6$ in formula 2 is H or ($C_1$-$C_4$)alkyl.
In another embodiment of the invention, the carbon designated "a" in formula 2 is in the (S) absolute configuration.
In a preferred embodiment of the invention, R$^{13}$ in formula 2 is trifluoromethyl.
In another preferred embodiment of the invention, R$^3$ in formula 2 is H, halo, or ($C_1$-$C_6$)alkyl.
The invention also relates to a process for preparing a compound of formula 1 which comprises forming an amide linkage between a compound of the formula AB1:

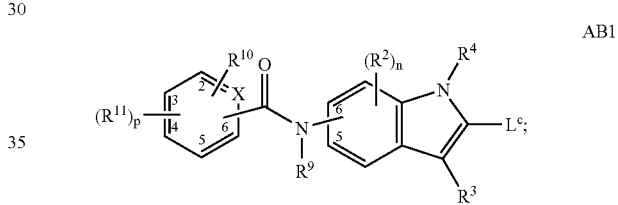

AB1 and a compound of the formula C:

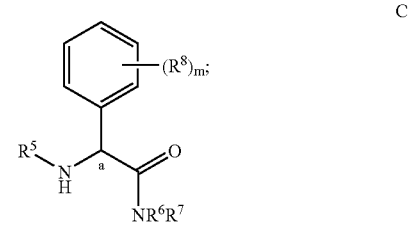

C wherein
m is an integer from 0 to 5; n is an integer from 0 to 3; p is an integer from 0 to 3;
the amido nitrogen atom of —C(O)N(R$^9$)— above is bonded to the 5 or 6 position of the indole;
X is N or C(R$^c$), wherein R$^c$ is H or R$^{11}$;
R$^2$, R$^8$, R$^{11}$, R$^{12}$, R$^{13}$ and R$^{16}$ are each independently selected from halo, cyano, nitro, azido, amino, hydroxy, ($C_1$-$C_6$)alkyl, ($C_2$-$C_6$)alkoxy, methoxy, ($C_1$-$C_6$)alkoxy($C_1$-$C_6$)alkyl, mono-, di- or tri-halo($C_2$-$C_6$)alkyl, perfluoro($C_2$-$C_4$) alkyl, trifluoromethyl, trifluoromethyl($C_1$-$C_5$)alkyl, mono-, di- or tri-halo($C_1$-$C_6$)alkoxy, trifluoromethyl($C_1$-$C_5$)alkoxy, ($C_1$-$C_6$)alkylthio, hydroxy($C_1$-$C_6$)alkyl, ($C_3$-$C_8$)cycloalkyl (CR$^a$R$^b$)$_q$—, ($C_2$-$C_6$)alkenyl, ($C_2$-$C_6$)alkynyl, ($C_1$-$C_6$)alkylamino-, ($C_1$-$C_6$)dialkylamino, amino($C_1$-$C_6$)alkyl-, —$(CR^aR^b)_q NR^aR^{14}$, —$C(O)NR^aR^{14}$, —$NR^{14}C(O)R^{15}$, —$NR^{14}OR^{15}$, —$CH=NOR^{15}$, —$NR^{14}C(O)OR^{15}$, —$NR^{14}S(O)_j R^{15}$, —$C(O)R^{15}$, —$C(S)R^{15}$, —$C(O)OR^{15}$, —$OC(O)R^{15}$, —$SO_2 NR^a R^{14}$, —$S(O)_j R^{15}$, or —$(CR^a R^b)_q S(O)_j R^{15}$;

each $R^a$ and $R^b$ is independently H or $(C_1-C_6)$alkyl;

each q is independently an integer from 0 to 6; each j is independently 0, 1 or 2;

$R^3$ is H, halo, $(C_1-C_6)$alkyl, or mono-, di- or tri-halo$(C_1-C_6)$alkyl;

$R^4$ is H, $(C_1-C_6)$alkyl, $(C_3-C_8)$cycloalkyl, —$C(O)R^{15}$, —$C(S)R^{15}$, —$(CR^aR^b)_tO(C_1-C_6$ alkyl), —$(CR^aR^b)_tS(C_1-C_6$ alkyl), —$(CR^aR^b)_tC(O)R^{15}$, —$(CR^aR^b)_tR^{15}$, —$SO_2R^{15}$ or —$(CR^aR^b)_q$-phenyl, wherein the phenyl moiety is optionally substituted with from one to five independently selected $R^{16}$;

each r is independently an integer from 2 to 5; each t is independently an integer from 1 to 6;

$R^5$, $R^6$ and $R^9$ are each independently H, $(C_1-C_6)$alkyl, $(C_3-C_8)$cycloalkyl, —$C(O)R^{15}$, —$C(S)R^{15}$, —$(CR^aR^b)_tO(C_1-C_6$ alkyl), —$(CR^aR^b)_tS(C_1-C_6$ alkyl), —$(CR^aR^b)_tC(O)R^{15}$, —$(CR^aR^b)_tR^{15}$ or —$SO_2R^{15}$;

$R^7$ is phenyl, pyridyl, phenyl-$Z^1$- or pyridyl-$Z^1$-, wherein the phenyl or pyridyl moiety is optionally substituted with one to five independently selected $R^{12}$;

$Z^1$ is —$SO_2$— or —$(CR^aR^b)_v$—;

v is independently an integer from 1 to 6;

$R^{10}$ is phenyl, pyridyl, phenyl-$Z^2$- or pyridyl-$Z^2$-, wherein the phenyl or pyridyl moiety is optionally substituted with one to five independently selected $R^{13}$;

$Z^2$ is —$S(O)_j$—, —O—, —$(CR^aR^b)_w$—, or —$(O)_k(CR^aR^b)_w(O)_k(CR^aR^b)_q$—;

w is independently an integer from 1 to 6;

each k is independently 0 or 1;

each $R^{14}$ is independently H, $(C_1-C_6)$alkyl, $(C_3-C_8)$cycloalkyl, —$C(O)R^{15}$, —$C(S)R^{15}$, —$(CR^aR^b)_tO(C_1-C_6$ alkyl), —$(CR^aR^b)_tS(C_1-C_6$ alkyl), —$(CR^aR^b)_tC(O)R^{15}$, —$(CR^aR^b)_tR^{15}$ or —$SO_2R^{15}$;

each $R^{15}$ is independently H, $(C_1-C_6)$alkyl, $(C_3-C_8)$cycloalkyl, trifluoromethyl, trifluoromethyl$(C_1-C_5)$alkyl, wherein the alkyl, moieties of the foregoing $R^{15}$ groups are independently optionally substituted with 1 to 3 substituents independently selected from $C_1-C_6$ alkyl, $C_1-C_6$ alkoxy, amino, hydroxy, halo, cyano, nitro, trifluoromethyl and trifluoromethoxy;

and wherein any of the above "alkyl", "alkenyl" or "alkynyl" moieties comprising a $CH_3$ (methyl), $CH_2$ (methylene), or CH (methine) group which is not substituted with halogen, SO or $SO_2$, or attached to a N, O or S atom, optionally bears on said methyl, methylene or methine group a substituent selected from the group consisting of halo, —$OR^a$, —$SR^a$ and —$NR^aR^b$;

and $L^c$ is selected from a (i) a carboxylic acid or salt thereof (ii) an activated form of the carboxylic acid or (iii) an aldehyde.

In an embodiment, the carboxylic acid is optionally activated in-situ, using methods well known in the art. The above process is referred to herein as "Process I." Process I is applicable to, and provides, a process for preparing each of the embodiments, preferred embodiments, more preferred embodiments and particularly preferred embodiments of the compound of formula 1, a detailed repetition of which is avoided for brevity. Methods for forming amide linkages are well-known in the art, some examples of which are provided herein.

In an embodiment, the employed form of the amine C may optionally be a salt with any acid that is compatible with the subsequent process options, and may additionally or optionally be a solution in a similarly compatible solvent or mixture of solvents.

In an embodiment, the employed forms of the carboxylic acid (or salt thereof) AB1 and amine C (or salt thereof) optionally include solvates and hydrates.

In an embodiment of Process I, the amide linkage between AB1 and C is formed by combining AB1, C, and PyBroP (about 1 eq) in a suitable non-aqueous solvent, followed by the addition of diisopropylethylamine (2-3 eq). In a preferred embodiment, the suitable solvent is methylene chloride or DMF. In a more preferred embodiment of Process I, the solvent is methylene chloride. In another preferred embodiment, Process I further comprises stirring or agitating the resulting mixture at room temperature for a period of from about 30 minutes to about 24 hours. In another preferred embodiment thereof, of Process I further comprises removal of the solvent and the purification of the product by TLC or flash chromatography using ethyl acetate/hexane as the eluting solvent.

In another embodiment of Process I, the amide linkage between AB1, wherein $L^c$ is an aldehyde, preferably C(O)H, and C is formed by a process (herein, the "Aldehyde Process") which comprises (a) reacting the AB1 aldehyde with C in the presence of an acid, preferably acetic acid, in a suitable solvent, preferably methylene chloride, followed by (b) addition of $NaB(OAc)_3H$ and chloroform. In an preferred embodiment of the Aldehyde Process, the compound of formula 1 is purified from the organic layer, preferably by flash chromatography using methanol/chloroform. In a further embodiment of the Aldehyde Process, the AB1 aldehyde is formed by (i) combining a compound of formula AB1, wherein $L^c$ is a carboxylic acid, preferably —COOH, with N,O-dimethyl hydroxylamine hydrochloride salt and PyBroP in a suitable solvent; followed by (ii) addition of diisopropylethylamine and (iii) treatment of the resulting N,O-dimethyl hydroxyamide with DIBAL in a suitable solvent, to yield the corresponding aldehyde. In a preferred embodiment of the Aldehyde Process, the suitable solvent in step (i) is methylene chloride. In another preferred embodiment of the Aldehyde Process, the suitable solvent in step (iii) is THF.

In a preferred embodiment of Process I, referred to herein as "Process IC" for its use of carbodiimide, the amide linkage between AB1 and C, wherein $L^c$ is a carboxylic acid, is formed by (a) combining AB1 with a carbodiimide and a catalyst, e.g., 1-hydroxybenzotriazole hydrate ("HOBt"), in a suitable non-aqueous solvent, and (b) adding triethylamine and C to the mixture of step (a). In a more preferred embodiment of Process IC, the carbodiimide is EDC, i.e., 1-[3-(dimethylamino)propyl]-3-ethylcarbodimide hydrochloride, and even more preferably, the solvent is methylene chloride. In another embodiment, Process IC further comprises at least a second addition of triethylamine. In another embodiment, Process IC further comprises at least a second addition of triethylamine, optionally with further addition of the carbodiimide. In another embodiment of Process IC, a salt of the acid AB1 is used in step (a). Preferably, the salt is a sodium salt, i.e., $L^c$ is —$C(O)O^-Na^+$, and more preferably, the salt is a potassium salt, i.e., $L^c$ is —$C(O)O^-K^+$ and particularly preferably, the salt is a potassium salt, i.e., $L^c$ is —$C(O)O^-K^+$, crystallizing as the 2.5 mole hydrate. In a still further embodiment thereof, the acid salt AB1 is first treated with aqueous acid before combination with the other components in step (a); in this embodiment, the treatment with aqueous acid resulting in precipitation of the free acid as a solid, which is collected for use in step (a). In a preferred embodiment of the acid treatment step, the acid salt AB1 is treated with aqueous acid adjusted to a pH of from about 3 to about 4, with heating. In a more preferred embodiment, the acid salt is treated with an inert mineral acid, most preferably concentrated aqueous hydrochloric acid, or alternatively, an inert organic acid, preferably anhydrous and most preferably methanesulfonic acid, before step (a). In a still further embodiment, the compound of formula 1 is purified by (a) washing in saturated aqueous sodium hydrogen carbonate, (b) washing in aqueous acid, preferably, hydrochloric acid, and (c) washing with water, to provide purified compound of formula 1 in the non-aqueous solvent. In a still further embodiment, the non-aqueous solvent is replaced with amyl acetate, amyl alcohol, mixtures of methanol or acetonitrile with diisopropyl ether, or preferably mixtures of propan-2-ol and tert-butyl methyl ether, by distillation, and the solution is cooled in order to precipitate solid forms, e.g., polymorphs, of the compound of formula 1. Preferably, the solution of compound of formula 1 in mixtures of propan-2-ol and tert-butyl methyl ether is seeded with the desired solid form to facilitate precipitation of the desired solid form.

In another embodiment of the above process, the amide linkage between AB1 and C is formed by (a) reaction of the acid the 1,1'-carbonyldiiimidazole to produce its acyl imidazolide, i.e., yielding e.g., $L^c$=—C(O)(1-$C_3H_3N_2$), and (b) reacting the imidazolide of AB1 with C, preferably in the presence of a suitable base. In this embodiment, some racemization of chiral center "a" in (S)-phenylglycine derivatives has been observed, thus, where preservation of stereochemistry is desirable, the use of the imidazolide reaction is less preferred than other embodiments described above. Preferred processes of the invention preserve the stereochemistry of the phenylglycine group.

In a preferred embodiment of each of the embodiments of Process I and Process IC, $R^5$ is hydrogen, $R^6$ is hydrogen, $R^7$ is benzyl, m, n and p are all 0, and the carbon designated "a" in formula C is in the (S) configuration. In another preferred embodiment of Process I, the amide linkage between AB1 and C is formed as in Example 45, step (g). In a preferred embodiment of Process IC, $R^4$ is methyl, $R^5$ is hydrogen, $R^6$ is methyl, $R^7$ is benzyl, m is 0 and the carbon designated "a" in formula C is in the (S) configuration and the amide linkage between AB1 and C is formed as in Example 44, step (f).

Additional embodiments of methods for forming the amide linkages of the processes of this invention are described in the Examples, and it is to be understood that each of the embodiments exemplified as described below are intended to be included within the scope of the processes of this invention.

In a further embodiment of the above process, the compound of formula AB1 is prepared by a process which comprises forming an amide linkage between a compound of the formula A:

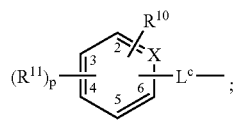

and a compound of the formula B1:

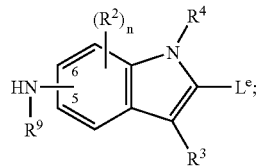

wherein $L^c$ is a carboxylic acid and $L^e$ is a carboxylic acid ($C_1$-$C_6$)alkyl ester, and $R^2$-$R^{11}$ are as defined above.

In an embodiment, the amide linkage between A and B1 is formed by a process comprising (a) combining A and B1 with a suitable base, e.g. DIEA, a carbodiimide, e.g., EDC.HCl, and a catalyst, e.g. HOBT, in an organic solvent, e.g. DMF, followed by (b) distillation of volatile components, (c) partition between organic solvent and dilute aqueous acid, (d) replacement by distillation of the solvent with a non-solvent, e.g. tert-butyl methyl ether, diisopropyl ether or propan-1-ol, and (e) isolation of the product AB1-e by filtration.

In another embodiment, the amide linkage between A and B1 is formed by a process comprising (a) combining A with a chlorinating agent, e.g. oxalyl chloride or preferably thionyl chloride, in a compatible solvent e.g. toluene, acetonitrile, or 1,2-dichloroethane, in the presence of a catalyst to prepare the acid chloride, i.e. A wherein $L^c$=—C(O)Cl, (b) optionally removing the excess reagent by distillation, (c) combining the acid chloride with B1 in the presence of a suitable base, e.g. DIEA, in compatible solvents, e.g. DCE, Toluene, EtOAc, acetonitrile, and mixtures thereof, followed by (d) isolation of product AB1-e as described in the preceding embodiment, or preferably by filtration of crude product from the reaction mixture, and reslurry of the crude in suitable non-solvents, preferably in mixtures of aqueous propan-2-ol, before refiltration.

A preferred feature of the above embodiment is the use of catalysis in the preparation of the acid chloride, i.e. A wherein $L^c$=—C(O)Cl, to prevent the formation of the corresponding symmetrical carboxylic anhydride. Preferred catalysts are tertiary amides, e.g. DMF and DMAC, or pyridines, e.g. pyridine or DMAP or mixtures thereof. More preferred catalysts are tertiarybenzamides, e.g. N,N-dimethylbenzamide. Even more preferred catalysts are N-alkyl lactams, e.g. N-methylpyrrolidinone. Catalysis by iron salts and by tetraalkylureas, e.g. tetramethylurea, is known in the art.

The invention also relates to a compound of the formula AB1

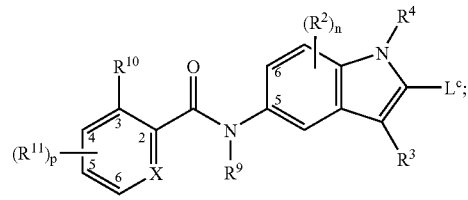

wherein $R^3$ is H, halo or ($C_1$-$C_6$)alkyl, $R^4$ and $R^9$ are each independently H or ($C_1$-$C_6$)alkyl; m, n, and p are all 0, $R^{10}$ is phenyl optionally substituted with from one to five $R^{13}$ groups and $L^c$ is a carboxylic acid or salt thereof. In a preferred embodiment, $L^c$ is COOH. In another preferred embodiment, $L^c$ is a salt of the carboxylic acid, preferably $L^c$ is the sodium salt of the carboxylic acid, i.e., —COO$^-$Na$^+$, more preferably $L^c$ is the potassium salt of the carboxylic acid, i.e., —COO$^-$K$^+$, and particularly preferably $L^c$ is the potassium salt of the carboxylic acid, i.e., —COO$^-$K$^+$, crystallizing as a 2.5 mole hydrate. In a preferred embodiment of the compound of formula AB1, $R^3$ is H or halo, $R^4$ is methyl, ethyl or propyl; m, n and p are both 0, and $R^{10}$ is phenyl optionally substituted with one or two $R^{13}$ groups. In a more preferred embodiment thereof, $R^3$ is H and $R^4$ is methyl. In another more preferred embodiment thereof, $R^3$ is H, $R^4$ is methyl and $R^{10}$ is phenyl optionally substituted with one $R^{13}$ group. In a particularly preferred embodiment, $R^3$ is H, $R^4$ is methyl and $R^{10}$ is phenyl substituted with one trifluoromethyl group. In a particularly preferred embodiment thereof, the trifluoromethyl group is in the 4' position of the biphenyl group formed between $R^{10}$ and the phenyl to which it is attached.

The invention also relates to a compound of the formula AB1-e, wherein $R^2$-$R^{11}$ are as defined above for the compound AB1, and $L^e$ is a carboxylic acid ester. In an embodiment, the ester is an alkyl ester, preferably a (C$_1$-C$_6$) alkyl ester or a substituted-alkyl variation thereon. In a preferred embodiment, $L^e$ is the ethyl carboxylic acid ester, i.e., —C(O)OCH$_2$CH$_3$. In another preferred embodiment, $L^e$ is the methyl carboxylic acid ester, i.e., —C(O)OCH$_3$.

The invention also relates to process for preparing a compound of formula C.

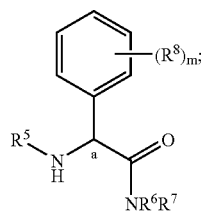

C or a stereoisomer thereof, which comprises reacting an amine of the formula HNR$^6$R$^7$ with a compound of the formula

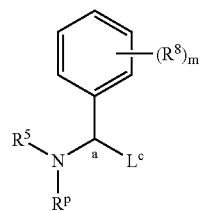

C' wherein $R^p$ is H or a protecting group.

In an embodiment, the protecting group is tert-butyloxycarbonyl ("BOC"). In another embodiment, the process comprises combining C' with a catalyst, e.g. HOBt, and a carbodiimide in a suitable solvent, and adding the amine HNR$^6$R$^7$. In a preferred embodiment, the carbodiimide is N,N'-dicyclohexylcarbodiimide. In another preferred embodiment, the carbodiimide is EDC. In another preferred embodiment, the suitable solvent is dichloromethane. In a preferred embodiment, the mixture of C', the amine HNR$^6$R$^7$, HOBt and carbodiimide is stirred for about 30 minutes to 24 hours before further processing. In an embodiment, the further processing comprises an aqueous work-up to provide the compound of formula C. In a preferred embodiment, the amine HNR$^6$R$^7$ is N-methylbenzylamine, i.e., $R^6$ is methyl and $R^7$ is benzyl. In another preferred embodiment, $R^p$ is BOC and the amine is N-methylbenzylamine, and in a more preferred embodiment thereof, the resulting compound of formula C, (tert-butyl (RS)-2-[benzyl(methyl)amino]-2-oxo-1-phenylethylcarbamate), is treated with trifluorocaetic acid and triethylsilane in dichloromethane, followed by aqueous workup to yield (RS)-N-benzyl-N-methyl-2-phenylglycinamide. In a particularly preferred embodiment, $R^p$ is BOC and the amine is N-methylbenzylamine, and in a more preferred embodiment thereof, the resulting optically enriched compound of formula C, (tert-butyl (S)-2-[benzyl(methyl)amino]-2-oxo-1-phenylethylcarbamate), is treated with concentrated hydrochloric acid in propan-2-ol, followed by advantageous precipitation of (S)-N-benzyl-N-methyl-2-phenylglycinamide hydrochloride monohydrate from mixtures of propan-2-ol and tert-butyl methyl ether, resulting in a useful increase in the degree of optical enrichment.

A salt of the phenylglycine amide may be prepared, e.g., by treating the amide, e.g., (RS)-N-benzyl-N-methyl-2-phenylglycinamide, with di(o-toluoyl)-L-tartaric acid in a suitable solvent, e.g. ethyl acetate, to provide the di(o-toluoyl)-L-tartrate) salt, e.g. (RS)-N-benzyl-N-methyl-2-phenylglycinamide. Tartrate salts of the phenylglycine amides may be broken to provide the amide, which may be purified as its hydrochloride salt.

In another embodiment, racemic compounds of the formula C may be resolved via the selective precipitation of one of the enatiomers as its salt with an optically enriched chiral acid, of which many examples are known in the art, from suitable solvents, e.g. methanol and ethanol. Such optically enriched chiral acids may be naturally occuring or synthetic. The precipitated salts may be hydrates or solvates.

In a preferred embodiment, (RS)-N-benzyl-N-methyl-2-phenylglycinamide is treated with di(o-toluoyl)-L-tartaric acid in methanol at 20° C. The precipitated salt is filtered and washed with methanol, then dried providing (S)-N-benzyl-N-methyl-2-phenylglycinamide di(o-toluoyl)-L-tartrate with 92.7% d.e. (chiral HPLC). This material is reslurried in hot methanol, filtered, washed and dried to providing (S)-N-benzyl-N-methyl-2-phenylglycinamide di(o-toluoyl)-L-tartrate with 99% d.e. (37% overall yield).

The diastereomericly enriched salts formed as described in the previous embodiments may be broken to provide optically enriched free amines C, e.g. (S)-N-benzyl-N-methyl-2-phenylglycinamide, which may be advantageously purified by crystallization as-is or by the formation of a salt with an achiral acid in the presence of suitable solvents, e.g. precipitation of (S)-N-benzyl-N-methyl-2-phenylglycinamide hydrochloride from mixtures of propan-2-ol and tert-butyl methyl ether.

In another embodiment, a racemic compound of the formula C may be resolved via the selective recrystallization of its salt with an optically enriched chiral acid, e.g. (RS)-N-benzyl-N-methyl-2-phenylglycinamide di(o-toluoyl)-L-tartrate prepared as described above, from a suitable solvent, to provide diastereomericly enriched salts, e.g. (S)-N-benzyl-N-methyl-2-phenylglycinamide di(o-toluoyl)-L-tartrate. Breakage of these salts delivers optically enriched free amines of the formula C, which may be advantageously isolated and used as the hydrochloride salt, e.g. (S)-N-benzyl-N-methyl-2-phenylglycinamide hydrochloride.

In another embodiment, where optically enriched compunds C are preferred, the unwanted enantiomer of the compound C may be recycled by racemization. In a more preferable embodiment, the racemization is applied to mother liquors from the resolutions described above by refluxing in the presence of a catalytic amount of a carbonyl compound, e.g. 2-chlorobenzaldehyde, thus allowing the isolation of second crops of diastereomerically enriched salts containing the desired enatiomer of compound C, e.g. (S)-N-benzyl-N-methyl-2-phenylglycinamide di(o-toluoyl)-L-tartrate with 92% d.e. in approximately 50% yield of the solute in the initial ethanolic mother liquors. In a still more preferred embodiment, the catalysed racemization is performed at a suitable temperature and concentration in-situ during the resolution in a suitable solvent, prior to the isolation of the first crop of product; this "dynamic resolution" allows a first crop yield of product to be significantly greater than the 50% available by traditional salt resolutions. Dynamic resoultions are known in the art, but are considered far from trivial and highly substrate dependent.

In still another embodiment of a process for preparing an opticaly enriched compound of formula C, a homochiral amino acid, e.g. (S)-L-2-phenylglycine, is converted to the corresponding N-carboxyanhydride, e.g. (S)-4-phenyl-1,3-oxazolidine-2,5-dione, using methods well known in the art, which, may then be combined an amine, e.g. N-methylbenzylamine. The resulting mixture is then subjected to an aqueous work-up, providing the optically enriched aminoamide, e.g. (S)-N-benzyl-N-methyl-2-phenylglycinamide, which may be purified as-is or as a suitable salt.

The invention also relates to a process for preparing a compound of formula 2 which comprises: (a) forming an amide linkage between a compound of the formula A and a compound of the formula B2:

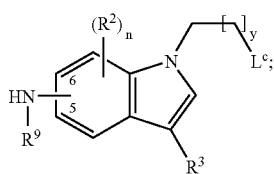

and (b) forming an amide linkage between the product of step (a) and a compound of the formula C; wherein $R^2$, $R^3$, $R^9$, $L^c$, y and A and C are as defined above.

The invention also relates to a process for preparing a compound of formula 2 which comprises forming an amide linkage between a compound of the formula AB2

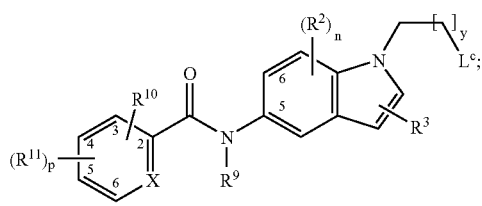

and a compound of the formula C; wherein $R^2$, $R^3$, $R^9$, $R^{10}$, $R^{11}$ and y are as defined above.

The invention also relates to a process for preparing a compound of formula 1b, wherein $X^1$ is S or O, which comprises: (a) forming an amide linkage between a compound of the formula AB3:

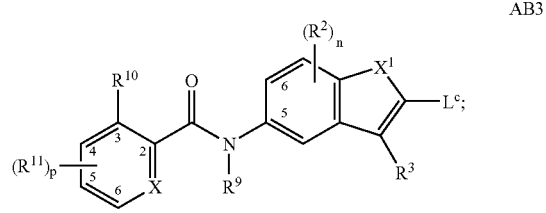

and a compound of the formula C, wherein $X^1$ is S or O, and (b) forming an amide linkage between the product of step (a) and a compound of the formula C, wherein the compound of formula A and the compound of formula C are as defined above.

The invention also relates to a process for preparing a compound of formula 1b, wherein $X^1$ is S or O, which comprises: (a) forming an amide linkage between a compound of the formula B3 and a compound of the formula C; and (b) forming an amide linkage between the product of step (a) and a compound of the formula A, wherein A, B3 and C are as defined above.

It is to be understood that the methods of preparing the compounds disclosed herein, including the compounds of formulas 1, 1b and 2, their varied embodiments and synthetic precursors or intermediates are not limiting but only illustrative.

The compounds of this invention are useful as MTP/ApoB inhibitors.

The terms "compound(s) of formula 1", "compound(s) of formula 1b", "compound(s) of formula 2", etc. include a compound of formula 1 (or 1b or 2, respectively) as defined herein and all of the embodiments, preferred embodiments, more preferred embodiments, and particularly preferred embodiments of such compounds, including the compounds named or exemplified herein, each of which is a particularly preferred embodiment of the compounds defined by the formulas. Reference to "a compound of the invention" is meant to encompass any of the compounds of formula 1, formula 1b or formula 2 as those terms are defined above. Accordingly, reference to "a compound of the invention" in connection with any of the embodiments, preferred embodiments, more preferred embodiments or particularly preferred embodiments of the compositions, processes and methods of the invention described herein, as well as embodiments relating to salts, polymorphs, solvates, hydrates, prodrugs and isotopically-labelled derivatives of the compounds of the invention, is intended to refer to any of the compounds of formula 1 (or 1b or 2 respectively) as defined above, i.e., to any of the embodiments, preferred embodiments, more preferred embodiments or particularly preferred embodiments of the compounds, especially the compounds named or exemplified herein.

This invention also relates to the salts, polymorphs, solvates and hydrates of the compounds of the invention, as well as to the salts, polymorphs, solvates and hydrates of the synthetic precursors of each of the compounds of the invention. The invention relates to polymorphs of the compound of formula 1, wherein $R^1$-$R^8$ are as defined above, having an X-ray powder diffraction patterns substantially the same as shown in any of FIGS. 1, 3, 4, and 5. It is to be understood that some level of noise is inherent in the generation of a diffraction pattern, i.e., peaks in intensity are to be discriminated from background according to methods well-known in the art. In a preferred embodiment, the compound is (S)-N{2-

[benzyl(methyl)amino]-2-oxo-1-phenylethyl}-1-methyl-5-[4'-(trifluoromethyl)[1,1'-biphenyl]-2-carboxamido]-1H-indole-2-carboxamide and the X-ray powder diffraction pattern is substantially the same as that shown in FIG. 1. In a more preferred embodiment, the compound has an X-ray powder diffraction pattern having peaks at 2-theta values substantially the same as the 2-theta values for at least ten of the peaks of highest intensity in the X-ray powder diffraction pattern shown in FIG. 1.

In an embodiment, the compound of the invention is a polymorph of the compound of formula 1 having a differential scanning calorimetry (DSC) profile substantially the same as that shown in FIG. 2. In a preferred embodiment, the compound is (S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide. In a more preferred embodiment, the compound exhibits a heat absorption onset temperature, peak temperature and characteristic shape substantially the same as that shown in FIG. 2.

The term "pharmaceutically acceptable salt(s)", as used herein, unless otherwise indicated, includes salts of acidic or basic groups that may be present in the compounds of the invention. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The compounds of the invention that are basic in nature are capable of forming a wide variety of salts with various inorganic and organic acids. The acids that may be used to prepare pharmaceutically acceptable acid addition salts of such basic compounds of the invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

The compounds of the invention that are acidic in nature, are capable of forming base salts with various pharmacologically acceptable cations. Examples of such salts include the alkali metal or alkaline earth metal salts and particularly, the sodium and potassium salts. This invention also encompasses pharmaceutical compositions containing, and methods of treating proliferative disorders or abnormal cell growth through administering, prodrugs of compounds of the invention. Compounds of the invention having free amino, amido, hydroxy or carboxylic groups can be converted into prodrugs. Prodrugs include compounds wherein an amino acid residue, or a polypeptide chain of two or more (e.g., two, three or four) amino add residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

In certain combination therapies with other lipid-lowering agents, such as those described hereinbelow, e.g., HMG CoA reductase inhibitors, HMG CoA synthetase inhibitors, ACAT inhibitors, squalene synthetase inhibitors, etc., a compound of the invention may further comprise a prodrug which comprises a compound of formula 1 in a hydrolyzable linkage to another anti-cancer agent. Di-ester linkages, for example, are particularly useful for this purpose, i.e., the prodrug is in the form $A^1$-C(O)O-$L^1$-(O)C-$A^2$, wherein $A^1$ and $A^2$ are the two agents, $L^1$ is a linker such as a methylene or other ($C_1$-$C_6$) alkylene group (alone or further comprising a phenyl or benzyl group). The two agents may both be a compound of the invention, or one may be another agent useful for treating, e.g., obesity, as described herein. See, e.g., U.S. Pat. No. 4,342,772—penicillins in di-ester linkages with β-lactamase inhibitors. Accordingly, a compound of the invention having an available carboxylic add group provides just one convenient means of producing combination prodrugs of the compound of the invention, which are encompassed by this invention. Typically, the acidic conditions of the gastrointestinal tract, or enzymes localized in the cells thereof cause the hydrolysis of the prodrug, releasing both agents.

Certain compounds of the invention have asymmetric centers and therefore exist in different enantiomeric forms. All optical isomers and stereoisomers of the compounds of the invention, and mixtures thereof, are considered to be within the scope of the invention. With respect to the compounds of the invention, this invention includes the use of a racemate, one or more enantiomeric forms, one or more diastereomeric forms, or mixtures thereof. Some of the compounds of the invention may also exist as tautomers, including, e.g., keto-enol tautomers. This invention relates to the use of all such tautomers and mixtures thereof.

Furthermore, some compounds may exhibit polymorphism. It is to be understood that the present invention encompasses any and all racemic, optically-active, polymorphic and stereoisomeric forms, or mixtures thereof, which form or forms possess properties useful in the treatment of the conditions noted hereinabove, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the conditions noted herein by the standard tests described hereinafter.

The subject invention also relates to isotopically-labelled compounds of the invention which are identical to those recited in formula 1, formula 1b and formula 2 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds of the invention and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by carrying out the procedures disclosed in the Schemes and/or in the Examples below, by substituting a readily available isotopically labelled reagent for a non-isotopically labelled reagent.

The following selected functional group definitions and examples thereof are employed throughout the instant specification and the appendant claims and are offered by way of illustration, and not by limitation.

The term "alkyl" means both straight and branched chain saturated hydrocarbon groups. Some examples of alkyl groups are methyl, ethyl, propyl, isopropyl, butyl, isobutyl, tert-butyl, pentyl and hexyl.

The term "cycloalkyl" means both straight and branched chain saturated hydrocarbon groups comprising at least one ring or cyclic structure, and unless otherwise specified, is monocyclic. Some examples of cycloalkyl groups include cyclopropyl, cyclobutyl, cyclopentyl and cyclohexyl. Some examples of cycloalkenyl groups include cyclopropenyl, cyclobutenyl, cyclopentenyl, cyclohexenyl and cycloheptenyl.

The term "bicycloalkyl" means both straight and branched chain saturated hydrocarbon groups, optionally containing one or more double or triple bonds, comprising at least two rings or cyclic structures, which cyclic structures may contain one or more common carbon atoms, i.e., encompasses bridged bicyclic and spiro-bicyclic groups. Bicycloalkyl groups preferably contain from 5 to 12 members, more preferably, from 6 to 10 members. Preferably, each ring of a bicycloalkyl group contains from 3 to 6 members. An example of a bicycloalkyl group is spiro[4.5]decyl. In this application, the term "bridged" when referring to any bicyclic group means that the two rings share at least two common atoms; the shared atoms are known in the art as "bridgehead" atoms. Spiro bicyclic groups, in contrast, are bicyclic groups whose two rings share only a single bridgehead atom. Some other examples of bicycloalkyl groups are norbornyl, norbornenyl, bicyclo[3.1.0]hexyl. Bicycloalkyl groups may be in any available conformation, e.g., cis, trans, endo, exo with respect to their linkage to other groups or with respect to their substituents.

The term "alkenyl" means both straight and branched chain unsaturated hydrocarbon groups containing at least two carbons. Some examples of alkenyl groups are ethenyl, propenyl and isobutenyl.

The term "alkynyl" means both straight and branched chain hydrocarbon groups containing at least one triple bond between two carbon atoms. Some examples of alknyl groups are ethynyl and propynyl, e.g., propyn-1-yl and propyn-2-yl and propyn-3-yl.

The term "alkoxy" means a straight or branched chain hydrocarbon group attached through an oxygen atom. Some examples of alkoxy groups are methoxy, ethoxy, propoxy, isopropoxy, butoxy, isobutoxy, pentoxy, hexoxy and heptoxy.

The term "acyl" means either a straight or branched chain hydrocarbon moiety attached through a carbonyl group. Some examples of acyl groups are acetyl, propionyl, butyryl and isobutyryl.

The terms "halogen" or "halo" mean fluoro, chloro, bromo, and iodo groups, unless specified otherwise.

The term "haloalkyl", as used herein, unless otherwise indicated, means an alkyl group substituted with one or more halo groups, on one or more carbon atoms. Preferably, the haloalkyl comprises 1 to 3 halo groups, such as a hydrocarbon comprising a dichloromethyl group, or a monohalosubstituted hydrocarbon.

The term "perfluoro", when used in conjunction with a specified hydrocarbon group, is meant to include a substituent wherein the individual hydrogen atoms thereof are substituted therefor with fluorine atoms, preferably, wherein all the individual hydrogen atoms thereof are substituted therefor with fluorine. Some examples of perfluoro groups are trifluoromethyl (perfluoromethyl), pentafluoroethyl (perfluoroethyl) and heptafluoropropyl (perfluoropropyl).

The term "alkoxycarbonyl" means an alkoxy group attached through a carbonyl group. Some examples of alkoxycarbonyl groups are methoxycarbonyl, ethoxycarbonyl, propoxycarbonyl, isopropoxycarbonyl and butoxycarbonyl.

The term "alkylthio" means an alkyl group attached through a sulfur atom. Some examples of alkylthio groups are methylthio, ethylthio, propylthio, isopropylthio, butylthio, isobutylthio, pentylthio and hexylthio.

The term "alkylamino" means an alkyl group attached through a nitrogen atom, wherein the nitrogen is unsubstituted, i.e., the group is alkyl-NH—. Some examples of alkylamino groups are methylamino, ethylamino, propylamino, isopropylamino, butylamino and isobutylamino.

The term "dialkylamino" means an alkylamino group wherein the nitrogen atom is substituted with two independent alkyl groups $R^a$ and $R^b$, i.e., —($R^aR^b$). Some examples of dialkylamino groups are dimethylamino, diethylamino, dipropylamino and di-isopropylamino as well as N-methyl-N'-ethylamino, N-ethyl-N'-propylamino and N-propyl-N'-isopropylamino.

Some examples of acyloxy groups include acetyloxy, propionyloxy, butyryloxy, and also include such radicals which incorporate a cyclic substituent such as benzoyloxy.

The term "haloalkoxy", as used herein, unless otherwise indicated, means an —O-haloalkyl group wherein "haloalkyl" is as defined above. An example of a haloalkoxy group is trifluoromethoxy.

The term "aryl", as used herein, unless otherwise indicated, means an organic radical derived from an aromatic hydrocarbon by removal of one hydrogen, such as phenyl or naphthyl. Aryl is most preferably phenyl. It is to be understood that a napthyl group may be bonded through any position, i.e., napth-1-yl, napth-2-yl, napth-3-yl, napth-4-yl.

The terms "heterocyclyl" and "heterocyclic", as used herein, unless otherwise indicated, mean non-aromatic (saturated or unsaturated) monocyclic and multicyclic groups containing one or more heteroatoms each selected from O, S and N, wherein each ring of a heterocyclic group has from 3 to 8 atoms. Preferably, heterocyclic groups of this invention are monocyclic or bicyclic.

Monocyclic heterocyclic groups include rings having only 4 atoms; preferably, monocyclic heterocyclic groups contain from 4 to 8 members, and more preferably, from 4 to 6 members, and most preferably, 5 or 6 members. An example of a 4-membered heterocyclic group is azetidinyl (derived from azetidine), an example of a 5-membered heterocyclic group is imidazolidinyl, and an example of a 6-membered heterocyclic group is piperidinyl. Other examples of monocyclic heterocyclic groups are pyrrolidinyl, tetrahydrofuranyl, tetrahydrothienyl, tetrahydropyranyl, tetrahydrothiopyranyl, morpholino, thiomorpholino, thioxanyl, piperazinyl, 1,2,3,6-tetrahydropyridinyl, pyrrolinyl, 2H-pyranyl, 4H-pyranyl, 1,4-dioxanyl, 1,3-dioxolanyl, 1,4-dithianyl, pyrazolinyl, pyrazolidinyl, dihydropyranyl, dihydrothienyl, dihydrofuranyl and imidazolinyl. Other examples of monocyclic heterocyclic groups include azacycloheptane and azacyclooctane. Preferred monocyclic heterocyclic groups are azetidinyl, pyrrolidinyl, piperidinyl and morpholino. Monocyclic heterocyclic groups may be referred to herein as "heteromonocyclyl."

Bicyclic heterocyclic groups may be referred to herein as "heterobicyclic" or "heterobicyclyl", both of which as used herein mean heterocyclic groups containing two rings, and encompass fused-ring bicyclic, bridged bicyclic and spiro-bicyclic groups. Heterobicyclic groups preferably contain from 5 to 12 members, more preferably, from 6 to 10 members. Preferably, each ring of a heterobicyclic group contains from 3 to 6 members. An example of a heterobicyclic group is 1,4-dioxaspiro[4.5]decyl. Some other examples of heterobicyclic groups include azabicyclohexyl, e.g., 3-azabicyclo[3.1.0]hexyl, azabicycloheptyl, e.g., 2-azabicyclo[2.2.1]heptyl and azabicyclooctyl.

The term "heteroaryl" as used herein means aromatic heterocyclic groups comprising from 5 to 12 atoms and containing one or more heteroatoms each selected from O, S and N, wherein each ring of the heteroaryl group contains from 3 to 8 atoms. Heteroaryl groups of this invention unless otherwise indicated may contain one ring or more than one ring, i.e., they may be monocyclic or multicyclic, for example bicyclic, so long as at least one ring in a multicyclic group is aromatic. Preferably, heteroaryl groups of this invention are monocyclic or bicyclic. Preferably, each ring of a heteroaryl group contains one or two heteroatoms. Monocyclic heteroaryl groups preferably contain from 5 to 8 members, more preferably, 5 or 6 members. Preferably, the monocyclic heteroaryl groups containing two heteratoms contain two nitrogen atoms, a nitrogen atom and an oxygen atom, or a nitrogen atom and a sulfur atom. Some examples of monocyclic heteroaryl groups are pyridinyl, imidazolyl, pyrimidinyl, pyrazolyl, triazolyl, pyrazinyl, tetrazolyl, furyl, thiophenyl (referred to hereinafter as "thienyl"), isoxazolyl, thiazolyl, oxazolyl, isothiazolyl, pyrrolyl, oxadiazolyl, thiadiazolyl and furazanyl (i.e., 2,5-diaza-furanyl). Preferred among the monocyclic heteroaryl groups are thienyl, furyl and pyridinyl. More preferred monocyclic heteroaryl groups are thien-2-yl, fur-2-yl, pyridin-2-yl, pyridin-3-yl, i.e., attached through the 2- or 3-carbon, respectively. A particularly preferred monocyclic heteroaryl group is pyridyl. The term "pyridyl" as used in this application, unless otherwise specified, means 2-pyridyl, 3-pyridyl or 4-pyridyl, i.e., pyridyl attached through any available carbon atom.

Multicyclic heteroaryl groups are preferably bicyclic; bicyclic heteroaryl groups preferably contain 9 or 10 members. Some examples of heteroaryl groups are quinolinyl, isoquinolinyl, indolyl, 3H-indolyl, indolinyl, benzimidazolyl, benzofuranyl, cinnolinyl, indazolyl, indolizinyl, phthalazinyl, pyridazinyl, triazinyl, isoindolyl, purinyl, benzofurazanyl, benzothiophenyl, benzothiazolyl, benzisothiazolyl, benzoxazolyl, pteridinyl, benzothiadiazine, benzothiazinyl, 2H-1-benzopyranyl, chromanyl, benzoxazolyl, quinazolinyl, quinoxalinyl, naphthyridinyl, and furopyridinyl.

The foregoing heterocyclic and heteroaryl groups may be C-attached or N-attached where such is possible. For instance, pyrrolyl may be pyrrol-1-yl (N-attached) or pyrrol-3-yl (C-attached). The heterocyclic groups of this invention also include ring systems substituted with one or more oxo moieties.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating, as "treating" is defined immediately above.

The invention further relates to a pharmaceutical composition comprising a compound of formula 1 and a pharmaceutically acceptable carrier. The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic add and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Exemplary parenteral administration forms include solutions or suspensions of active compounds in sterile aqueous solutions, for example, aqueous propylene glycol or dextrose solutions. Such dosage forms can be suitably buffered, if desired. Aqueous compositions of the present invention may comprise other pharmaceutically acceptable solutes including additives and other therapeutic agents, as appropriate. Suitable additives are those well known in the art including, but not limited to, antioxidants, antibacterials, surfactants, chelating agents, sugars, and preservatives. Aqueous compositions of the invention can be administered by injection, which can be intramuscular, intravenous or preferably subcutaneous. A dose of from about 0.5 µg/Kg/day to about 10 µg/Kg/day, preferably from about 1 µg/Kg/day to 5 µg/Kg/day, can be used.

Methods of preparing various pharmaceutical compositions with a specific amount of active compound are known, or will be apparent, to those skilled in this art. For examples, see *Remington: The Practice of Pharmacy, Lippincott Williams and Wilkins, Baltimore Md., 20th ed. 2000.*

The compounds of the invention can be administered alone but will generally be administered in an admixture with suitable pharmaceutical excipient(s), diluent(s) or carrier known in the art and selected with regard to the intended route of administration and standard pharmaceutical practice. If appropriate "auxiliary" agents may also be added, which includes preservatives, anti-oxidants, flavors or colorants. The compound of the invention may be formulated to provide immediate-, delayed-, modified-, sustained-, pulsed- or controlled-release dependent on the specific route of administration and the specificity of release profile, commensurate with therapeutic needs.

The compounds of the invention can be administered, for example but not limited to, the following route: oral (including buccal, sublingual, etc.) in the forms that are well known in the art (ref.) for veterinary and pharmaceutical applications. "Oral" in this instance refers to oral mode of administration wherein the forms are explicitly provided to the animals for oral consumption i.e., on-diet, in-drinking fluid, placed directly into the oral cavity, or offered for free-choice consumption. In this invention, the term "animal" includes a warm-blooded animal of the animal kingdom possessed of a homeostatic mechanism and includes mammals and birds, preferably companion animals and livestock animals, and humans. Some examples of companion animals are canines, e.g., dogs, felines, e.g., cats and horses; some examples of livestock animals are pigs, cows, sheep and the like. Preferably, the animal is a mammal. More preferably, the mammal is a companion animal or a livestock animal.

Typical oral solid forms may include tablets, powders, multi-particulate preparations (granules), capsules, chews, lozenges, films, patches, etc. Typical oral liquid (including semi-solid and colloidal) forms may include solutions, elixirs, gels, sprays, liquid-filled chews, etc. Other oral forms wherein the active agent is suspended in a liquid or semi-solid carrier phase, for example suspensions, may also be used.

The preferred oral solid, liquid and suspension forms for a compound of the invention are those that impart flexibility in dosing to the animals, wherein the method of administration is facile and the dose can be accurately and flexibly controlled in keeping with the need of the therapy. Examples of such forms include tablet preparations, solutions (and similar forms thereof as described herein) and suspensions. In these examples, the dose can be easily controlled for oral administration. Particularly for solutions and suspensions, the utility of appropriate metering systems (i.e., calibrated syringes etc.) provides high flexibility in controlling the dose to facilitate administration to animal species of different sizes or to different animal species or breeds, with varying dose requirements. Additionally, the utility of flavoring/palatability agents and/or texture enhancers in the said forms can promote animal acceptance and compliance, which can be particularly advantageous when dosing chronically to animals.

The compounds of the invention may also be administered via the parenteral routes. The term parenteral in this context refers to all routes of drug administration that is not via the oral cavity. Preferably for the compounds of the innovation, parenteral routes may include topical and transdermal, rectal, vaginal, nasal, inhalation and injectables (i.e., administration modes that require penetration of the skin barrier via needle and needle-less methods, including implants and reservoirs). Formulations for these routes of administration may be prepared in a conventional manner in accordance with standard pharmaceutical and veterinary practices, illustrative examples of which are described herein.

Particularly preferred compositions of the compounds of the invention comprise oral solid forms, examples of which are provided below, are preferably tablets, powders or granules which typically contain just the active agent(s) or preferably in combination with adjuvants/excipients.

In an embodiment of the invention, the pharmaceutical composition comprises a compound the invention, herein referred to also as "the active" in an amount typically less than 50% (by weight) of the formulation and preferably less than 10%, more preferably, about 2.5% by weight, and a pharmaceutically acceptable carrier. In a preferred embodiment, the predominant portion of the formulation comprises fillers, diluents, disintegrants, lubricants and optionally, flavors. The composition of these excipients is well known in the art. In an embodiment of the invention, the preferred fillers/diluents comprise admixtures of two or more of the following components: avicel, mannitol, lactose (all types), starch, and di-calcium phosphate. In preferred embodiments of the compositions, the filler/diluent admixtures typically comprises less than 98% (by weight) of the formulation and preferably less than 95%, for example 93.5%. In a preferred embodiment, disintegrants include Ac-di-sol, Explotab™, starch and sodium lauryl sulphate (SLS)—also known as wetting agent. In a more preferred embodiment, the amount of filler/diluent admixture usually comprises less than 10% (by weight) of the composition and preferably less than 5%; in a particularly preferred embodiment, the amount is about 3%. In a particularly preferred embodiment, the lubricant is magnesium stearate. In preferred embodiments thereof, the magnesium stearate is present in an amount less than about 5% of the formulation and preferably less than about 3%, more preferably, about 1%. Preferably, lubricants comprise less than 60% of the formulation, preferably less than 40%, and most preferably, from about 10% to about 20%. Particularly preferred embodiments of tablet formulations for the compounds of the invention are shown in Table 10.

The compositions of the invention include tablets. In a preferred embodiment, tablets are manufactured by a process selected from direct compression or a wet, dry or melt granulation, melt congealing process and extrusion. In another embodiment, tablet cores of the compositions of the invention may be mono or multi-layer(s) and can be coated with appropriate overcoats known in the art.

Oral liquid forms of the compounds of the invention are preferably solutions, wherein the active compound is fully dissolved. In an embodiment, the solution comprises the active and a pharmaceutically precedented solvents suitable for oral administration. In a preferred embodiment, the solvent is one in which the compounds of the invention show good solubility. In a more preferred embodiment, the solution comprises a solvent selected from polyethylene glycol, polypropylene glycol, edible oils and glyceryl- and glyceride-based systems. In more preferred embodiments, glyceryl- and glyceride-based systems comprise agents selected from Captex 355 EP, Crodamol GTC/C, or Labrafac CC, triacetin, Capmul CMC, Migyols (812, 829, 840), Labrafil M1944CS, Peceol and Maisine 35-1. The exact composition of these agents and commercial sources are shown in Table 11. These solvents usually make up the predominant portion of the formulation i.e., greater than 50% (by weight) and preferably greater than 80%, for example 95% and more preferably greater than 99%. In preferred embodiments, the solution further comprises an adjuvant or additives. In a preferred embodiment thereof, the additive or adjuvant is a taste-mask agent, palatability agent, flavoring agent, antioxidant, stabilizer, texture modifier, viscosity modifier, or a solubilizer.

A further embodiment is a process for preparing preferred oral liquid form of the compounds of the invention (see the Pharmaceutical Compositions section), wherein the individually preferred components are combined optionally with mechanical or ultrasonic agitation in a preferred temperature range, in such a fashion that is advantageous to the rate of dissolution.

The compounds of the instant invention inhibit or decrease Apo B secretion, likely by the inhibition of MTP, although it may be possible that other mechanisms are involved. The compounds are useful in treating any of the disease states or conditions in which Apo B, serum cholesterol, and/or triglyceride levels are elevated. Thus, the compositions of this invention are useful for the treatment of conditions including atherosclerosis, pancreatitis, obesity, hypercholesterolemia, hypertriglyceridemia, hyperlipidemia and diabetes. Accordingly, this invention provides pharmaceutical compositions comprising a therapeutically effective amount of a compound of the invention, including the stereoisomers, pharmaceutically acceptable salts and solvates thereof, in combination with a pharmaceutically acceptable carrier or diluent.

The instant invention also relates to a method for inhibiting or decreasing Apo B secretion in an animal in need thereof which comprises the administration of an Apo B secretion inhibiting or decreasing amount of a compound of the invention or a stereoisomer, pharmaceutically acceptable salt or solvate thereof. The invention further provides a method of treating a condition selected from atherosclerosis, pancreatitis, obesity, hypercholesterolemia, hypertriglyceridemia, hyperlipidemia, and diabetes which comprises administering to an animal in need of such treatment a therapeutically effective amount of a compound of formula 1 (or 1b or 2) or a stereoisomer, pharmaceutically acceptable salt or solvate thereof. A preferred subgroup of the conditions described hereinabove is atherosclerosis, obesity, hypercholesterolemia, hypertriglyceridemia, hyperlipidemia, and diabetes.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

Diabetes can be treated by administering to an animal having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the invention along with other agents that can be used to treat diabetes. Preferably, the diabetes is Type II diabetes. More preferably, the animal is feline; even more preferably, the feline is a cat.

Accordingly, this invention further relates to a method of treating Type II diabetes in an animal in need of such treatment, which comprises administering to the animal a therapeutically effective amount of a compound of formula 1 or a stereoisomer, pharmaceutically acceptable salt or solvate thereof.

The invention also provides a method of treating Type II diabetes in an animal in need of such treatment, which comprises administering to the animal a therapeutically effective amount of a compound of formula 1 or a stereoisomer, pharmaceutically acceptable salt or solvate thereof, in combination with one or more additional agents capable of treating Type II diabetes in the animal.

Representative agents that can be used to treat diabetes include insulin and insulin analogs (e.g. LysPro insulin); GLP-1 (7-37) (insulinotropin) and GLP-1 (7-36)-$NH_2$; sulfonylureas and analogs: chlorpropamide, glibenclamide, tolbutamide, tolazamide, acetohexamide, Glypizide®, glimepiride, repaglinide, meglitinide; biguanides: metformin, phenformin, buformin; $\alpha 2$-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir, $\alpha$-glucosidase inhibitors: acarbose, miglitol, emiglitate, voglibose, MDL-25,637, camiglibose, MDL-73,945; $\beta$-agonists: BRL 35135, BRL 37344, Ro 16-8714, ICI D7114, CL 316,243; phosphodiesterase inhibitors: L-386,398; lipid-lowering agents: benfluorex; antiobesity agents: fenfluramine and orlistat; vanadate and vanadium complexes (e.g. Naglivan®) and peroxovanadium complexes; amylin antagonists; glucagon antagonists; gluconeogenesis inhibitors; somatostatin analogs; antilipolytic agents: nicotinic acid, acipimox, WAG 994; and glycogen phosphorylase inhibitors, such as those disclosed in WO 96/39385 and WO 96/39384. Also contemplated in combination with compounds of the invention are pramlintide acetate (Symlin™) and nateglinide. Any combination of agents can be administered as described above.

The invention also relates to a method of treating obesity in a mammal which comprises administering to an animal in need of such treatment an effective amount of an intestinal-MTP-selective compound, wherein the $ED_{25}$ of the compound for the inhibition of intestinal fat absorption is at least 5-fold lower than the $ED_{25}$ of the compound for the lowering of serum triglycerides. In an embodiment, the $ED_{25}$ for the inhibition of intestinal fat absorption is at least 10-fold lower than the $ED_{25}$ of the compound for the lowering of serum triglycerides. In another embodiment, the compound exhibits an $ED_{25}$ for the inhibition of intestinal fat absorption which is at least 50-fold lower than the $ED_{25}$ of the compound for the lowering of serum triglycerides.

In another embodiment, the intestinal-MTP-selective compound is a compound of formula 1, 1b or 2, or an embodiment, preferred embodiment, more preferred embodiment, or particularly preferred embodiment of a compound of formula 1, 1b or 2.

In this invention, the term "selectivity" refers to a greater effect of a compound in a first assay, compared to the effect of the same compound in a second assay. In the above embodiment of the invention, the first assay is for the ability of the compound to inhibit intestinal fat absorption and the second assay is for the ability of the compound to lower serum triglycerides. In a preferred embodiment, the ability of the compound to inhibit intestinal fat absorption is measured by the $ED_{25}$ of the compound in an intestinal fat absorption assay, such that a greater effect of the compound results in the observation of a lower absolute (numerical) value for the $ED_{25}$. In another preferred embodiment, the ability of the compound to lower serum triglycerides is measured by the $ED_{25}$ of the compound in a serum triglyceride assay. Again, a greater effect of a compound in the serum triglyceride lowering assay results in the observation of a lower absolute (numerical) value for the $ED_{25}$. An illustrative example of each assay is provided hereinbelow, but it is to be understood that any assay capable of measuring the effectiveness of a compound in inhibiting intestinal fat absorption, or capable of measuring the effectiveness of a compound in lowering serum triglycerides, is encompassed by the present invention.

In a particularly preferred embodiment, the intestinal-MTP-selective compound is a compound of formula 1b, wherein $X^1$ is $N(R^4)$ or O, $X^2$ is C(H); m, n and p are all 0; $R^3$ is H or Cl; $R^4$ is $CH_3$; $R^5$ and $R^9$ are both H; $R^{10}$ is phenyl (with carbons numbered 1'-6') substituted at the 4'-position with $CF_3$, or $R^{10}$ is $(C_1$-$C_6)$alkoxy; $R^6$ is H or methyl and $R^7$ is $(C_1$-$C_6)$alkyl or benzyl, wherein the benzyl is optionally substituted with $(C_1$-$C_6)$alkyl or $(C_1$-$C_6)$alkoxy.

The compounds of this invention may be used in conjunction with other pharmaceutical agents, including other lipid lowering agents. Such agents include, for example, cholesterol biosynthesis inhibitors and cholesterol absorption inhibitors, especially HMG-CoA reductase inhibitors and HMG-CoA synthase inhibitors; HMG-CoA reductase gene expression inhibitors; CETP inhibitors; bile acid sequestrants; fibrates; cholesterol absorption inhibitors; ACAT inhibitors, squalene synthetase inhibitors, ion-exchange resins, anti-oxidants and niacin. In combination therapy treatment, the compounds of the instant invention and the other drug therapies may be administered to animals (e.g. humans) by conventional methods.

This invention provides a method of treating atherosclerosis; pancreatitis secondary to hypertriglyceridemia; hyperglycemia (1) by causing a reduced absorption of dietary fat through MTP inhibition, (2) by lowering triglycerides through MTP inhibition or (3) by decreasing the absorption of free fatty acids through MTP inhibition; in an animal in need of treatment thereof, which comprises administering to the animal a therapeutically effective amount of the compound of formula 1, 1b or 2.

The invention also provides a pharmaceutical composition comprising: a) a therapeutically effective amount of a first compound, wherein said first compound is a compound of claim 1 or a stereoisomer, pharmaceutically acceptable salt or hydrate thereof; b) a therapeutically effective amount of a second compound, wherein said second compound is selected from a cholesterol absorption inhibitor, a CETP inhibitor, an HMG-CoA reductase inhibitor, an HMG-CoA synthase inhibitor, an inhibitor of HMG-CoA reductase gene expression, niacin, an antioxidant, an ACAT inhibitor or a squalene synthetase inhibitor; and c) a pharmaceutically acceptable carrier or diluent. In a preferred embodiment of the invention, the said second compound is selected from lovastatin, simvastatin, pravastatin, fluvastatin, atorvastatin or rivastatin. In a more preferred embodiment of the invention, said second compound is atorvastatin.

Specific cholesterol absorption inhibitors and cholesterol biosynthesis inhibitors are described in detail hereinbelow. Additional cholesterol absorption inhibitors are known to those skilled in the art and are described, for example, in PCT WO 94/00480.

Any HMG-CoA reductase inhibitor may be employed as the second compound in the combination therapy aspect of the instant invention. The term HMG-CoA reductase inhibitor refers to a compound which inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., Methods of Enzymology, 1981; 71: 455-509 and the references cited therein). A variety of these compounds are described and referenced hereinbelow. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Additionally, U.S. Pat. No. 4,739,073 (the disclosure of which is hereby incorporated by reference) discloses certain substituted indoles, such as fluvastatin. Further, U.S. Pat. No. 4,346,227 (the disclosure of which is hereby incorporated by reference) discloses ML-236B derivatives, such as pravastatin. In addition, EP 491,226 teaches certain pyridyldihydroxyheptenoic acids, such as rivastatin. Also, U.S. Pat. No. 4,647,576 (the disclosure of which is hereby incorporated by reference) discloses certain 6-[2-(substituted-pyrrol-1-yl)alkyl]-pyran-2ones such as atorvastatin. Other HMG-CoA reductase inhibitors will be known to those skilled in the art.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art ac cording to standard assays (e.g., Methods of Enzymology, 1975; 35: 155-160 and Methods of Enzymology, 1985; 110: 19-26 and the references cited therein). A variety of these compounds are described and referenced hereinbelow. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing the microorganism MF5253. U.S. Pat. No. 4,847,271 (the disclosure of which is hereby incorporated by reference) discloses certain oxetane compounds such as 11-(3hydroxymethyl-4-oxo-2-oxetayl)-3,5,7-trimethyl-2,4-undecadienoic acid derivatives. Other HMG-CoA synthase inhibitors will be known to those skilled in the art.

Any compound that decreases HMG-CoA reductase gene expression may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein.

Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (Methods of Enzymology, 1985; 110: 9-19). Several such compounds are described and referenced below however other inhibitors of HMG-CoA reductase gene expression will be known to those skilled in the art U.S. Pat. No. 5,041,432 (the disclosure of which is incorporated herein by reference) discloses certain 15-substituted lanosterol derivatives. Other oxygenated sterois that suppress the biosynthesis of HMG-CoA reductase are discussed by E.I. Mercer (Prog. Up. Res., 1993; 32: 357-416).

Any compound having activity as a CETP inhibitor can serve as the second compound in the combination therapy aspect of the instant invention. The term CETP inhibitor refers to compounds which inhibit the cholesteryl ester transfer protein (CETP) mediated transport of various cholesteryl esters and triglycerides from high density lipoprotein (HDL)

to low density lipoprotein (LDL) and very low density lipoprotein (VLDL). A variety of these compounds are described and referenced hereinbelow however other CETP inhibitors will be known to those skilled in the art U.S. Pat. No. 5,512,548 (the disclosure of which is incorporated herein by reference) discloses certain polypeptide derivatives having activity as CETP inhibitors, while certain CETP-inhibitory rosenonolactone derivatives and phosphate-containing analogs of cholesteryl ester are disclosed in J. Antibiot., 1996; 49(8): 815-816, and Bioorg. Med. Chem. Lett; 1996; 6: 1951-1954, respectively.

Any ACAT inhibitor can serve as the second compound in the combination therapy aspect of this invention. The term ACAT inhibitor refers to compounds which inhibit the intracellular esterification of dietary cholesterol by the enzyme acyl CoA:cholesterol acyltransferase. Such inhibition may be determined readily by one of skill in the art according to standard assays, such as the method of Heider et al. described in Journal of Lipid Research., 1983; 24: 1127. A variety of these compounds are described and referenced hereinbelow however other ACAT inhibitors will be known to those skilled in the art.

U.S. Pat. No. 5,510,379 (the disclosure of which is incorporated by reference) discloses certain carboxysulfonates, while WO 96/26948 and WO 96/10559 both disclose urea derivatives having ACAT inhibitory activity.

Any compound having activity as a squalene synthetase inhibitor can serve as the second compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (Methods of Enzymology 1969; 15: 393-454 and Methods of Enzymology 1985; 110: 359-373 and references cited therein). A summary of squalene synthetase inhibitors has been complied (Curr. Op. Ther. Patents (1993) 861-4). European patent application publication No. 0 567 026 A1 discloses certain 4,1-benzoxazepine derivatives as squalene synthetase inhibitors and their use in the treatment of hypercholesterolemia and as fungicides. European patent application publication No. 0 645 378 A1 discloses certain seven- or eight-membered heterocycles as squalene synthetase inhibitors and their use in the treatment and prevention of hypercholesterolemia and fungal infections. European patent application publication No. 0 645 377 A1 discloses certain benzoxazepine derivatives as squalene synthetase inhibitors useful for the treatment of hypercholesterolemia or coronary sclerosis. European patent application publication No. 0 611 749 A1 discloses certain substituted amino acid derivatives useful for the treatment of arteriosclerosis. European patent application publication No. 0 705 607 A2 discloses certain condensed seven- or eight-membered heterocyclic compounds useful as antihypertriglyceridemic agents. PCT publication WO96/09827 discloses certain combinations of cholesterol absorption inhibitors and cholesterol biosynthesis inhibitors including benzoxazepine derivatives and benzothiazepine derivatives. European patent application publication No. 0 071 725 A1 discloses a process for preparing certain optically-active compounds, including benzoxazepine derivatives, having plasma cholesterol and triglyceride lowering activities.

The present invention also provides a method of treating obesity in an animal, which comprises administering to the obese animal a compound of this invention in combination with another anti-obesity agent.

The other anti-obesity agents is preferably selected from the group consisting of a $\beta_3$-adrenergic receptor agonist, a cholecystokinin-A (CCK-A) agonist, a monoamine reuptake inhibitor (such as sibutramine), a sympathomimetic agent, a serotoninergic agent (such as fenfluramine or dexfenfluramine), a dopamine agonist (such as bromocriptine), a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor (such as orlistat), a bombesin agonist, a neuropeptide-Y antagonist such as NPY-1 or NPY-5, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor such as Axokine, or a human agouti-related protein (AGRP) antagonist. Other anti-obesity agents are also known, or will be apparent in light of this disclosure, to one of ordinary skill in the art.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R) hydroxyethylamino)ethoxy]phenoxy}acetic acid.

In preferred embodiments, the additional anti-obesity agent is another MTP/apoB inhibitor selected from the group consisting of (i) BMS-197636, also known as 9-[4-[4-(2,3-dihydro-1-oxo-1H-isoindol-2-yl)-1-piperidinyl]butyl]-N-propyl-9H-fluorene-9-carboxamide; (ii) BMS-200150, also known as 2-[1-(3,3-diphenylpropyl)-4-piperidinyl]-2,3-dihydro-1H-isoindol-1-one; and (iii) BMS 201038, also known as 9-[4-(4-[2-(4-trifluoromethylphenyl)benzoylamino]piperidin-1-yl)butyl]-N-2,2,2-trifluoroethyl)-9H-fluorene-9-carboxamide; and the pharmaceutically acceptable salts of (i), (ii) and (iii). In another embodiment, the anti-obesity agent is selected from the agents disclosed in European patent application publication Nos. 0 584 446 A2 and 0 643 057 A1, the latter of which discloses certain compounds of the formulas

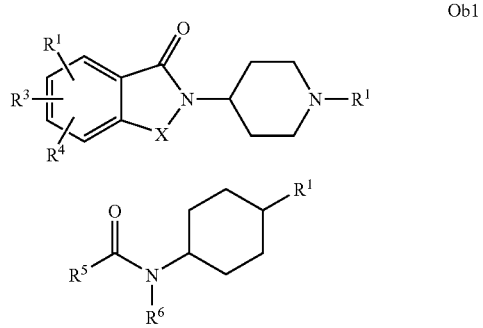

Ob1

-continued

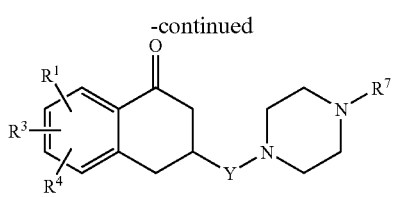

which have utility as inhibitors of MTP, wherein the substituents listed in formula Ob1 are as defined in EP 0 643 057 A1. In another embodiment, the anti-obesity agent is selected from the agents disclosed in European patent application publication Nos. 1 099 439 A2, which discloses certain compounds of the formula

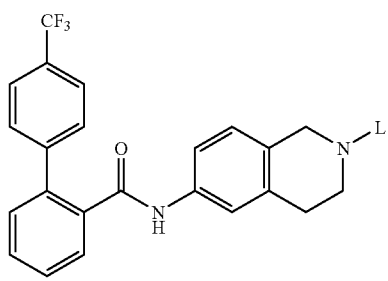

Ob2 wherein L in formula Ob2 is as defined as in EP 1 099 439 A2.

Preferred compounds of those disclosed in 1 099 439 A2 are compounds selected from the group consisting of 4'-trifluoromethyl-biphenyl-2-carboxylic acid-(2-butyl-1,2,3,4-tetrahydroisoquinolin-6-yl)-amide and 4'-trifluoromethyl-biphenyl-2-carboxylic acid-(2-(2-acetylaminoethyl)-1,2,3,4-tetrahydroisoquinolin-6-yl)-amide.

Methods for preparing the above agents are publicly available; for example, phentermine may be prepared as described in U.S. Pat. No. 2,408,345; sibutramine may be prepared as in U.S. Pat. No. 4,929,629; orlistat may be prepared as in U.S. Pat. No. 4,598,089; fenfluramine and dexfenfluramine may be prepared as described in U.S. Pat. No. 3,198,834; bromocriptine may be prepared as described in U.S. Pat. Nos. 3,752,814 and 3,752,888; and the substituted amino pyridines listed above may be prepared as described in PCT International Publication No. WO 96/35671; the disclosure of each of these publications is herein incorporated by reference.

It will be appreciated by those skilled in the art that certain compounds of the instant invention may contain an asymmetrically-substituted carbon atom and accordingly may exist in, and/or be isolated in, optically-active and racemic forms. Furthermore, some compounds may exhibit polymorphism. It is to be understood that the present invention encompasses any and all racemic, optically-active, polymorphic and stereoisomeric forms, or mixtures thereof, which form or forms possess properties useful in the treatment of the conditions noted hereinabove, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the conditions noted herein by the standard tests described hereinafter.

The present invention may be understood more fully by reference to the detailed description and illustrative examples, which are intended to exemplify non-limiting embodiments of the invention. The term "compound of formula 1", "compound of formula 2," as used herein, e.g., "a pharmaceutical composition comprising a compound of formula 1 . . . " encompasses in addition to their generic description of the compound, all of the embodiments, preferred embodiments, more preferred embodiments and particularly preferred embodiments of the compounds, as well as each of the Examples described below.

DETAILED DESCRIPTION OF THE INVENTION

Figure 1:
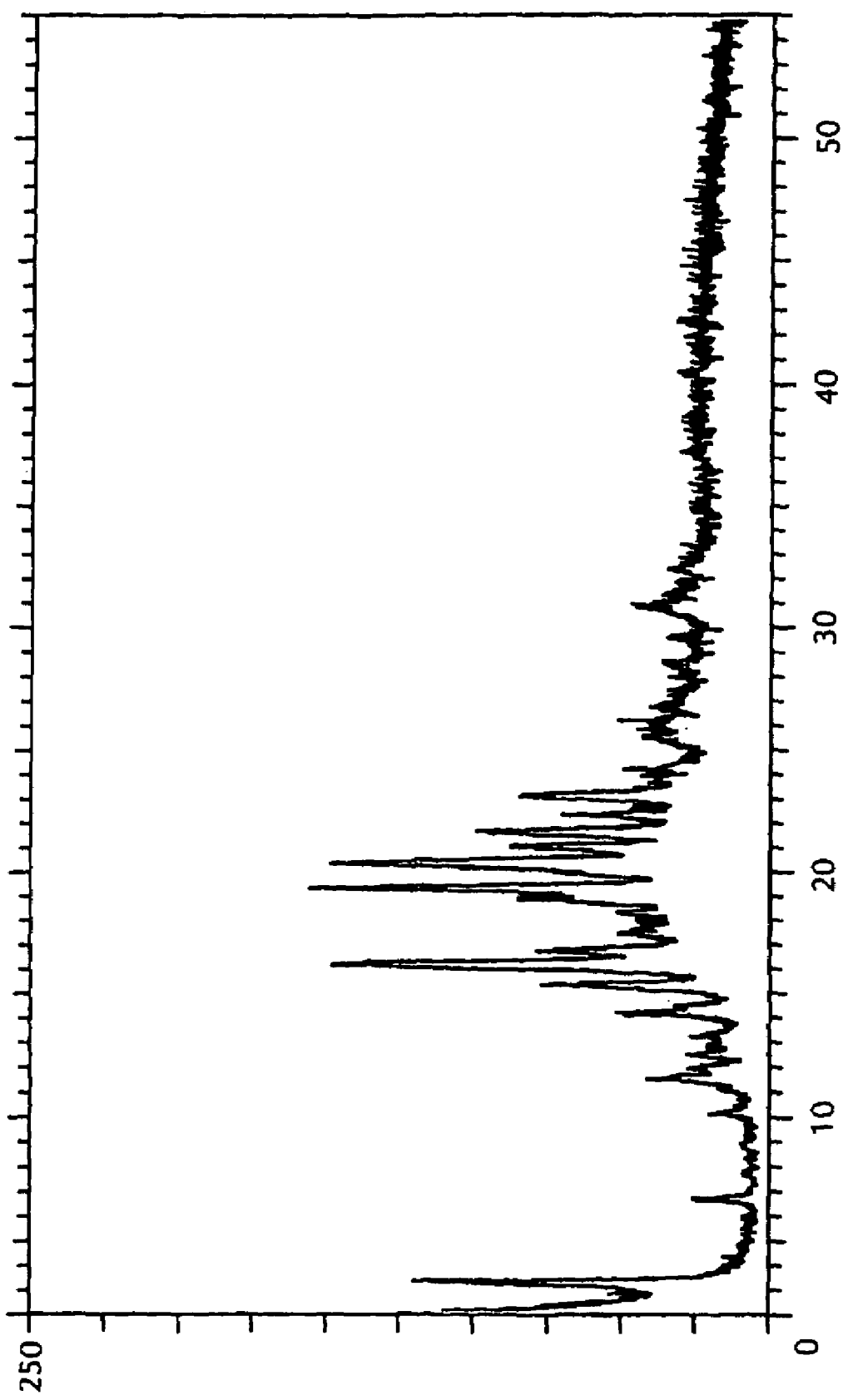
FIG. 1 shows the X-ray powder diffraction pattern of a sample of preferred Form A of the title compound described in Example 44. Detailed conditions for the preparation of the sample are provided in Example 44. The pattern was obtained on a Siemens D5000, Cu anode, variable slit, range 2-55, step size: 0.02; ambient temperature.

The following examples illustrate the compositions and methods of the present invention. It is to be understood that the present invention is not limited to the specific details of the Examples provided below.

In the discussion which follows, certain common chemical and procedural abbreviations and acronyms therefor have been employed which include: Me (methyl); Et (ethyl); EtOAc (ethyl acetate); Bn (benzyl); THF (tetrahydrofuran); DMF (dimethylformamide); BOC (tert-butyloxycarbonyl, a protecting group); DMAP (1,1'-dimethylaminopyridine), Ms (methanesulfonyl, mesyl); DIEA (diisopropylethylamine); TFA (trifluoroacetic acid); DIBAL (diisobutylaluminum hydride); PyBroP (Bromo-tris-pyrrolidino-phosphonium hexafluorophosphate); DEAD (Diethyl azodicarboxylate); Ac (acetyl); eq. (equivalent); RP (reverse phase); HPLC (high performance liquid chromatography); TLC (thin layer chromatography). Unless otherwise specified, "water" in the following descriptions means water which is deionized (also known as "demineralized") or of higher purity, e.g., deionized-distilled or deionized-multiply-distilled water. Preferably all materials will be of at least USP grade.

The compounds of formula 1, 2 and 3 are most conveniently synthesized by employing procedures analogous to those known in the chemical arts for the production of similar compounds. Exemplary processes for the manufacture of compounds of formula 1 2 and 3 as defined in detail hereinabove are provided as further features of the invention and are illustrated by the following procedures in which the meanings of generic radicals are as previously defined unless otherwise qualified. Examples of methods of preparing compounds of the present invention as described herein are provided by Schemes 1-3 below and the description that follows. In the following Schemes, unless otherwise indicated, substituents $R^1$-$R^{15}$, $R^a$-$R^c$, L, X, $Z^1$ and $Z^2$ are as defined above.

The compounds of formulas 1, 2 and 3 are generally prepared by forming amide linkages between the groups A, B and C shown in Table 1 below, wherein in compounds of formula 1, B is B1; in compounds of formula 2, B is B2; and in compounds of formula 3, B is B3; wherein $L^c$ is a carboxylic acid or an activated form thereof as described further below, and the amide linkages are formed between the $L^c$ group of A and the amino group —$NHR^9$, and between the $L^c$ group of B and the amine —$NHR^5$ of C, respectively It will be appreciated by those of skill in the art that there are many well-known methods of forming amide linkages, and that it is generally not important which amide linkage is formed first. Also, it will be appreciated by those of skill in the art that the groups A, B and C are either commercially available or can readily be prepared using materials and methods which are well-known in the art, as well as by the methods and procedures described herein. For example, compounds comprising the group A wherein X is $C(R^c)$ and $R^{10}$ is phenyl are commercially available, e.g., 2-biphenylcarboxylic acid, 4'-(methyl)-2-biphenylcarboxylic acid and 4'-(trifluoromethyl)-2-biphenylcarboxylic acid. In addition, numerous pyridyl-phenyl (X is N and $R^{10}$ is phenyl) and bipyridyl (X is N and $R^{10}$ is pyridyl) compounds are also readily obtained. Compounds of group B are readily formed from commercially available indoles (B1, B2), benzo[b]furans (B3) or benzo[b]thiophenes (B3), as well as by the methods and procedures described herein. Compounds of group C are readily prepared from commercially available phenyl glycines, wherein the carbamoyl moiety $C(O)NR^6R^7$ is formed between the carboxylic acid group of the phenylglycine and the amine $NR^6R^7$. Exemplary procedures for forming each of these groups and the amide linkages between them are provided in detail below. The Schemes which follow provide examples of various methods of forming the compounds of formulas 1, 2 and 3 using the synthetic precursors discussed above.

TABLE 1

| A | B | C |
|---|---|---|
| ![A structure with $R^{10}$, X, $L^c$, $(R^{11})_p$] | ![B1 structure with $(R^2)_n$, $R^4$, $L^c$, $R^3$, HN-$R^9$] "B1" | ![C structure with $(R^8)_m$, $R^5$NH, $NR^6R^7$] |
| | ![B2 structure with $(R^2)_n$, $L^c$, $R^3$, HN-$R^9$] "B2" | |
| | ![B3 structure with $(R^2)_n$, O/S, $L^c$, $R^3$, HN-$R^9$] "B3" | |

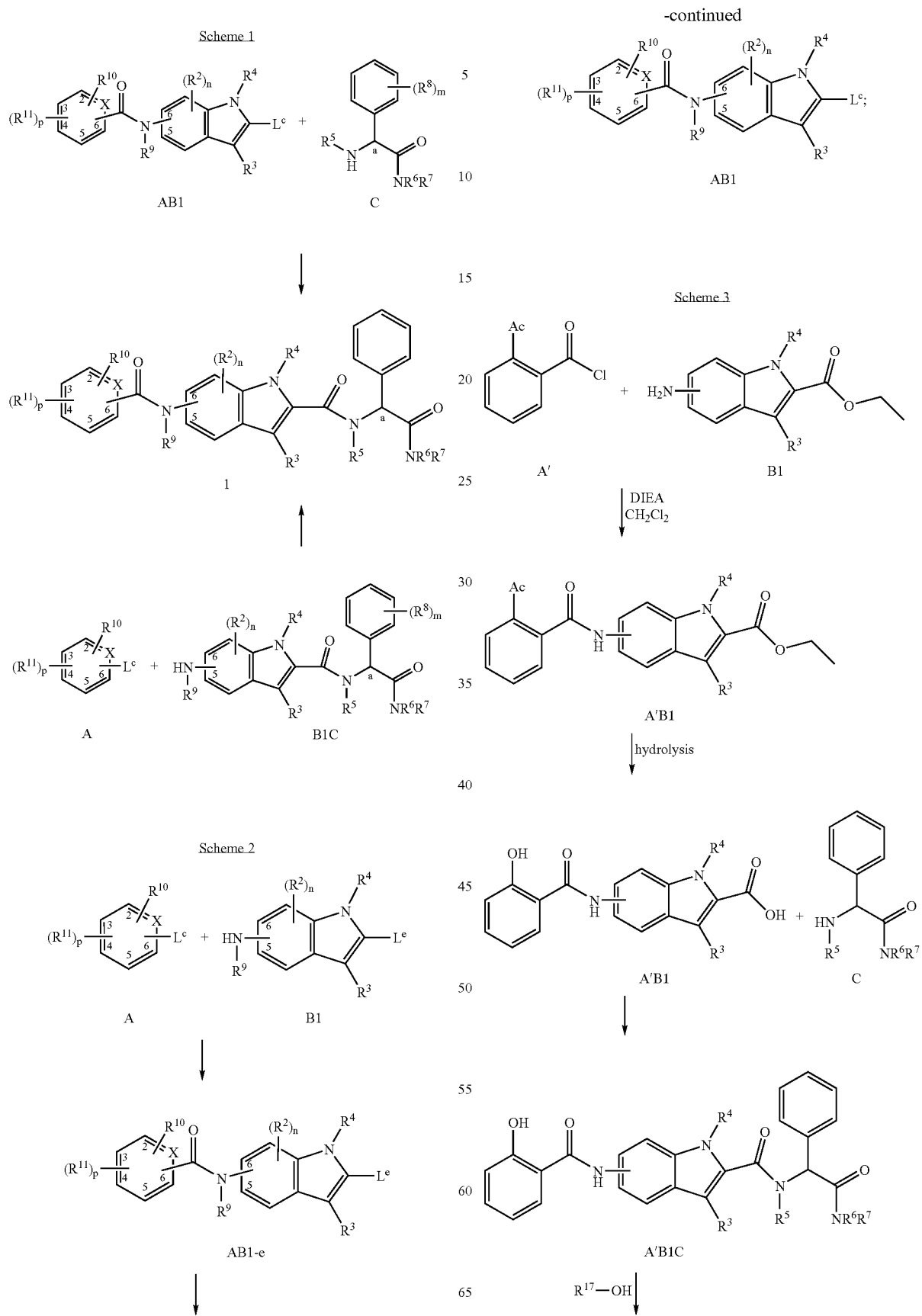

-continued

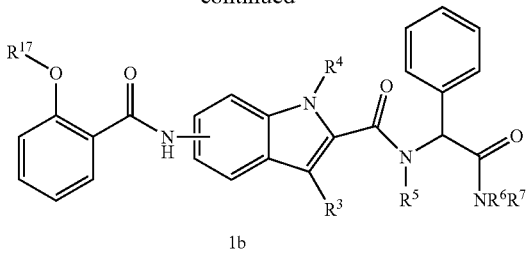

1b

Scheme 1 illustrates a method for preparing a compound of formula 1 which comprises reacting a compound of the formula AB1, with an amine of the formula C, or, by reacting a compound of the formula A with an amine of the formula B1C, where $L^c$ is a carboxylic acid, preferably, an activated carboxylic acid. In both cases, a compound of formula 1 is prepared by the formation of an amide linkage.

Activated carboxylic acids of the compound of formula A and AB1 are readily formed by conventional means, for example, wherein $-L^c$ is —COOH, by reacting the free acid with a carbodiimide, e.g., 1-(3-dimethylaminopropyl)-3-ethylcarbodiimide hydrochloride ("EDC") or 1,1'-carbonyldiimidazole ("CDI"). EDC, if used, may advantageously be polymer-bound, as disclosed in U.S. Pat. No. 5,416,193. Preferably, the amide linkage reaction is carried out in the presence of a suitable base. An example of a suitable base for use in the coupling reaction is a polymer bound amine, such as polymer bound morpholino-polystyrene. Preferably, the reaction is carried out in the presence of an alcohol e.g., a $C_1$-$C_4$ alcohol such as methanol, ethanol, propanol, isopropanol, n-butanol or t-butanol. Alternatively, the carboxylic acid may be activated by conversion to its corresponding acid chloride by e.g., treatment with oxalyl chloride in methylene chloride in the presence of a catalytic amount of DMF. Compounds A, C, AB1 and B1C, and their synthetic precursors and intermediates are each readily prepared using well-known methods for the formation of amide linkages, and also by the methods disclosed herein.

Another example of a method for forming the amide linkage between AB1 and C, from the compound AB1 where $L^c$ is a carboxylic acid, is by combining AB1, C, and PyBroP (about 1 eq) in methylene chloride, followed by the addition of diisopropylethylamine (2-3 eq) and stirring at room temperature from about 30 minutes to 24 hours. The solvent may be evaporated and the product purified by TLC or flash chromatography using ethyl acetate/hexane as the eluting solvent.

Still another example of a method for forming the amide linkage between AB1 and C, where $L^c$ is a carboxylic acid, is to first combine the acid (AB1) with N,O-dimethyl hydroxylamine hydrochloride salt and PyBroP in methylene chloride followed by addition of diisopropylethylamine and stirring for several hours. The resulting N,O-dimethyl hydroxyamide of the acid is purified by flash chromatography and then treated with DIBAL in THF to yield the corresponding aldehyde (i.e., $L^c$ is C(O)H). The AB1 aldehyde is then suspended in methylene chloride with C and acetic acid, and after stirring for about 30 minutes, $NaB(OAc)_3H$ and chloroform are added and the compound of formula 1 purified from the organic layer, e.g., by flash chromatography using methanol/chloroform.

The method illustrated in Scheme 1 comprising reacting a compound of the formula A with an amine of the formula B1C is advantageous in the utilization of a library of A groups, i.e., phenyl or pyridyl carboxylic acids as in Scheme 1, or other carboxylic acids. In this case, a compound of formula 1, formula 1b or formula 2 may be formed between a compound of the formula B1C and a A group or other carboxylic acid, by reacting A or the other acid with a mixture comprising B1C, EDC and DMAP in methylene chloride, preferably at room temperature, followed by addition of N,N-dimethylethylenediamine, and subsequent purification of the compound of formula 1.

Scheme 2 illustrates a method of preparing compounds of formula AB1. In Scheme 2, a compound of formula A is reacted with a 5-amino- or 6-amino-indole of formula B1, wherein $L^e$ is a carboxylic acid ester to form the compound AB1-e, followed by hydrolysis of $L^e$ to form the compound AB, bearing a carboxylic acid group $L^c$, which as described above may be used in the method of Scheme 1 directly or in the form of an activated acid. The group $L^e$ may advantageously be —$COOR^d$, wherein $R^d$ is a ($C_1$-$C_6$) alkyl group or a substituted variation thereof; preferably $R^d$ is methyl or ethyl, more preferably ethyl. Where -$L^c$ is e.g., —COCl, i.e., an acid chloride, the reaction between A and B1 may be carried out in methylene chloride and pyridine or, in a preferred embodiment, as described in Example 44. AB1-e may be hydrolysed (or otherwise deprotected) to form AB1 by any conventional means, e.g., by addition of aqueous LiOH to a solution of the compound in THF and methanol, or, in a preferred embodiment, as described in Example 44, wherein the compound AB1 has advantageous filtration properties, for example where $L^c$ is —COOH and acidification is performed at elevated temperature, and preferably where $L^c$ is —COO$^-$K$^+$ crystallizing as a 2.5 mole hydrate.

Still another embodiment of a process for making a compound of the formula 1 wherein $R^{10}$ is of the formula —$OR^7$ is shown in Scheme 3. In this process, an amide linkage is formed between A'B1 and C, wherein A' is analogous to the group $R^1$ except that $R^{10}$ is, e.g., acetyl or a thioester as exemplified by a compound such as acetylsalicoylchloride. In this process, a compound of the formula A'B1 is formed analogously to the process shown in Scheme 2, by adding to a mixture comprising about 1 equivalent of B1 (ester form, i.e. having "$L^e$" at the 2-position) and diisopropylethylamine (2 eq) in methylene chloride, about one equivalent of A', followed by hydrolysis of the ester group Le of A'B1 to produce a carboxylic acid group $L^c$ and (preferably as part of the same step) hydrolysis of the acetyl group of A' to form an alcohol. The alcohol/acid A'B1 is then reacted with C as described above, in the presence of PyBroP to produce a hydroxy-substituted compound A'B1C whose hydroxyl group may then be converted to $OR^{17}$ by reaction with an alcohol $R^{17}OH$.

Compounds of formula A are well-known, and are readily obtained commercially or prepared from commercially available biphenyl, bipyridyl or phenyl-pyridyl compounds substituted with at least a carboxylic acid group or having at least one substituent susceptible to derivatization to a carboxylic acid group. Examples of suitable groups A and methods for preparing them may be found in, for example, U.S. Pat. No. 6,121,283, which is herein incorporated by reference in its entirety. A particularly preferred group of formula A is 4'-(trifluoromethyl)-2-biphenylcarboxylic acid, which is commercially available; other A groups are commercially available or readily prepared from commercially available analogues by means which are well-known in the art.

Compounds of formula B are readily prepared from well-known or commercially available indoles, e.g., 5-nitro or 6-nitro-indole-2-carboxylic acid ethyl ester ("the indole ester"). To prepare a group B1 wherein $R^4$ is alkyl or alkoxyalkyl, the indole ester in a suitable solvent, e.g., DMF, may be treated with about one equivalent of sodium hydride, followed by addition of a slight molar excess of alkyl iodide or alkoxyalkyl iodide, e.g., methyl iodide, iodomethyl methyl ether, ethyl iodide, 2-iodopropane, etc., followed by quenching with acid, e.g., HCl, and suitable isolation to yield the alkyl or alkoxyalkyl indole ester. Alternatively the alkylating agent may be an alkyl sulfonate ester, e.g. methyl tosylate, and the base may be a inorganic salt, e.g. potassium carbonate, and the product provided by an appropriate isolation, such as described in Example 44. In yet another embodiment, a group B1 wherein $R^4$ is akyl or alkoxyalkyl and $L^c=R^4$, may be prepared by exposing commercially available 5-nitro or 6-nitro-indole-2-carboxylic acid to analogous conditions with adjusted stoichiometry.

Independently, or after alkylation of the indole ester, a compound B1 wherein $R^3$ is halogen, i.e., chloro, bromo or iodo, may be prepared by treating the indole ester with a N-halosuccinimide in a suitable solvent, e.g., THF, followed by neutralization and isolation.

After halogenation and/or alkylation (or alkoxyalkylation) the 5-nitro or 6-nitro group of any of the resulting indole esters (i.e., $R^3$ is H or halo and $R^4$ is independently H, alkyl or alkoxyalkyl) may then be reduced, e.g., with hydrazine hydrate and Raney Nickel in a suitable solvent, e.g., methanol to yield the 5-amino- or 6-amino-indole ester. Alternatively, the nitro group may be hydrogenated catalytically over palladium based catalysts, e.g. palladium on carbon. Alternatively, the nitro group may be hydrogenated catalytically over palladium based catalysts. Alternatively, the nitro group may be subjected to catalytic transfer hydrogenation using palladium based catalysts and a non-gasseous hydrogen source, e.g., a salt of an amine with formic acid such as ammonium fomate, followed by an appropriate isolation, such as described in Example 44. The 5-amino- or 6-amino-indole esters B1 may advantageously be isolated as their salts with strong acids, e.g. hydrochloric acid. Alternatively the 5-amino or 6-amino-indole esters may be retained in solution for use directly in the following synthetic step.

The 5-amino- or 6-amino-indole ester may then be reacted with a compound of formula A as in Scheme 2 to form the compound AB1-e, wherein $R^9$ is hydrogen. The amide nitrogen of AB1-e, is optionally alkylated, e.g., free radical methylation is used to produce $R^9$=methyl, preferably before hydrolysis of the carboxylic acid ester to the corresponding 2-carboxylic acid or activated acid form of the compound of formula B used as in Scheme 1.

Compounds of formula B2 are readily prepared from well-known or commercially available indoles, e.g., 5-nitro or 6-nitro-indole-1-acetic acid. Compounds of formula 2 are then readily prepared by forming amide linkages between A, B2 and C using the processes described above for linking B1 to A (or A') and C.

Compounds of formula B3 are also readily prepared from well-known or commercially available indoles, e.g., 5-nitro or 6-nitro-benzofuran-2-carboxylic acid. The acid is first esterified, and then the nitro group is reduced to an amine, both using conventional means as described herein, and the amide linkages between A, B3 and C to form a compound of formula 1b are readily formed using the processes described herein for linking B1 to A (or A') and C.

Compounds of formula C are readily prepared by methods analogous to those described above, by forming an amide linkage between a phenyl-glycine amino acid analogue, e.g.,

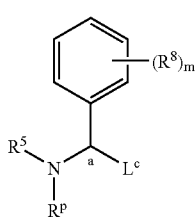

C' and an amine of the formula $HNR^6R^7$, wherein $R^p$ is H or a protecting group, such as tert-butyloxycarbonyl ("BOC"). Various embodiments of processes for preparing a compound of formula C have been described above, and illustrative examples are provided below.

One example of a process for preparing a compound of formula C, where, e.g., $R^7$ is benzyl and $R^6$ is methyl, involves combining commercially available (S)-N-tert-butoxycarbonyl-2-phenylglycine, 1-hydroxybenzotriazole hydrate and N,N'-dicyclohexylcarbodimide in dichloromethane, and after mixing, adding slowly, with stirring, N-methylbenzylamine in dichloromethane, all at 0-5° C. The resulting slurry is allowed to warm to room temperature overnight before being filtered and the solids washed with dichloromethane. The combined filtrate is preferably subjected to further washes with aqueous weak base and then with aqueous weak acid, and finally washed with water, providing a dichloromethane solution of a phenylglycine acid amide, where the phenylglycine amino group (See Table 1, $NHR^5$ of C) is t-butoxycarbonyl-protected. After purification, the phenylglycine amide is deprotected, e.g., by addition of concentrated hydrochloric acid, and the monohydrate crystalline form of the product precipitated by the addition of tert-butyl methyl ether and seeding, followed by washing with tert-butyl methyl ether and drying to yield the product C with higher optical purity than its N-protected precursor. The preferred solid form of the product C is characterized by the XRD (X-ray diffraction) data shown in Table 12, as described below.

Table 12 shows 2-theta values for a simulated X-ray powder diffraction pattern the intermediate compound (S)-N-benzyl-N-methyl-2-phenylglycinamide hydrochloride monohydrate described in Example 44 step (e). The data was simulated using primary data obtained by single crystal X-ray diffraction.

2-theta angles and relative intensifies were calculated from the single crystal structure using the "Diffraction-Crystal" module [revision no. 99.0102] of Cerius2 [version 4.2 Mat. Sci.]. Pertinent simulation parameters were:
Wavelength=1.54178 Å
Polarisation Factor=0.5
Crystallite Size=500×500×500 Å
Lorentzian Peak Shape

TABLE 12

| 2-Theta Angle (/°) | Intensity (/%) |
|---|---|
| 5.673 | 100.00 |
| 11.359 | 8.38 |
| 12.848 | 23.61 |
| 13.354 | 8.19 |
| 13.930 | 8.67 |
| 14.091 | 3.57 |
| 15.374 | 3.21 |
| 15.750 | 3.88 |
| 16.668 | 16.53 |
| 17.501 | 5.36 |
| 17.691 | 6.87 |
| 17.790 | 5.31 |
| 18.073 | 2.47 |
| 18.886 | 2.17 |
| 19.361 | 42.54 |
| 19.363 | 26.18 |
| 19.575 | 3.55 |
| 19.633 | 2.40 |
| 19.922 | 3.34 |
| 20.103 | 15.17 |
| 20.216 | 2.38 |
| 21.352 | 5.08 |
| 21.417 | 6.47 |
| 22.022 | 5.00 |
| 22.750 | 14.75 |
| 22.817 | 6.19 |
| 22.832 | 2.63 |
| 23.948 | 6.50 |

TABLE 12-continued

| 2-Theta Angle (/°) | Intensity (/%) |
|---|---|
| 23.954 | 5.24 |
| 24.322 | 2.66 |
| 24.399 | 3.20 |
| 24.471 | 5.84 |
| 24.681 | 2.98 |
| 24.761 | 21.22 |
| 25.654 | 9.48 |
| 25.699 | 2.71 |
| 25.767 | 5.84 |
| 25.862 | 2.18 |
| 26.425 | 2.02 |
| 26.665 | 3.22 |
| 26.894 | 2.36 |
| 27.054 | 4.25 |
| 27.556 | 7.66 |
| 27.983 | 2.97 |
| 28.071 | 7.04 |
| 28.547 | 5.53 |
| 28.763 | 3.60 |
| 28.771 | 3.31 |
| 29.351 | 10.87 |
| 29.578 | 5.76 |
| 29.983 | 8.44 |
| 30.830 | 8.48 |
| 31.115 | 9.03 |
| 31.746 | 4.06 |
| 31.807 | 3.79 |
| 32.401 | 2.28 |
| 32.540 | 3.47 |
| 33.326 | 2.08 |
| 33.802 | 2.28 |
| 36.240 | 3.98 |
| 37.491 | 2.71 |
| 38.312 | 2.03 |
| 38.360 | 4.67 |
| 39.406 | 2.45 |
| 39.752 | 3.11 |
| 40.510 | 2.81 |
| 43.483 | 2.17 |

In another example of a process for preparing a compound of formula C, where $R^6$ is methyl and $R^7$ is benzyl, (RS)-N-tert-butoxycarbonyl-2-phenylglycine, commercially available or prepared from (RS)-2-phenylglycine using methods well known in the art, is combined with 1-hydroxybenzotriazole hydrate, commercially available N-methylbenzylamine and N-[3-(dimethylamino)propyl-N'-ethylcarbodiimide hydrochloride in dichloromethane and the resulting mixture stirred for about 24 hours. The resulting mixture is subjected to an aqueous work-up similar to that described above, providing (tert-butyl (RS)-2-[benzyl(methyl)amino]-2-oxo-1-phenylethylcarbamate, which may be treated with trifluorocaetic acid and triethylsilane in dichloromethane, followed by aqueous workup to yield (RS)-N-benzyl-N-methyl-2-phenylglycinamide.

A salt of the phenylglycine amide may be prepared, e.g., by treating the amide, e.g., ((RS)-N-benzyl-N-methyl-2-phenylglycinamide), with di(o-toluoyl)-L-tartaric acid in a suitable solvent to provide the di(o-toluoyl)-L-tartrate) salt. Tartrate salts of the phenylglycine amides may be broken to provide the amide, which may be purified as its hydrochloride salt.

In still another embodiment of a process for preparing a compound of formula C, commercially available (RS)-DL-2-phenylglycine is converted to (RS)-4-phenyl-1,3-oxazolidine-2,5-dione using methods well known in the art, which, analogous to the above examples, is then combined with commercially available N-methylbenzylamine. The resulting mixture is then subjected to an aqueous work-up, providing the phenylglycinamide, which may be purified as its hydrochloride salt as described.

In another embodiment, racemic compounds of the formula C may be resolved via the selective precipitation of one of the enantiomers as its salt with an optically enriched chiral acid, of which many examples are known in the art, from suitable solvents, e.g. methanol and ethanol. Such optically enriched chiral acids may be naturally occuring or synthetic. The precipitated salts may be hydrates or solvates. Breakage of these salts delivers optically enriched free amines of the formula C, which may be purified as-is or as a suitable salts using suitable solvents.

In a preferred embodiment, (RS)-N-benzyl-N-methyl-2-phenylglycinamide (10.0 g) was treated with di(o-toluoyl)-L-tartaric acid (15.2 g) in methanol (167 mL) at 20° C. The precipitated the salt was filtered and washed with methanol, then dried providing (S)-N-benzyl-N-methyl-2-phenylglycinamide di(o-toluoyl)-L-tartrate (11.73 g, 46.6%) with 92.7% d.e. (chiral HPLC). This material (1.00 g) was reslurried in hot methanol (8.8 ml) to provide (S)-N-benzyl-N-methyl-2-phenylglycinamide di(o-toluoyl)-L-tartrate with 99% d.e. (0.79 g, 79% recovery) after filtration, washing and drying. The tartrate salts formed as described maybe broken to provide the free amine of formula C, i.e. (S)-N-benzyl-N-methyl-2-phenylglycinamide, which may be advantageously purified by the formation of a salt with an achiral acid in the presence of appropriate solvents, e.g. precipitation of (S)-N-benzyl-N-methyl-2-phenylglycinamide hydrochloride from mixtures of propan-2-ol and tert-butyl methyl ether as described.

In another embodiment, a racemic compound of the formula C may be resolved via the selective recrystallization, from a suitable solvent, of its salt with an optically enriched chiral acid, e.g. (RS)-N-benzyl-N-methyl-2-phenylglycinamide di(o-toluoyl)-L-tartrate prepared as described above, to provide diastereomericly enriched salts, e.g. (S)-N-benzyl-N-methyl-2-phenylglycinamide di(o-toluoyl)-L-tartrate. Breakage of these salts delivers optically enriched free amines of the formula C, which may be advantageoulsy isolated and used as the hydrochloride salt, e.g. (S)-N-benzyl-N-methyl-2-phenylglycinamide hydrochloride as described.

In another embodiment, where optically enriched compunds C are preferable, the unwanted enantiomer of the compound C may be recycled by racemization. In a more preferred embodiment, the racemization is applied to mother liquors from the resolutions described in the preceding embodiments, by (a) optionally changing the nature of the solvent and (b) refluxing in the presence of a catalytic amount of a carbonyl compound, e.g. 2-chlorobenzaldehyde, thus allowing the isolation of second crops of diastereomericly enriched salts containing the desired enantiomer of compound C, e.g. (S)-N-benzyl-N-methyl-2-phenylglycinamide di(o-toluoyl)-L-tartrate with 92% d.e. in approximately 50% yield of the solute in the initial ethanolic mother liquors. In an even more preferred embodiment, the catalysed racemization is performed at a suitable temperature and concentration in-situ during the resoluton in a suitable solvent, prior to the isolation of the first crop of product; this "dynamic resolution" allows a first crop yield of product to be significantly greater than the 50% available by traditional salt resolutions. Dynamic resoultions are known in the art, but suitable conditions are generally highly substrate-dependent.

In still another embodiment of a process for preparing an opticaly enriched compound of formula C, commercially available homochiral (S)-L-2-phenylglycine is converted to (S)-4-phenyl-1,3-oxazolidine-2,5-dione using methods well known in the art, which, may then be combined with commercially available N-methylbenzylamine. The resulting mixture is then subjected to an aqueous work-up, providing the phenylglycinamide, e.g. (S)-N-benzyl-N-methyl-2-phenylglycinamide with 43% e.e. in 49% yield, which may be purified as its hydrochloride salt as described, or di(o-toluoyl)-L-tartrate salt.

BIOLOGICAL ASSAYS

The selectivity of the apo B secretion/MTP inhibitors was determined by the following protocols.

Inhibition of Fat Absorption

Healthy female CF1 mice (Charles River) weighing 18-20 grams upon arrival are employed as test subjects. The mice are housed, in groups of 10 in standard caging, and are allowed to acclimate for one week prior to testing. Mice are fasted overnight in a separate procedure room prior to testing. Each treatment group typically consists of 5 mice.

The test compound is preferably provided as a powder in a glass vial. The dosing solution (0.10 ml/25 g body weight) administered by oral gavage consists of an emulsion of Miglyol 812 (20%), Cremaphor (5%), Water (75%). An appropriate volume of Miglyol is first added to the test compound, and the vial vortexed for approximately 1 minute. Next, the appropriate volume of Cremaphor is added, and the vial again vortexed as previously. The appropriate volume of water is then added, and the emulsion formed by vortexing and briefly sonicating.

Hamster liquid diet (Bioserve F0739) (dose volume 0.5 ml/25 g body weight) is prepared by adding (for every 10 mL needed) 2.5 grams liquid diet powder, 10 mL water and 5 microcuries glycerol-$^3$H-trioleate (Amersham TRA191) to a laboratory blender. The mixture is then blended at high speed for approximately 1 minute. The liquid diet is stored at 4° C. until use.

Sample tubes are weighed (Falcon 15 ml polypropylene conical). Three milliliters of 2.5N KOH is then added to each tube.

Following overnight fasting, each mouse is dosed (see above volumes) with test compound followed immediately by liquid diet. Positive (a known potent MTP inhibitor) and negative control groups (vehicle) are included in each assay. One scintillation vial is sham dosed every 30 mice in order to determine the activity of the initial bolus.

At two hours post dose the mice are euthanized by carbon dioxide inhalation, the abdominal cavity opened, and the small intestines removed and placed in the KOH conical tube. Each tube is then weighed.

Tubes containing intestines are then placed in a 75° C. water bath for 1.5-2 hours. Following saponification, the tubes are vortexed and 200 µL saponate placed in a 20 mL liquid scintillation vial. Samples are decolorized (for 30 minutes) by adding 200 µL of 30% (w/w) hydrogen peroxide. Each sample is neutralized by the addition of 200 µL of 3N HCL. Ten milliliters of Ready Safe® (Beckman) liquid scintillation fluid are added and the samples were counted on a Beckman Coulter LS 6500 scintillation system.

The calculations are carried out as follows:

weight of saponate=weight of tube (KOH+intestine)−weight of empty tube saponate fraction=0.22/saponate weight (density of the saponate=1.1 g/mL; therefore the weight of the aliquot is equal to 0.22 g)

total DPM for the entire intestine=DPM of sample/saponate fraction

The initial bolus DPM is calculated by averaging the counts from the sham dosed scintillation vials.

The fraction of bolus recovered from the intestine (percent recovery)=total DPM/bolus count.

Percent recovery from each test group=average of percent recovery from each mouse.

Interpretation of Results:

To compare efficacy of test compounds, an $ED_{25}$ for intestinal fat absorption is calculated. The (average) percent triglyceride recovery (percent unabsorbed and remaining in the intestine) of the vehicle control group is adjusted to equal 0%, and the (average) percent recovery of the compound control group is adjusted to equal 100%. The same calculations are applied to the percent recovery values obtained for test compounds and an adjusted percent recovery is obtained (% recovery of the test sample−% recovery of vehicle control group/(% recovery of positive control group−% recovery of vehicle control group)). An $ED_{25}$ is then calculated by plotting a graph of compound concentration vs. adjusted percent recovery.

Serum Triglyceride Lowering

Healthy female CF1 mice (Charles River) weighing 18-20 grams upon arrival are employed as test subjects. The mice are housed in groups of 10 in standard caging, and were allowed to acclimate for one week prior to testing. Mice are fasted overnight in a separate procedure room prior to testing. Each treatment group typically consists of 10 mice.

The test compound is preferably provided as a powder in a glass vial. The dosing solution (0.250 ml/25 g body weight) administered by oral gavage consists of an emulsion of Miglyol 812 (40%), Cremaphor (10%), Water (50%). An appropriate volume of Miglyol is first added to the test compound, and the vial vortexed for approximately 1 minute. Next, the appropriate volume of Cremaphor is added, and the vial again vortexed as previously. The appropriate volume of water is then added and the emulsion formed by vortexing and briefly sonicating.

Following overnight fasting, each mouse is dosed (see above volumes) with test compound. At 1 hour post dose the mice are euthanized by carbon dioxide inhalation and blood collected for triglyceride quantitation.

Serum triglyceride values are quantitated using a colorimetric endpoint assay (Wako Triglyceride E kit # 432-4021) on a Spectra Max 250 plate reader with Softmax Pro software. All samples are run in duplicate.

For comparison of triglyceride values, the percent change from control is calculated. The average triglyceride value of the test compound group is divided by the average triglyceride value of the vehicle group, multiplied by 100 and then subtracted from 100%. The $ED_{25}$ value is then calculated by plotting a graph of compound concentration versus percent change from control.

The relative values of the $ED_{25}$ for triglyceride lowering and the $ED_{25}$ for inhibition of intestinal fat absorption are used as a means to compare selectivity of the test compounds.

Where HPLC is referred to in the preparations and examples below, the general conditions used, unless otherwise indicated, are as follows: the column used was a Phenomenex Luna™ C-8 column (3.0×250 mm), and the column was eluted using a gradient of 90% A 10% B to 100% B over 45 minutes, where solvent A was 0.1% formic acid in water and solvent B was acetonitrile. The column was run on a Agilent 1100 MSD system.

EXAMPLES

Example 1

(S)-1-Ethyl-5-[(4'-trifluoromethyl-biphenyl-2-carbonyl)-amino]-1H-indole-2-carboxylic acid {2-[benzyl(methyl)amino]-2-oxo-1-phenylethyl} amide

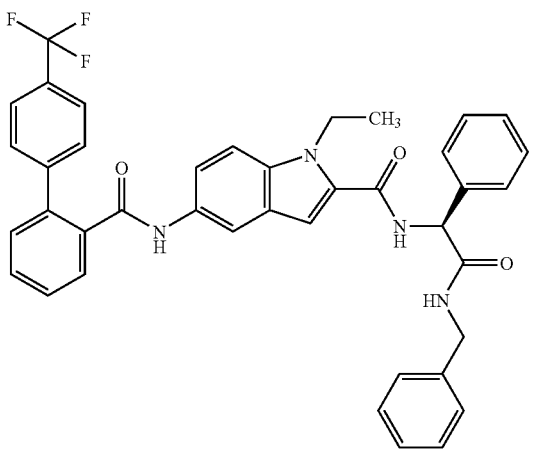

(a) 1-Ethyl-5-nitro-1H-indole-2-carboxylic acid ethyl ester

5-Nitro-1H-indole-2-carboxylic acid ethyl ester (5 g, 21.3 mol) was dissolved in DMF (50 mL). The reaction mixture was cooled to 0° C. Sodium hydride (1.02, 25.5 mmol, 60% in mineral oil) was added to the above solution in portions over 10 minutes. The mixture was stirred at room temperature for 30 minutes. Ethyl iodide (6.5 g, 42 mmol) was added to the above solution and the reaction mixture was stirred overnight. Ethanol (30 mL) was added to the reaction mixture and the mixture was poured into cold water (800 mL). The crude product was collected by filtration and used directly in next step without further purification (5 g).

(b) 5-Amino-1-ethyl-1H-indole-2-carboxylic acid ethyl ester

The 1-ethyl-5-nitro-1H-indole-2-carboxylic acid ethyl ester (59, 19.1 mmol) of step (a) was dissolved in EtOH/n-PrOH (100 mL, 1/1). Palladium hydroxide (1.14 g) and ammonium formate (3.92 g, 62.2 mmol) were added to the above solution. The mixture was heated to reflux for 2 hours. The reaction mixture was cooled to room temperature and the catalyst was filtered off through Celite. The solvent was removed under reduced pressure. The crude product was dissolved in dichloromethane (300 mL) and washed with NaHCO$_3$ (150 ml×2). The organic layer was collected, dried (Na$_2$SO$_4$) and evaporated. The crude product was purified by chromatography to furnish the desired product (4 g, 90%).

(c) 1-Ethyl-5-[(4'-trifluoromethyl-biphenyl-2-carbonyl)-amino]-1H-indole-2-carboxylic acid ethyl ester 4'-Trifluoromethyl-biphenyl-2-carboxylic acid (5.04 g, 18.95 mmol) and 1-ethyl-5-nitro-1H-indole-2-carboxylic acid ethyl ester (4.00 g, 17.23 mmol) were dissolved in DCM (100 mL). DIEA (8 g, 61.8 mmol) was added to the above mixture and the mixture was stirred at room temperature for 5 minutes. PyBroP (9.63 g, 20.67 mmol) was added to the above solution in one portion. The reaction mixture was stirred for another 3 hours. The precipitate was filtered off and washed with cold DCM to provide the title compound (4.59, 54.4%).

(d) 1-Ethyl-5-[(4'-trifluoromethyl-biphenyl-2-carbonyl)-amino]-1H-indole-2-carboxylic acid 1-Ethyl-5-[(4'-trifluoromethyl-biphenyl-2-carbonyl)-amino]-1H-indole-2-carboxylic acid ethyl ester (4.5 g, 9.37 mmol) was added to MeOH/H$_2$O (110 mL, 10/1). Lithium hydroxide monohydrate (1.5 g, 35.7 mmol) was added to the above mixture. The mixture which resulted was heated to reflux overnight. The solvent was removed under reduced pressure and the residue was dissolved in H$_2$O (500 mL). The solution was acidified with 6N HCl to pH 2. The solid was collected by filtration and dried under vacuum (4.0 g, 94.5%).

(e) (S)-(Benzylcarbamoyl-phenyl-methyl)-carbamic acid tert-butyl ester (S)-tert-Butoxycarbonylamino-phenyl-acetic acid (1.00 g, 4 mmol) was dissolved in DCM (15 mL). Benzylamine (0.428 g, 4 mmol) and DIEA (0.65 g, 5 mmol) were added to the above mixture. The mixture which resulted was stirred at room temperature for a few minutes. PyBroP (2.10 g, 4.5 mmol) was added to the above solution in one portion and the reaction mixture was stirred overnight. The reaction mixture was diluted with DCM (150 mL) and washed with NaHCO$_3$ (50 mL×2, sat.). The organic layer was collected and dried (Na$_2$SO$_4$) and the solvent was removed under reduced pressure. The crude product was purified by chromatography to provide the desired product (0.859, 62%).

(f) (S)-2-Amino-N-benzyl-2-phenyl-acetamide hydrochloride (S)-(Benzylcarbamoyl-phenyl-methyl)carbamic acid tert-butyl ester (0.85 g, 2.50 mmol) was dissolved in HCl/dioxane (10 mL, 4.0M). The mixture was stirred at room temperature overnight. The volatiles were removed under reduced pressure to provide the desired product in quantitative yield.

(g) (S)-1-Ethyl-5-[(4'-trifluoromethyl-biphenyl-2-carbonyl)amino]-1H-indole-2-carboxylic acid [2-(benzylamino)-2-oxo-1-phenylethyl] amide 1-Ethyl-5-[(4'-trifluoromethyl-biphenyl-2-carbonyl)amino]-1H-indole-2-carboxylic acid (0.05 g, 0.11 mmol) and (S)-2-Amino-N-benzyl-2-phenyl-acetamide hydrochloride (0.031 g, 0.11 mmol) were combined in DCM (3 mL) and DIEA (1.1 mL) was added to the above mixture. PyBroP (0.077 g, 0.17 mmol) was added to the above mixture in one portion. The mixture which was resulted was stirred overnight. The crude mixture was then purified by HPLC to furnish the desired product (52.7 mg). HPLC retention time 16.892 min.; Mol. Wt. (calc) 674.7; MS (found) 675.2.

Examples 2-24 were prepared similarly to the above example. In each of Examples 2-24, the A group comprised (4'-trifluoromethyl)biphenyl-2-carbonyl linked to a 5-amino group of B1.

In Examples 6, 11 and 16, R$^6$ and R$^7$ together with the nitrogen atom to which they are attached comprise the listed heterocyclyl group. The benzylation of the indole nitrogen in Example 14 was performed similarly to Example 1, step (a). All of the required amines HNR$^6$R$^7$ are commercially available or readily prepared using methods well-known in the art.

TABLE 2

| Example | R$^4$ | R$^6$ | R$^7$ | mol. wt. (calc) | MS (found) | HPLC (min) |
|---|---|---|---|---|---|---|
| 2 | Methyl | H | 4-Methoxy-benzyl | 690.729 | 691.2 | 15.98 |
| 3 | Propyl | Methyl | Benzyl | 702.783 | 703.2 | 20.797 |
| 4 | Propyl | H | Butyl | 654.739 | 655.2 | 18.478 |

TABLE 2-continued

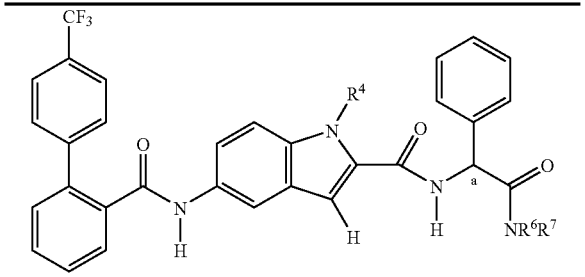

| Example | R⁴ | R⁶ | R⁷ | mol. wt. (calc) | MS (found) | HPLC (min) |
|---|---|---|---|---|---|---|
| 5 | propyl | Methyl | Butyl | 668.766 | 669.2 | 21.237 |
| 6 | Propyl | Morpholin-4-yl | | 668.722 | 669.2 | 16.102 |
| 7 | H | Ethyl | Ethyl | 612.658 | 613.2 | 15.158 |
| 8 | Ethyl | H | Isopropyl-methyl | 640.712 | 641.2 | 17.318 |
| 9 | Ethyl | Methyl | Benzyl | 688.756 | 689.2 | 19.712 |
| 10 | Ethyl | Methyl | Propyl | 640.712 | 641.2 | 18.505 |
| 11 | Ethyl | Pyrrolidin-1-yl | | 638.696 | 639.2 | 16.558 |
| 12 | H | H | Propyl | 598.63 | 599.2 | 13.357 |
| 13 | H | H | Cyclopropyl-methyl | 610.642 | 611.2 | 13.741 |
| 14 | Benzyl | H | Isopropyl-methyl | 702.783 | 703.2 | 19.25 |
| 15 | Propyl | H | Benzyl | 688.756 | 689.2 | 24.897 |
| 16 | H | Pyrrolidin-1-yl | | 610.642 | 611.2 | 13.337 |
| 17 | H | Methyl | Pyridin-3-ylmethyl | 661.69 | 662.2 | 5.671 |
| 18 | Methyl | Methyl | Pyridin-3-ylmethyl | 675.717 | 676.2 | 7.099 |
| 19 | Benzyl | Methyl | Pyridin-3-ylmethyl | 751.816 | 752.2 | 16.229 |
| 20 | Ethyl | H | 3-methyl-benzyl | 688.756 | 689.2 | 18.511 |
| 21 | Benzyl | H | 3-methyl-benzyl | 750.828 | 751.2 | 20.242 |
| 22 | Benzyl | H | 2-phenyl-prop-2-yl | 764.855 | 765.2 | 21.217 |
| 23 | Benzyl | H | 4-methyl-benzyl | 750.828 | 751.2 | 20.209 |
| 24 | Methyl | H | 4-fluoro-benzyl | 678.693 | 679.2 | 16.585 |

Example 25

1-Methyl-5-[(6-methyl-4'-trifluoromethyl-biphenyl-2-carbonyl)-amino]-1H-indole-2-carboxylic acid (2-methylamino-2-oxo-1-phenylethyl)amide

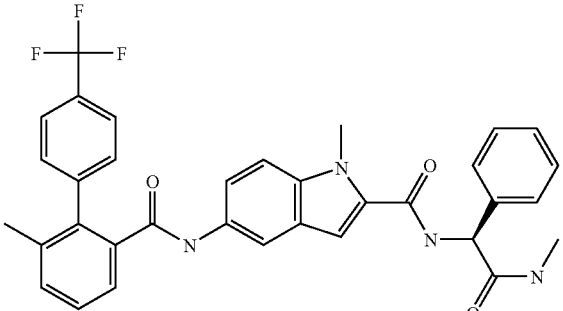

(a) 6-Methyl-4'-trifluoromethyl-biphenyl-2-carboxylic acid methyl ester was Prepared According to Methods Well-Known in the Art (see, e.g., WO00/05201)

(b) 6-Methyl-4'-trifluoromethyl-biphenyl-2-arboxylic acid

6-Methyl-4'-trifluoromethyl-biphenyl-2-carboxylic acid methyl ester (3.5 g, 11.90 mmol) was dissolved in MeOH/H₂O (60 mL, 5/1). Lithium hydroxide monohydrate (0.75 g, 17.8 mmol) was added to the above solution. The mixture which resulted was heated to reflux overnight. The solvent was removed under reduced pressure and the residue was dissolved in H₂O (150 mL). The solution was acidified with HCl (6N) to a pH of about 2. The solid was collected by filtration and dried under vacuum (2.5 g, 75%). MS: 280.2. H¹NMR (DMSO-d₆): δ 2.01 (s, 3H), 7.40 (m, 3H), 7.49 (d, 1H, J=7.3 Hz), 7.65 (d, 1H, J=7.3 Hz), 7.75 (d, 2H, 8.3 Hz).

(c) 1-Methyl-5-[(6-methyl-4'-trifluoromethyl-biphenyl-2-carbonyl)-amino]-1H-indole-2-carboxylic acid ethyl ester was Prepared Similarly to Example 1, Step (c)

(d) 1-Methyl-5-[(6-methyl-4'-trifluoromethyl-biphenyl-2-carbonyl)-amino]-1H-indole-2-carboxylic acid was Prepared Similarly to Example 1, Step (d)

(e) 1-Methyl-5-[(6-methyl-4'-trifluoromethyl-biphenyl-2-carbonyl)-amino]-1H-indole-2-carboxylic acid (2-methylamino-2-oxo-1-phenylethyl)amide was Prepared Similarly to Example 1, Step (g)

The compounds in Table 3 were prepared similarly to Example 25. In Examples 28 and 29, R⁶ and R⁷ together with the nitrogen atom to which they are attached comprise the listed heterocyclyl group.

TABLE 3

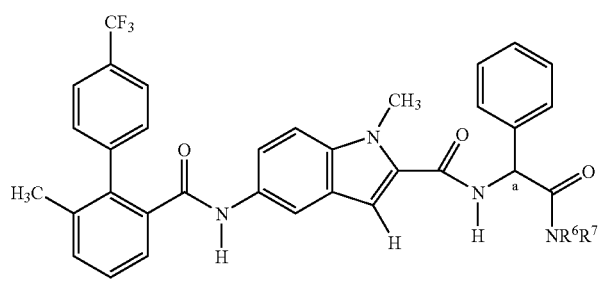

| Example | R⁴ | R⁶ | R⁷ | Mol. Wt. (calc) | MS | HPLC (min) |
|---|---|---|---|---|---|---|
| 26 | Methyl | Methyl | Benzyl | 688.756 | 689.9 | 19.563 |
| 27 | Methyl | H | Cyclopropylmethyl | 638.696 | 639.8 | 16.245 |

TABLE 3-continued

| Example | R⁴ | R⁶ | R⁷ | Mol. Wt. (calc) | MS | HPLC (min) |
|---|---|---|---|---|---|---|
| 28 | Methyl | | Morpholin-1-yl | 654.695 | 655.7 | 14.74 |
| 29 | Methyl | | Pyrrolidin-1-yl | 638.696 | 639.4 | 16.269 |
| 30 | Methyl | H | Propyl | 626.685 | 627.8 | 15.959 |
| 31 | Methyl | Methyl | Pyridin-3-ylmethyl | 689.744 | 690.7 | 7.821 |
| 32 | Methyl | H | 4-methoxy-benzyl | 704.756 | 705.9 | 16.961 |
| 33 | Methyl | H | 4-carboxylic acid methyl ester | 732.766 | 733.9 | 16.564 |
| 34 | Methyl | H | Propen-3-yl | 624.6689 | 625.8 | 15.356 |
| 35 | Methyl | H | Methyl | 598.63 | 599.3 | 13.269 |

Example 36

1-Methyl-5-{[2-(4-trifluoromethyl-phenyl)pyridine-3-carbonyl]-amino}-1H-indole-2-carboxylic acid {2-[benzyl(methyl)amino]-2-oxo-1-phenylethyl}amide

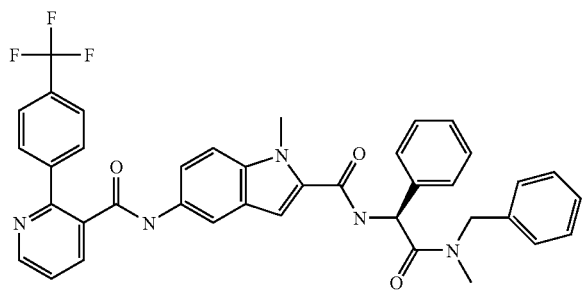

(a) 2-(4-Trifluoromethyl-phenyl)-nicotinic acid methyl ester was Prepared According to the Literature (WO00/05201)

(b) 2-(4-Trifluoromethyl-phenyl)-nicotinic acid was Prepared Similarly to 6-Methyl-4'-trifluoromethyl-biphenyl-2-carboxylic acid as Described in Example 25

(c) 1-Methyl-5-{[2-(4-trifluoromethyl-phenyl)-pyridine-3-carbonyl]-amino}-1H-indole-2-carboxylic acid ethyl ester was Prepared Similarly to Example 1, Step (c)

(d) 1-Methyl-5-{[2-(4-trifluoromethyl-phenyl)-pyridine-3-carbonyl]-amino}-1H-indole-2-carboxylic acid was Prepared Similarly to Example 1, Step (d)

(e) 1-Methyl-5-{[2-(4-trifluoromethyl-phenyl)-pyridine-3-carbonyl]-amino}-1H-indole-2-carboxylic acid {2-[benzyl(methyl)amino]-2-oxo-1-phenylethyl}amide was Prepared Similarly to Example 1, Step (g)

The compounds in Table 4 were prepared similarly to Example 36. In Examples 40 and 41, R⁶ and R⁷ together with the nitrogen atom to which they are attached comprise the listed heterocyclyl group.

TABLE 4

| Example | R⁴ | R⁶ | R⁷ | Mol. wt. (calc) | MS | HPLC (min) |
|---|---|---|---|---|---|---|
| 37 | Methyl | Ethyl | Ethyl | | | |
| 38 | Methyl | H | Cyclopropylmethyl | 625.65 | 626.8 | 11.50 |

TABLE 4-continued

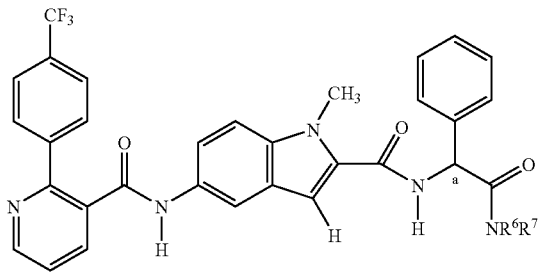

| Example | R⁴ | R⁶ | R⁷ | Mol. wt. (calc) | MS | HPLC (min) |
|---|---|---|---|---|---|---|
| 39 | Methyl | H | Benzyl | 661.69 | 662.8 | 12.95 |
| 40 | Methyl | | Morpholin-4-yl | 641.65 | 642.5 | 9.72 |
| 41 | Methyl | | Pyrrolidin-1-yl | 625.65 | 626.5 | 11.44 |
| 42 | Methyl | Methyl | Pyridin-3-yl | 676.70 | 677.5 | 3.72 |
| 43 | Methyl | H | 4-carboxylic acid methyl ester | 719.73 | 720.8 | 12.10 |

Example 44

Where HPLC is referred to in steps (c), (d), (e), and (f) of this example below, unless otherwise stated, the conditions used are as follows: the column used was a Jones Genesis C-18 300 4μ column (150 mm, part No. FM15960E), and the column was eluted using a gradient of 95% A 5% B to 10% A 90% B over 12 minutes, where solvent A was 0.1% trifluorocaetic acid in water and solvent B was 0.1% trifluorocaetic acid in acetonitrile, with a flow rate of 1.5 ml/min. The column was run on a Hewlett Packard 1100 system.

(S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide (a) Ethyl 1-methyl-5-nitro-1H-indole-2-carboxylate was prepared by methylation of ethyl 5-nitro-1H-indole-2-carboxylate using methods well known in the art (see, e.g., E. F. V. Scriven et al., J.C.S., P.T.1, (1979) p. 53-59). For example, methylation may be achieved using any compatible combination of electrophilic methylating agent, i.e., H₃C-LG, where LG is a leaving group, and a base, e.g., using dimethylsulfate, methyl iodide (Example 45, step (a)) or methyl tosylate, with bases such as sodium hydride, potassium t-butoxide or potassium carbonate. Preferably, methyl tosylate and potassium carbonate are used as follows:

To a refluxing mixture of commercially available ethyl 5-nitro-1H-indole-2-carboxylate (420 g) and potassium carbonate (272.6 g) in acetonitrile (3360 mL) was added a solution of methyl p-toluenesulfonate (367.3 g) in acetonitrile (630 mL), and the resulting mixture refluxed for 18 hours. The mixture was then cooled to 20° C. over 3 hours and water (4200 mL) added over a 3 hour period. The product was granulated, filtered, washed with a 50/50 mixture of demineralized water and acetonitrile (630 mL), demineralized water (420 mL) and then with ethanol (420 mL), and dried, yielding the product ethyl 1-methyl-5-nitro-1H-indole-2-carboxylate (436.19, 96%).

(b) Ethyl 5-amino-1-methyl-1H-indole-2-carboxylate

Alternative A. To a mixture of ethyl 1-methyl-5-nitro-1H-indole-2-carboxylate (420 g), from step (a) or commercial sources, and 10% palladium on carbon catalyst (50% wet) (42 g) in ethanol (4200 mL) was added a solution of ammonium formate (541.59) in demineralized water (840 mL) at between 25-35° C. over 3 hours. The mixture was stirred for 18 hours at 20° C., and then filtered, washing the solids with ethanol (2100 mL). The combined filtrate and washings were concentrated to 840 mL under vacuum at about 20° C. The resulting slurry was granulated at 5° C., filtered, washed with chilled ethanol (420 mL), and dried to give product ethyl 5-amino-1-methyl-1H-indole-2-carboxylate (316.5 g, 86%).

Preferred alternative B. A mixture of ethyl 1-methyl-5-nitro-1H-indole-2-carboxylate (150.0 g), from step (a) or commercial sources, and 10% palladium on carbon catalyst (50% wet) (15.0 g) in ethyl acetate (1800 mL) was hydrogenated at 3 bar at 30° C. for 8 hours. The mixture was then filtered and the solids washed with ethyl acetate (300 mL). The combined filtrate and washings were partially azeotropically dried at reflux and then concentrated to 800 mL to give a solution of product ethyl 5-amino-1-methyl-1H-indole-2-carboxylate in ethyl acetate.

The acid salts of ethyl 5-amino-1-methyl-1H-indole-2-carboxylate are also readily available via methods well-known in the art. For example, the hydrochloride salt is readily prepared by treating an ethylacetate solution of the amine with hydrochloric acid in propan-2-ol.

(c) Ethyl 1-methyl-5-[4'-(trifluoromethyl)[1,1'-biphenyl]-2-carboxamido]-1H-indole-2-carboxylate Alternative A. 4'-(Trifluoromethyl)[1,1'-biphenyl]-2-carboxylic acid (133 g), commercially available, thionyl chloride (89 g) and a catalytic amount of N,N-dimethylbenzamide (2.3 g) were combined in toluene (665 mL) at 55-60° C. over 2 hours, and the mixture heated at 80° C. for 1 hour. The excess reagent was removed by atmospheric co-distillation with toluene (600 ml distillate removed), providing a solution of 4'-(trifluoromethyl)[1,1'-biphenyl]-2-carbonyl chloride, which was combined with ethyl 5-amino-1-methyl-1H-indole-2-carboxylate (109 g) from the previous step, ethyl acetate (4660 ml) and N,N-diisopropylethylamine (131 mL) at 18-29° C. The resulting slurry was cooled, filtered and the crude product solids were washed with propan-2-ol (330 mL). The crude product was twice reslurried in a 70/30 mixture of demineralized water and propan-2-ol (2×1500 mL), and the solids were filtered, washed with propan-2-ol (400 mL) and dried, yielding the title compound, ethyl 1-methyl-5-[4'-(trifluoromethyl)[1,1'-biphenyl]-2-carboxamido]-1H-indole-2-carboxylate (167 g, 71.8%).

Preferred alternative B. A solution of commercially available 4'-(trifluoromethyl)[1,1'-biphenyl]-2-carboxylic acid (150.0 g) in toluene (975 ml) and acetonitrile (1275 mL) was added to a solution of thionyl chloride (100.4 g) and N-methylpyrrolidone (3.7 g) in toluene (750 mL) at reflux. The resulting mixture was heated at reflux for 18 hrs, then the acetonitrile and excess thionyl chloride were distilled off by reducing the volume to 900 mL. Additional toluene (2250 mL) was then added before re-concentrating to provide a solution of the intermediate acid chloride (4'-(trifluoromethyl)[1,1'-biphenyl]-2-carbonyl chloride) (900 mL). This solution was then diluted with ethyl acetate (2620 mL) and N,N-diisopropylethylamine (109.5 g) was added. An ethyl acetate solution of ethyl 5-amino-1-methyl-1H-indole-2-carboxylate (1.07 mole equivalents), from step (b), (solution volume 800 mL) was then added in two portions at 20-25° C., seeding with product (ethyl 1-methyl-5-[4'-(trifluoromethyl)[1,1'-biphenyl]-2-carboxamido]-1H-indole-2-carboxylate) between portions. The crude product was granulated overnight then isolated by filtration and washed with propan-2-ol (450 mL). The crude product was twice reslurried in a 75/25 mixture of demineralized water and propan-2-ol (2×180 mL), and the solids were filtered, washed with propan-2-ol (450 mL) and dried, yielding product (ethyl 1-methyl-5-[4'-(trifluoromethyl)[1,1'-biphenyl]-2-carboxamido]-1H-indole-2-carboxylate) (196 g, 74.5%). Mol wt (calc) 466.46, MS: 467.1 (MH$^+$). $^1$H NMR (DMSO-d$_6$): δ 1.31 (t, 3H, J=7.2 Hz), 3.97 (s, 3H), 4.30 (q, 2H, J=7.2 Hz), 7.12 (s, 1H), 7.34 (d, 1H), 7.46-7.74 (complex, 9H), 7.93 (s, 1H), 10.22 (s, 1H).; HPLC retention time 11.10 minutes.

(d) Alternative A. 1-Methyl-5-[4'-(trifluoromethyl)[1,1'-biphenyl]-2-carboxamido]-1H-indole-2-carboxylic acid sodium salt hydrate Ethyl 1-methyl-5-[4'-(trifluoromethyl)[1,1'-biphenyl]-2-carboxamido]-1H-indole-2-carboxylate (46.7 g) from the previous step and aqueous sodium hydroxide (8.0 g in 140 ml) were combined in refluxing ethanol (280 mL) for 1 hour. The solution was cooled, granulating overnight and the resulting slurry was filtered. The product solids were washed with an ethanol-water mixture and dried, yielding the title compound, 1-methyl-5-[4'-(trifluoromethyl)[1,1'-biphenyl]-2-carboxamido]-1H-indole-2-carboxylic acid sodium salt hydrate (36.3 g, 79% as-is). Anhydrous Mol wt of parent acid (calc) 438.41, MS: 439.2 (MH$^+$), 437.0 (M$^-$). $^1$H NMR (DMSO-d$_6$): δ 4.00 (s, 3H), 6.55 (s, 1H), 7.12-7.75 (complex, 11H), 10.04 (s, 1H).; HPLC retention time 9.30 minutes.

Alternative B. 1-Methyl-5-[4'-(trifluoromethyl)[1,1'-biphenyl]-2-carboxamido]-1H-indole-2-carboxylic acid hemihydrate 1-methyl-5-[4'-(trifluoromethyl)[1,1'-biphenyl]-2-carboxamido]-1H-indole-2-carboxylic acid sodium salt hydrate (0.629), from the previous alternative, and aqueous hydrochloric acid (2 molar) were combined in refluxing ethanol (13 mL) and water (1.3 mL). The mixture was cooled, granulating overnight, chilled in ice and the resulting slurry was filtered. The product solids were dried, yielding the title compound, 1-methyl-5-[4'-(trifluoromethyl)[1,1'-biphenyl]-2-carboxamido]-1H-indole-2-carboxylic acid hydrate (0.5 g, 83%, containing 2% water by weight). Anhydrous Mot wt (calc) 438.41, MS: 439.35 (MH$^+$), 437.20 (M$^-$). $^1$H NMR (DMSO-d$_6$): δ 3.97 (s, 3H), 7.13 (s, 1H), 7.30-7.75 (complex, 10H), 7.92 (s, 1H), 10.21 (s, 1H).; HPLC retention time 9.29 minutes.

Preferred Alternative C. 1-Methyl-5-[4'-(trifluoromethyl)[1,1'-biphenyl]-2-carboxamido]-1H-indole-2-carboxylic acid potassium salt 2.6 hydrate A solution of potassium hydroxide (54.1 g) in water (600 mL) was added over 15 minutes to a suspension of ethyl 1-methyl-5-[4'-(trifluoromethyl)[1,1'-biphenyl]-2-carboxamido]-1H-indole-2-carboxylate (300 g), from the previous step, in propan-2-ol (4500 mL) at 60° C. and the resulting mixture was heated to reflux for an hour. The solution was seeded with product (1-methyl-5-[4-(trifluoromethyl)[1,1'-biphenyl]-2-carboxamido]-1H-indole-2-carboxylic acid potassium salt) and the mixture granulated at 60-70° C. for two hours. The mixture was slowly cooled to 0-5° C. and the product potassium salt collected by filtration, washing with a chilled 90/10 mixture of propan-2-ol and demineralized water (510 mL total volume). The product solids were dried, yielding 1-methyl-5-[4'-(trifluoromethyl)[1,1'-biphenyl]-2-carboxamido]-1H-indole-2-carboxylic acid potassium salt 2.6 hydrate (287.4 g, 85% correcting for water content of 9.1% by weight). Anhydrous Mol wt of parent acid (calc) 438.41, MS: 439.3 (MH$^+$), 437.3 (M$^-$). $^1$H NMR (DMSO-d$_6$): δ 3.99 (s, 3H), 6.53 (s, 1H), 7.12-7.76 (complex, 11H), 10.05 (broad), HPLC retention time 9.30 minutes. The preferred solid form of the product is characterized by the pXRD (powder X-ray diffraction) pattern shown in FIG. 7.

(e) (S)-N-benzyl-N-methyl-2-phenylglycinamide hydrochloride monohydrate (S)-N-tert-butoxycarbonyl-2-phenylglycine (250 g) and 1-hydroxybenzotriazole hydrate (136.2 g) and N,N'-dicyclohexylcarbodimide (205.1 g) were combined in dichloromethane (3000 mL) at 0-5° C. and the mixture stirred for 15 minutes. A solution of N-methylbenzylamine (128.1 mL) in dichloromethane (835 mL) was added slowly, maintaining 0-5° C. The resulting slurry was allowed to warm to room temperature overnight before being filtered, washing the by-product solids with dichloromethane (500 mL). The combined filtrate was twice washed with saturated aqueous sodium hydrogen carbonate (2×1500 mL), twice washed with 50% saturated aqueous sodium hydrogen carbonate solution (2×1500 mL), once washed with 2.5% aqueous citric acid solution (1500 mL) and once washed with demineralized water (1500 mL), providing a dichloromethane solution of tert-butyl (S)-2-[benzyl(methyl)amino]-2-oxo-1-phenylethylcarbamate. Analysis by chiral HPLC showed that 2% of the wrong enantiomer (tert-butyl (R)-2-[benzyl(methyl)amino]-2-oxo-1-phenylethylcarbamate) to be present at this stage.

The solvent was replaced with propan-2-ol (2400 mL) via distillation at 20-25° C. and the solution cooled to and maintained at 0-5° C. during the addition of concentrated hydrochloric acid (1000 mL). The resulting solution was allowed to warm to room temperature overnight before the excess reagent byproducts and water were removed by co-distillation with additional propan-2-ol (8000 mL), providing a concentrated solution of product at 50-60° C. The product was precipitated by the addition of tertbutyl methyl ether (1875 mL) maintaining 50-60° C. and seeding. The resulting slurry was cooled to 20° C., and the solids were filtered, washed with tert-butyl methyl ether (500 mL) and dried, yielding product (S)-N-benzyl-N-methyl-2-phenylglycinamide hydrochloride monohydrate (190.8 g, 62% corrected for water content of 6.35% by weight). Analysis by chiral CE showed that 0.2% of the wrong enantiomer ((R)-N-benzyl-N-methyl-2-phenylglycinamide hydrochloride monohydrate) to be present at this stage. Anhydrous Mol wt of parent amine (calc) 254.33, MS: 255.4 (MH$^+$). $^1$H NMR (DMSO-d$_6$): major/minor rotomers δ 3.298 (s, 3H), 4.46/4.55 (m=2×dd, 2H), 5.55/5.57

(2×s, 1H), 6.93-7.57 (complex, 10H), 8.70 (s broad, 3H), HPLC retention time 5.87 minutes.

Figure 6:
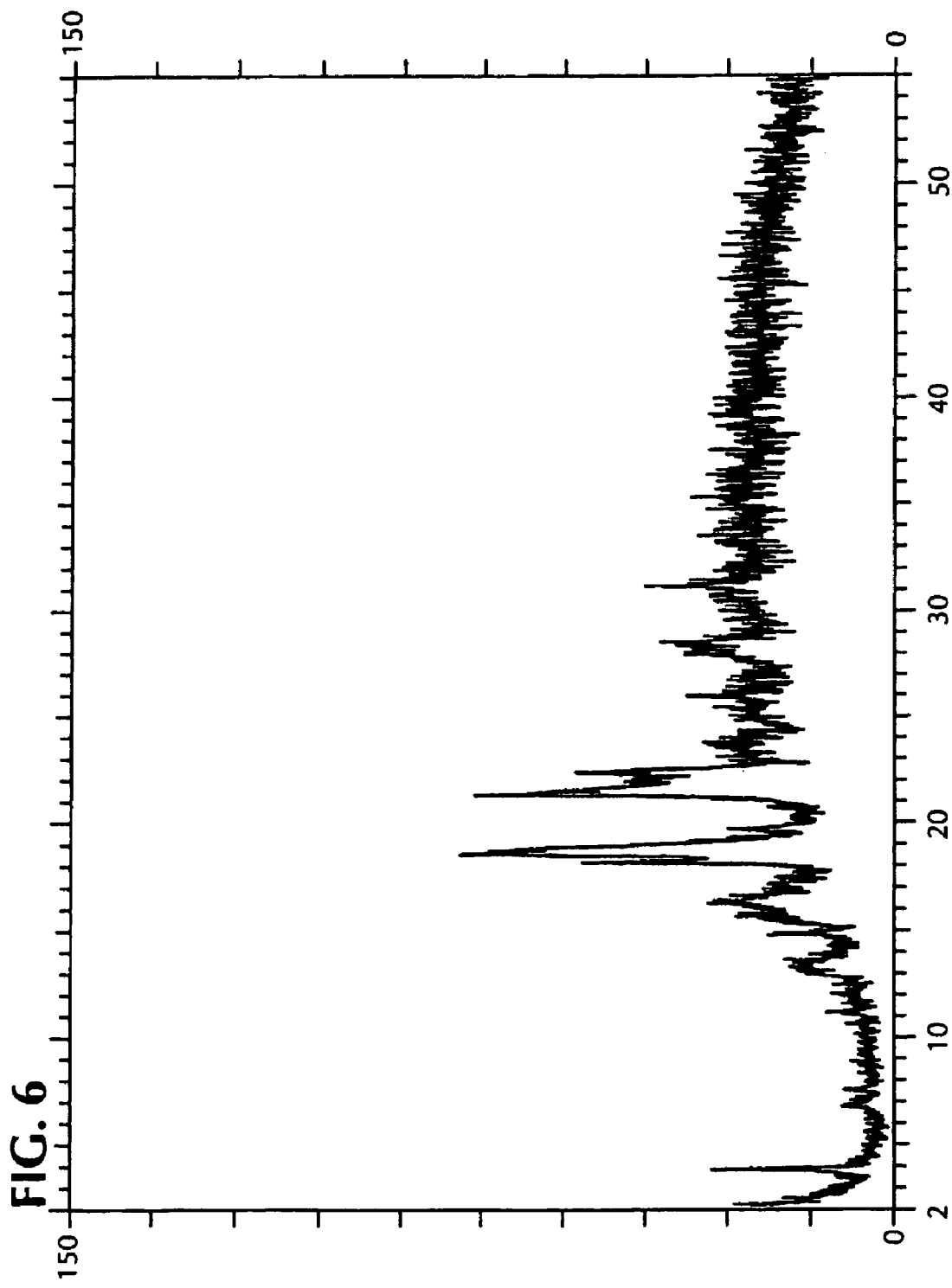
FIG. 6 shows the X-ray powder diffraction pattern of a sample of the intermediate compound 1-Methyl-5-[4'-(trifluoromethyl)[1,1'-biphenyl]-2-carboxamido]-1H-indole-2-carboxylic acid potassium salt 2.6 hydrate, prepared in Example 44 step (d) alternative C. Detailed conditions for the preparation of the sample are provided in Example 44. The pattern was obtained on a Siemens D5000, Cu anode, variable slit, range 2-55, step size: 0.02; ambient temperature.

The preferred solid form of the product is characterized by the XRD (X-ray diffraction) data shown in FIG. 6.

(f) (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide 1-Methyl-5-[4'-(trifluoromethyl)[1,1'-biphenyl]-2-carboxamido]-1H-indole-2-carboxylic acid sodium salt (16.0 g), from step (d) alternative A, methanesulfonic acid (2.24 mL), 1-hydroxybenzotriazole hydrate (5.32 g) and N-[3-(dimethylamino)propyl-N'-ethylcarbodiimide hydrochloride (8.66 g) were combined in dichloromethane (384 mL) at 0-5° C. and the mixture stirred for 1 hour. Triethylamine (4.78 ml mL) was added followed by a slurry of (S)-N-benzyl-N-methyl-2-phenylglycinamide hydrochloride (11.1 g), from step (e), in dichloromethane (48 mL) was added slowly, maintaining D-5° C. The resulting slurry was allowed to warm to room temperature overnight. Further triethylamine (2.4 mL) was added at 0° C. After approximately 2 hours, the mixture was twice washed with saturated aqueous sodium hydrogen carbonate (2×200 mL), once washed with 0.5M aqueous hydrochloric acid solution (200 mL) and once washed with demineralized water (200 mL) adjusting to pH=6 with aqueous sodium hydrogen carbonate solution, providing a dichloromethane solution of (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide.

Using the dichloromethane solution of the title compound, the solvent was replaced with propan-2-ol (32 mL) via distillation, the warm solution was diluted with tertbutyl methyl ether (170 mL), cooled and seeded. The product was collected in three initial crops (77%). These were combined with their mother liquors in dichloromethane (75 mL) to provide a solution. The solvent was again replaced with propan-2-ol (32 mL) via distillation, the warm solution was diluted with tertbutyl methyl ether (160 mL), cooled to room temperature, concentrated to half volume, and granulated overnight. The resulting slurry was filtered and the cake washed with a 1:1 mixture of propan-2-ol and tertbutyl methyl ether and dried in vacuum, yielding product (S)-N-{2-[benzyl(methyl)amino]-2-oxo-1-phenylethyl}1-methyl-5-[4'-(trifluoromethyl)[1,1'-biphenyl]-2-carboxamido]-1H-indole-2-carboxamide in Form A (16.3 g, 69.5%). MS: 675.1 (MH$^+$). $^1$H NMR (DMSO-d): major/minor rotomers δ 2.89/2.78 (s, 3H), 3.94/3.90 (s, 3H), 4.57 (m=2×dd, 2H), 6.07/6.13 (d, 1H, J=7.4/7.4 Hz), 7.11-7.76 (complex, 21H), 7.86 (s, 1H), 8.79/8.84 (d, 1H, J=7.4/7.7 Hz), 10.20 (s, 1H). Mol wt (calc) 674.73; MS 675.2. HPLC retention time 17.948 minutes using the standard conditions cited before Example 1.

Figure 2:
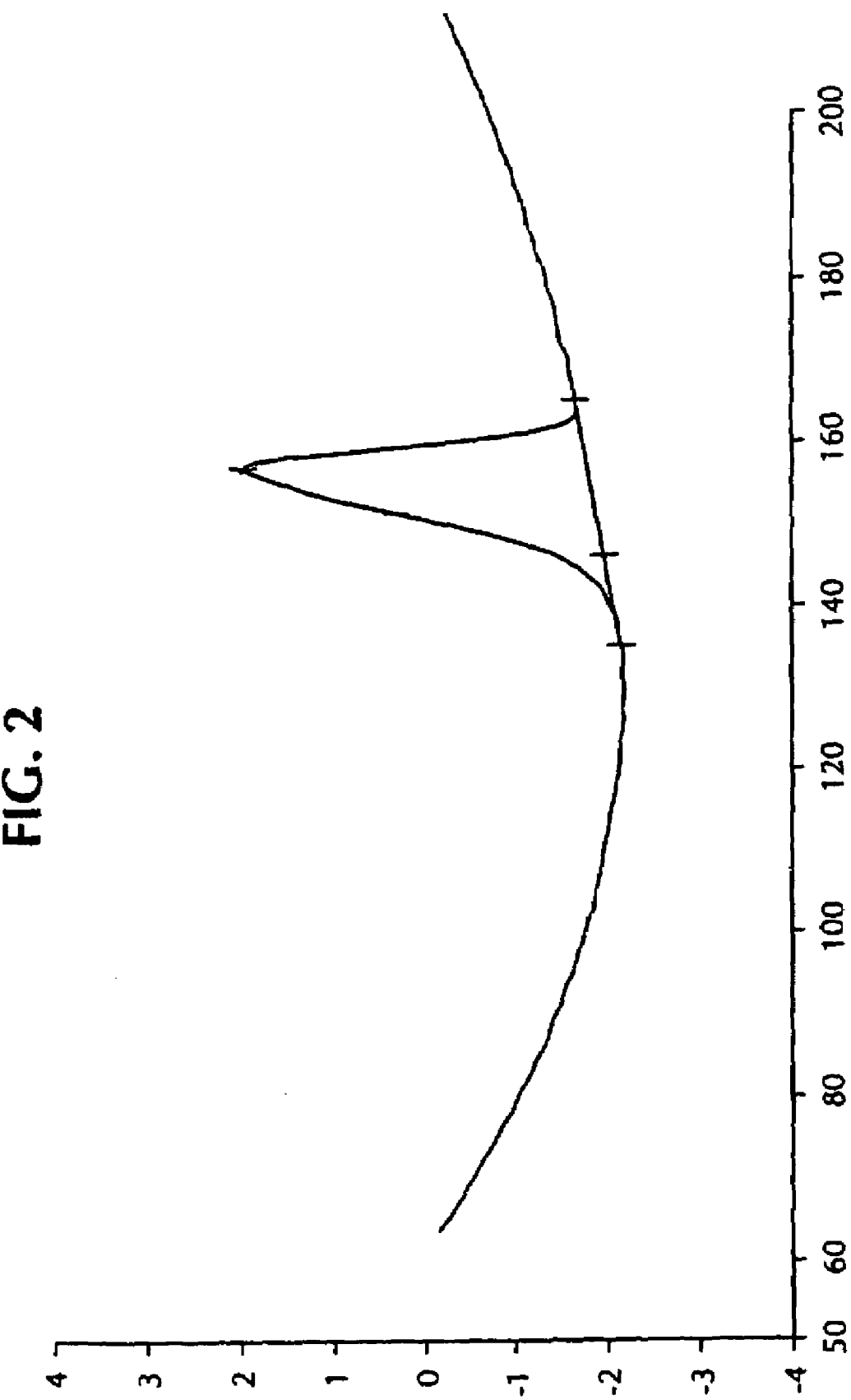
FIG. 2 shows the results of thermal analysis of preferred Form A of the title compound described in Example 44 by differential scanning calorimetry. The peak is 144.068° C.; peak height, 3.8001 mW; peak area 108.368 mJ; Delta H 37.485 J/g; Onset 133.524° C. The analysis was performed under nitrogen gas flow; after holding at 40° C. for 1 minute, heating from 40.00° C. to 200.00° C. at a rate of 20° C./minute. The sample size was 2.891 mg.

The preferred solid form of the product, Form A, is characterized by the pXRD (powder X-ray diffraction) pattern shown in FIG. 1 and DSC (differential scanning calorimetry) trace shown in FIG. 2.

Alternatively and preferably, the title compound is prepared as follows: A solution of methanesulfonic acid (34.0 g) in dichloromethane (85 mL) was added to a mixture of 1-methyl-5-[4'-(trifluoromethyl)[1,1'-biphenyl]-2-carboxamido]-1H-indole-2-carboxylic acid potassium salt hydrate (170 g), from step (d) alternative C, and 1-hydroxybenzotriazole hydrate (54.6 g) in dichloromethane (3400 mL) at 0° C. N-[3-(dimethylamino)propyl-N'-ethylcarbodiimide hydrochloride (88.4 g) in dichloromethane (680 mL) was then added over 30 minutes and the resulting mixture stirred at 0° C. for 1 hour. Triethylamine (53.9 g) in dichloromethane (170 mL) was then added over 10 minutes followed by a solution of (S)-N-benzyl-N-methyl-2-phenylglycinamide hydrochloride hydrate (120.6 g), from step (e), in dichloromethane (680 mL) and the resulting mixture stirred at 0° C. for 30 minutes before allowing to warm to 20° C. for 16 hours. The mixture was twice washed with saturated aqueous sodium hydrogen carbonate (2×2040 mL), once washed with 0.25M aqueous hydrochloric acid solution (2040 mL) and once washed with demineralized water (2040 mL). The resulting product solution was concentrated to 595 mL under reduced pressure and the concentrate combined with an acidic ion-exchange resin (240 g) in propan-2-ol (595 mL). The mixture was stirred for 2 hours before filtering, washing the solids with a 50/50 mixture of propan-2-ol and dichloromethane (170 mL) and concentrating to a volume of 595 mL. The solution was diluted with propan-2-ol (510 mL) and then re-concentrated to a volume of 595 mL before diluting with tert-butyl methyl ether (1700 mL). The resulting solution was cooled to 20° C. and seeded and the mixture stirred for 18 hours before concentrating to a volume of 920 mL under reduced pressure. After further granulation at 20° C. for an additional 48 hours the slurry was filtered and washed with cold propan-2-ol (340 mL). The product solids were dried, yielding the product (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide in Form A (192 g, 80%). HPLC retention time 11.50 minutes using the conditions specific to this example (noted above).

Figure 3:
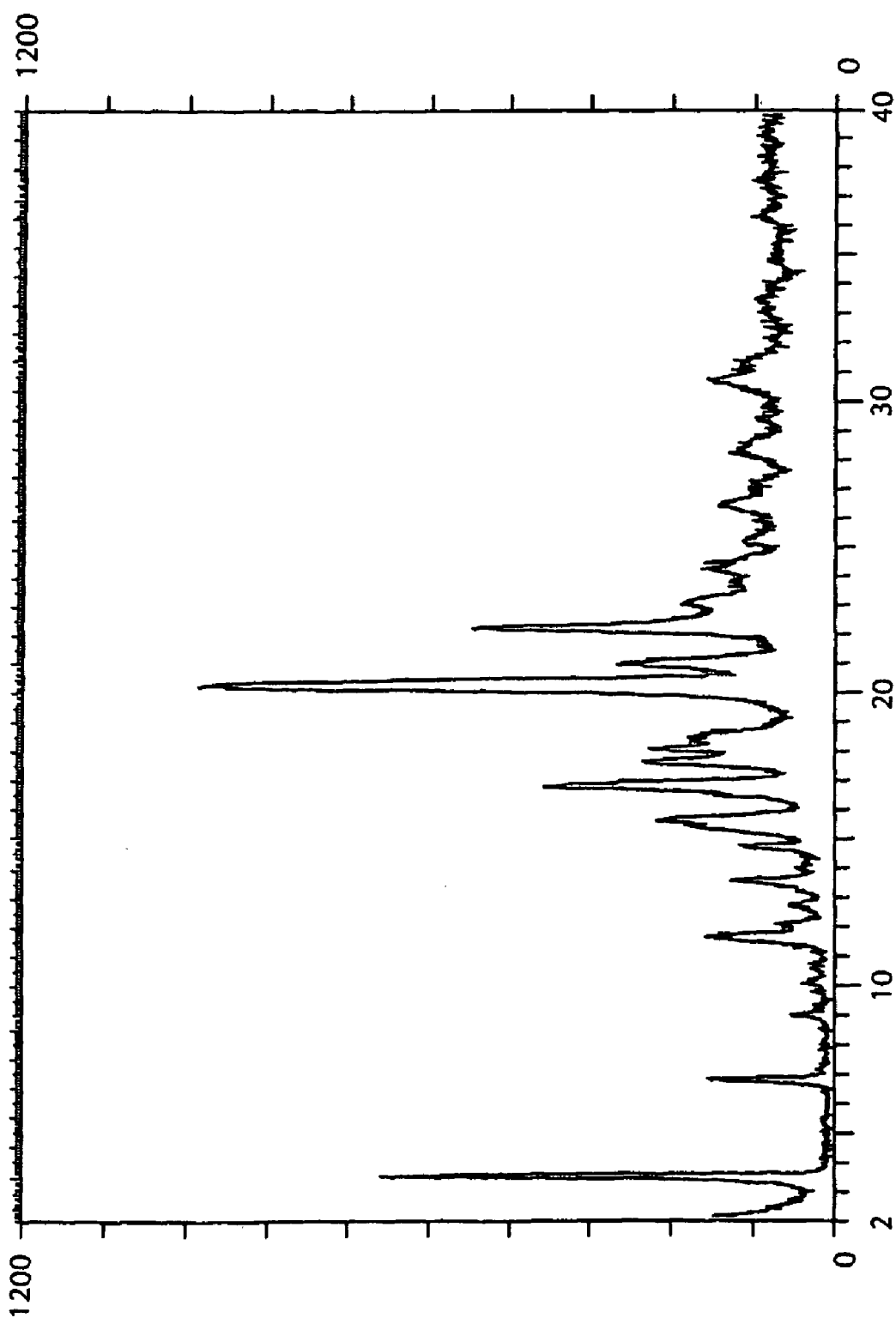
FIG. 3 shows the X-ray powder diffraction pattern of a sample of preferred Form B of the title compound described in Example 44. Detailed conditions for the preparation of the sample are provided in Example 44. The pattern was obtained on a Siemens D5000, Cu anode, variable slit, range 2-55, step size: 0.02; ambient temperature.

Alternative solid Form B of the title compound is prepared as follows: The title compound (150.7 g), prepared by any of the methods described, was dissolved in acetonitrile (350 mL) and filtered. Further title compound (30.8 g) was then added as a seed and the resulting mixture diluted with diisopropyl ether (3300 mL) and granulated at 20-25° C. for 48 hours. The solids were filtered, washed with diisopropyl ether and dried to give the product in Form B (163.5 g, 90%). Form B, is characterized by the pXRD (powder X-ray diffraction) pattern shown in FIG. 3.

Figure 4:
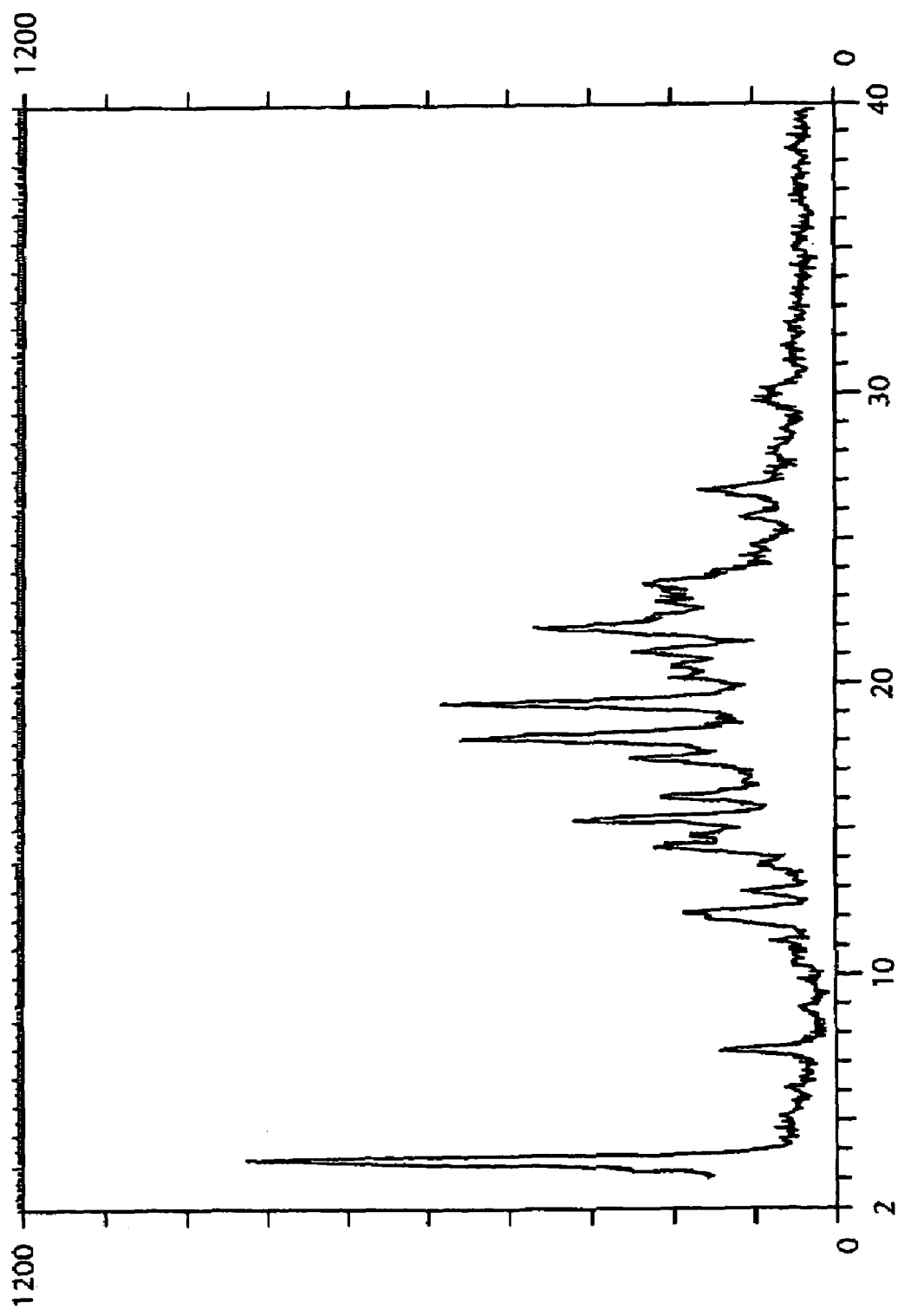
FIG. 4 shows the X-ray powder diffraction pattern of a sample of preferred Form G of the title compound described in Example 44. Detailed conditions for the preparation of the sample are provided in Example 44. The pattern was obtained on a Siemens D5000, Cu anode, variable slit, range 2-55, step size: 0.02; ambient temperature.

Alternative solid Form G of the title compound is prepared as follows: The title compound (13.5 g), prepared by any of the methods described, was dissolved in ethanol (100 mL) at elevated temperature and the resulting solution allowed to cool and granulate at 20-25° C. for 48 hours. Further ethanol (150 mL) was then added and the resulting mixture granulated at 20-25° C. for a further 48 hours. A portion of this mixture was filtered and the solids were washed with ethanol before separating into two portions. One portion of solid was dried at ambient temperature and pressure to give the product in Form G (1.1 g). Form G, is characterized by the pXRD (powder X-ray diffraction) pattern shown in FIG. 4.

Figure 5:
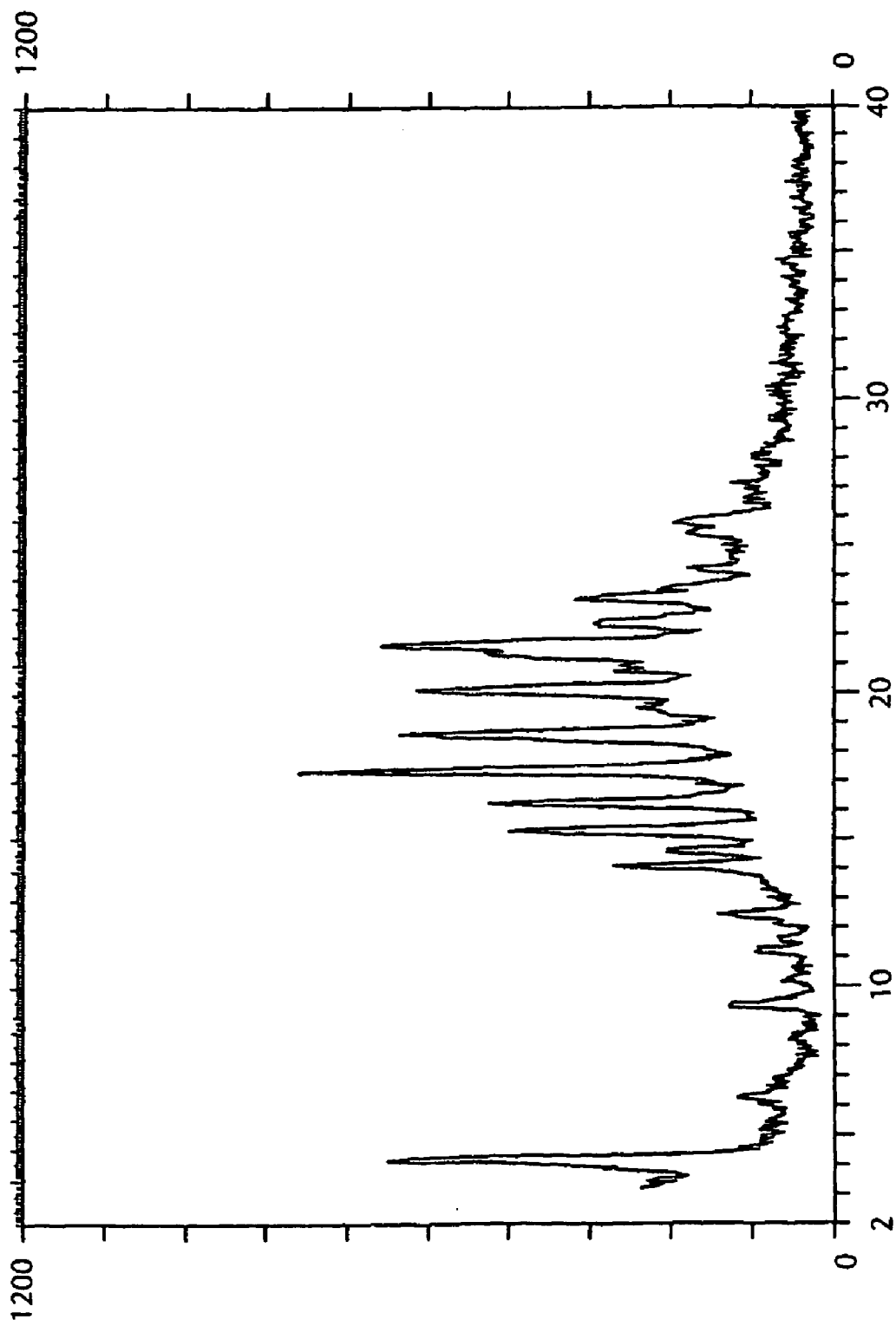
FIG. 5 shows the X-ray powder diffraction pattern of a sample of preferred Form F of the title compound described in Example 44. Detailed conditions for the preparation of the sample are provided in Example 44. The pattern was obtained on a Siemens D5000, Cu anode, variable slit, range 2-55, step size: 0.02; ambient temperature.

Alternative solid Form F of the title compound is prepared as follows: The title compound (13.5 g), prepared by any of the methods described, was dissolved in ethanol (100 mL) at elevated temperature and the resulting solution allowed to cool and granulate at 20-25° C. for 48 hours. Further ethanol (150 mL) was then added and the resulting mixture granulated at 20-25° C. for a further 48 hours. A portion of this mixture was filtered and the solids were washed with ethanol before separating into two portions. One portion of solid was dried under vacuum at 50° C. to give the product in Form F (1.2 g). Form F, is characterized by the pXRD (powder X-ray diffraction) pattern shown in FIG. 5.

Alternative solid Form F of the title compound may also be prepared as follows: The title compound in Form G (1.214 g), prepared by any of the methods described, was dried under vacuum at 50° C. to give the product in Form F (1.195 g). Form F, is characterized by the pXRD (powder X-ray diffraction) pattern shown in FIG. 5.

Example 45

Compounds of formula 1 where $R^3$ is halogen, preferably chloro, were prepared in the following manner:

(a) 1N-methyl-5-nitroindole-2-carboxylic acid ethyl ester

To a solution of 5-nitroindole-2-carboxylic acid ethyl ester (30.45 g, 130 mmol) in DMF (200 mL) was added 60% NaH (6.4 g, 160 mmol) in several portions, and the mixture was stirred under nitrogen at room temperature for 30 minutes. To this was then slowly added methyl iodide (15.56 mL, 250 mmol), and the stirring was continued for 2 hours. The reaction mixture was quenched with 0.5 N HCl solution (400 mL) and extracted with 2:1 EtOAc/benzene solution (600 mL. The organic layer was washed with water (500 mL), brine (500 mL), dried over $MgSO_4$, and then concentrated in vacuo to give 26.7 g of the title compound.

(b) 3-Chloro-1N-methyl-5-nitroindole-2-carboxylic acid ethyl ester

The product of step (a) (24.8 g, 100 mmol) was dissolved in THF (500 mL), followed by the addition of N-chlorosuccinimide (20 g, 150 mmol), and the reaction mixture was stirred at room temperature under nitrogen for 60 hours. The reaction solution was concentrated in vacuo, and the residue was taken into EtOAc (750 mL). The organic layer was washed with 0.5 N NaOH solution (4×750 mL), brine (750 mL), dried ($MgSO_4$), and concentrated in vacuo to afford the crude product which was purified by recrystallization from ethanol to give 13 g of the title compound (c) 3-Chloro-1N-methyl-5-amino-indole-2-carboxylic acid ethyl ester To a refluxing mixture of hydrazine hydrate (10.8 ml, 222 mmol) and Raney Ni (6 g) in MeOH (200 mL) was slowly added the product of step (b) (12.6 g), and the refluxing was continued for 6 hours. After cooling to room temperature, the Raney Ni was removed by filtration through Celite, and the solvent was removed in vacuo to give the crude product. The residue was dissolved in toluene (100 mL), and concentrated in vacuo. The residue was again dissolved in toluene (100 mL), and concentrated in vacuo, the residue was suspended in diethyl ether, and the product was collected by filtration to afford 11.3 g of the title compound.

(d) 3-Chloro-1-methyl-5-[(4'-trifluoromethyl-biphenyl-2-carbonyl)-amino]-1H-indole-2-carboxylic acid ethyl ester 4'-Trifluoromethyl-2-biphenylcarboxylic acid was converted to the corresponding acid chloride by treatment with oxalyl chloride in methylene chloride in the presence of catalytic amount of DMF. To a solution of the acid chloride (10.8 g, 38 mmol) and pyridine (3.27 mL, 40 mmol) in methylene chloride (200 mL) was added the product of step (c) (10.1 g, 40 mmol), and the reaction mixture was stirred at room temperature for 1 hour. The reaction solution was diluted to 600 mL with $CH_2Cl_2$, washed with 0.1 N HCl solution (2×500 mL) and with brine (500 mL), and then dried ($MgSO_4$). The solvent was evaporated in vacuo to give the crude product which was purified by recrystallization from EtOAc/isooctane to afford 13.8 g of the title compound.

(e) 3-Chloro-1-methyl-5-[(4'-trifluoromethyl-biphenyl-2-carbonyl)-amino]-1H-indole-2-carboxylic acid The product of step (d) may be hydrolyzed as follows: the compound (5.51 g) was dissolved in THF (120 mL) and methanol (40 mL). Under stirring conditions was added LiOH (1.32 g) in water (40 mL). The reaction mixture was stirred at room temperature overnight. To the reaction mixture was then added 1 N HCl solution (60 mL), and the aqueous layer was extracted with EtOAc (250 mL). The organic layer was washed with brine (200 mL), and dried ($MgSO_4$). The solvent was evaporated in vacuo to give the crude product which was purified by recrystallization from 1:1 EtOAc/ether to afford 4.4 g of the title compound.

(f) 3-Chloro-1-methyl-5-(methyl-(4'-trifluoromethyl-biphenyl-2-carbonyl)-amino]-1H-indole-2-carboxylic acid As an alternative to step (a), the product of step (d), in which $R^9$ is hydrogen, optionally may be alkylated by processes well known in the art. For example, to prepare a compound in which $R^9$=methyl, the product of step (d) is treated with $Me_2SO_4$ in the presence of KOH, $K_2CO_3$ and $Bu_4NHSO_4$ in a suitable solvent such as toluene, with heating to 70° C. with stirring for about 30 minutes. After cooling to room temperature, the reaction mixture is diluted with 1 N HCl and stirred for 10 min. EtOAc (100 mL) is then added, and the organic layer washed with brine, dried ($MgSO_4$), and solvent removed in vacuo to give the product wherein $R^9$ is methyl, with appropriate purification e.g., by recrystallization from 1:2 EtOAc/isooctane.

The resulting indole ester may then be hydrolysed as in step (e), e.g., as follows: the compound is dissolved in 3:1 THF: methanol, LiOH in water is added under stirring conditions and the reaction mixture is stirred at room temperature overnight. To the reaction mixture is then added 1 N HCl solution, and the aqueous layer s extracted with EtOAc (about 2 volumes). The organic layer is washed with brine, and dried ($MgSO_4$). The solvent is evaporated in vacuo to give the crude product which may be purified by recrystallization from 1:1 EtOAc/ether to afford an indole carboxylic acid of formula AB1.

The products of steps (e) and (f), i.e., compounds of formula AB1, may be amide linked to compounds of formula C by methods which are well known in the art, an example of which is described below in step (g)

(g) 3-Chloro-1-methyl-5-[(4'-trifluoromethyl-biphenyl-2-carbonyl)amino]-1H-indole-2-carboxylic acid [2-(isopropylamino)-2-oxo-1-phenylethyl]amide The product from step (e) (292.5 mg, 0.619 mmol), (S)-N-isopropyl-2-phenylglycinamide hydrochloride salt (182.1 mg, 0.797 mmol), PyBroP (415.8 mg, 0.865 mmol) were suspended in anhydrous $CH_2Cl_2$ (6 ml), followed by the addition of DIEA (0.36 ml, 2.07 mmol). The reaction mixture was stirred at room temperature for 3.5 h. The product was purified by flash chromatography using 30:70 of hexane:EtOAc to afford 345.5 mg of the title compound.

Examples 46-65 were prepared similarly to Example 45 above, and Examples 65b-f were prepared similarly to Example 65a below.

TABLE 5

| Example | R⁴ | R⁵ | R⁶ | R⁷ | R⁹ | R¹³ | Mol wt. (calc) | MS (found) | HPLC (min) |
|---|---|---|---|---|---|---|---|---|---|
| 46 | Methyl | H | Methyl | Benzyl | H | Trifluoromethyl | 709.17 | 709.2 | 20.185 |
| 47 | Methyl | H | H | Propyn-3-yl | H | Trifluoromethyl | 643.07 | 643.2 | 15.244 |
| 48 | Methyl | H | H | Isopropyl | H | Trifluoromethyl | 647.10 | 647.2 | 16.567 |
| 49 | Methyl | H | Methyl | Pyrid-3-yl | H | Trifluoromethyl | 710.16 | 710.2 | 8.513 |
| 50 | Methyl | H | H | Propyl | H | Trifluoromethyl | 647.10 | 647.2 | 16.67 |
| 51 | Methyl | H | Ethyl | Benzyl | H | Trifluoromethyl | 723.20 | 723.2 | 21.392 |
| 52 | Methyl | H | Methyl | 3-chloro-benzyl | H | Trifluoromethyl | 743.61 | 744.2 | 20.578 |
| 53 | Methyl | H | Methyl | Benzyl | Methyl | Trifluoromethyl | 723.20 | 723.2 | 21.202 |
| 54 | Methyl | H | H | Ethyl | Methyl | Trifluoromethyl | 647.10 | 647.2 | 15.615 |
| 55 | Methyl | H | H | Isopropyl | Methyl | Trifluoromethyl | 661.1 | 661.2 | 17.161 |
| 56 | Methyl | H | Methyl | Pyrid-3-yl | Methyl | Trifluoromethyl | 724.18 | 724.2 | 9.154 |
| 57 | H | H | Methyl | Benzyl | H | Trifluoromethyl | 695.14 | 695.2 | 19.131 |
| 58 | Ethyl | H | Methyl | Benzyl | H | Trifluoromethyl | 723.20 | 723.2 | 21.172 |
| 59 | Ethyl | H | H | 4-methoxy-benzyl | H | Trifluoromethyl | 739.20 | 739.2 | 18.345 |
| 60 | Methyl | Methyl | Methyl | Benzyl | H | Trifluoromethyl | 709.22 | 709.2 | 8.966 |
| 61 | Methoxy-methyl | H | Methyl | Benzyl | H | Trifluoromethyl | 739.20 | 739.2 | 19.677 |
| 62 | Methyl | H | H | Propyl | H | H | 579.10 | 579.2 | 14.388 |
| 63 | Methyl | H | H | Isopropyl | H | H | 579.10 | 579.2 | 14.327 |
| 64 | Methyl | H | Methyl | Pyrid-2-yl | H | H | 642.16 | 642.2 | 11.303 |
| 65 | Methyl | H | Methyl | Pyrid-3-yl | H | H | 642.16 | 642.2 | 6.322 |
| 65b | Methyl | H | Methyl | Ethyl | H | Trifluoromethyl | 633.12 | 633.2 | 4.318 |
| 65c | Methyl | H | H | 4-methyl-benzyl | H | Trifluoromethyl | 695.19 | 695.2 | 11.147 |
| 65d | Methyl | H | H | Propyl | H | Trifluoromethyl | 633.12 | 633.2 | 6.923 |
| 65e | Methyl | H | Ethyl | Ethyl | H | Trifluoromethyl | 647.15 | 647.2 | 5.071 |
| 65f | Methyl | H | H | Methyl | H | Trifluoromethyl | 605.06 | 605.2 | 5.433 |

Example 65a

3-Chloro-1-methyl-5-[(4'-trifluoromethyl-biphenyl-2-carbonyl)amino]-1H-indole-2-carboxylic acid [2-(ethylamino)-2-oxo-1-phenylethyl]amide

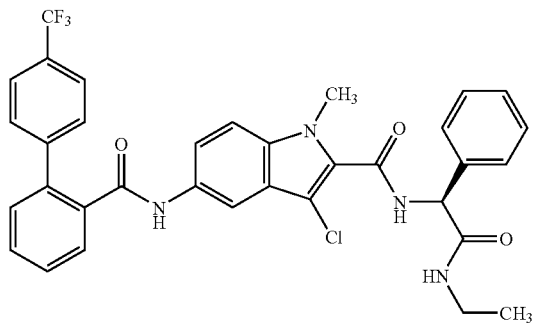

(a) 3-Chloro-1-methyl-5-[(4'-trifluoromethyl-biphenyl-2-carbonyl)amino]-1H-indole-2-carboxylic acid (3.41 g, 6.6 mmol), N,O-dimethyl hydroxylamine hydrochloride salt (0.938 g, 9.4 mmol) PyBroP (4.50 g, 9.4 mmol) were suspended in CH$_2$Cl$_2$ (60 ml), followed by the addition of diisopropylethyl amine, and the resultant reaction mixture was stirred at room temperature for several hours. The reaction solution was concentrated to ~25 ml, and then directly applied to flash chromatography using 30:70 of EtOAc/hexane to give 2.86 g of the title compound.

(b) 4'-Trifluoromethyl-biphenyl-2-carboxylic acid (3-chloro-2-formyl-1-methyl-1H-indol-5-yl)amide To a solution of the product from step (a) (1.56 g, 3.02 mmol) in THF (25 ml) at −78° C. was added DIBAL in THF (1.0 M, 12 ml), and the reaction mixture was stirred at −78° C. for 6 h. The reaction mixture was diluted with NaHSO$_4$ (0.25 M, 86 ml) and EtOAc (115 ml), and the aqueous layer was extracted with EtOAc (2×100 ml). The combined organic layers were dried (MgSO$_4$) and concentrated in vacuo to about 30 ml in volume. The product was purified by flash chromatography using 1:1 EtOAc/hexane to afford 0.706 g of the title compound.

(c) 3-Chloro-1-methyl-5-[(4'-trifluoromethyl-biphenyl-2-carbonyl)-amino]-1H-indole-2-carboxylic acid [2-[(ethylamino)-2-oxo-1-phenylethyl]amide The product from step (b) (407.5 mg, 0.892 mmol), (S)-N-ethyl-2-phenylglycinamide hydrochloride salt (316.3 mg, 1.47 mmol) and acetic acid (10 drops) were suspended in $CH_2Cl_2$ (25 mL), and the reaction mixture was stirred at room temperature for 20 min. $NaB(OAc)_3H$ (2.1 eq) was then added, and the reaction mixture was stirred at 50° C. for 5.5 h. Saturated $NaHCO_3$ (8 mL) and $CHCl_3$ (12 mL) were then added, and the organic layer was washed with water (6 mL), and then concentrated in vacuo. The product was purified by flash chromatography using 30:70 of hexane:EtOAc to afford 441.4 mg of the title compound.

Examples 66-85

Using a compound of formula B1C, substituted biphenyl "A" groups were amide linked to form the compounds shown in Table 6 according to the following method:

A stock solution containing compound B1C (20.4 mg, 0.0478 mmol), EDC (19.6 mg, 0.102 mmol), and DMAP (2.47 mg, 0.020 mmol) in $CH_2Cl_2$ (0.8 ml) was added to a 1.8 mL reaction vial containing the acid (1.2 eq), and the resulting mixture was shaken at room temperature overnight. To the reaction mixture was then added 0.5 ml of N,N-dimethylethylenediamine and the reaction mixture was then shaken for 18 h. The product was purified by silica gel chromatography using $CH_2Cl_2$/EtOAc. The yields ranged from about 70% to about 95%.

Example 86

(S)-5-(2-Butoxy-benzoylamino)-1-methyl-1H-indole-2-carboxylic acid {2-[benzyl(methyl)amino]-2-oxo-1-phenylethyl}-amide (a) 5-(2-Acetoxy-benzoylamino 1-methyl-1H-indole-2-carboxylic acid ethyl ester To a solution of 5-amino-1-methyl-indole-2-carboxylic acid ethyl ester (12.86 g, 58.92 mM) and diisopropylethylamine (20.5 mL, 117.84 mM) in $CH_2Cl_2$ at 0° C. was added a solution of acetyl salicyloyl chloride in $CH_2Cl_2$ over 30 minutes. After the addition was complete the cooling bath was removed and the mixture was allowed to warm to room temperature and stirred at that temperature for 2 hours. The mixture was transferred to a separatory funnel and the solution was washed with 1N HCl (150 mL) and aqueous $NaHCO_3$. The organic fraction was dried over $MgSO_4$ and filtered. The solvent was removed under reduced pressure to provide the title compound.

(b) 5-(2-Hydroxy-benzoylamino)-1-methyl-1H-indole-2-carboxylic acid

The product of step (a) (2.0 g, 5.26 mM) was dissolved in THF (30 mL), methanol (10 mL), and water (10 mL). The mixture was treated with lithium hydroxide (882 mg, 21.04 mM) and the mixture was stirred at room temperature for 3 hours. The mixture was concentrated to 15 mL and the pH was adjusted to about 3.0 with 1 N HCl. The mixture was extracted 3 times with ethyl acetate (25 mL). The ethyl acetate fractions were combined, dried over $MgSO_4$, filtered and concentrated to provide the title compound.

TABLE 6

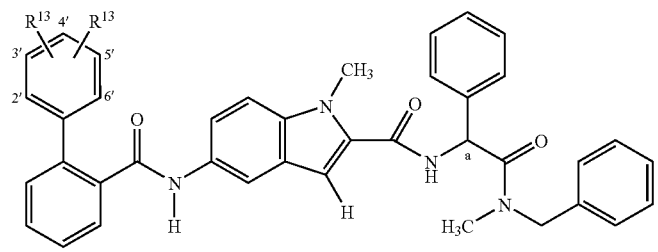

| Example | $R^{13}$ | Other $R^{13}$ (if present) | Mol. wt. |
|---|---|---|---|
| 66 | 3'-fluoro | 5'-fluoro | 642.712 |
| 67 | 2'-fluoro | 4'-fluoro | 642.712 |
| 68 | 3'-trifluoromethyl | 5'-trifluoromethyl | 742.728 |
| 69 | 4'-chloro | — | 641.176 |
| 70 | 3'-methyl | — | 620.758 |
| 71 | 3'-carboxylic acid | — | 650.741 |
| 72 | 3'-chloro | 4'-fluoro | 659.166 |
| 73 | 4'-methoxy | — | 652.822 |
| 74 | 3'-amino | — | 621.746 |
| 75 | 3'-methoxy | — | 636.757 |
| 76 | 3'-carboxymethyl | — | 648.768 |
| 77 | 3'carbamoylmethyl | — | 663.783 |
| 78 | 4'-ethenyl | — | 632.769 |
| 79 | 2'-methoxy | 4'-methoxy | 666.7841 |
| 80 | 4'-hydroxymethyl | — | 636.757 |
| 81 | 2'-methoxy | 5'-chloro | 671.202 |
| 82 | 4'-cyano | — | 631.741 |
| 83 | 4-tert-butyl | — | 662.839 |
| 84 | 3'-methoxy | 4'-methoxy | 666.7841 |
| 85 | 3'-fluoro | 4'-fluoro | 642.712 |

(c) (S)-5-(2-Hydroxy-benzoylamino)-1-methyl-1H-indole-2-carboxylic acid {2-[benzyl(methyl)amino]-2-oxo-1-phenylethyl}amide The product of step (b) (1.36 g, 4.38 mM), PyBrOP (2.45 g, 5.26 mM), and (S)-N-benzyl-N-methyl-2-phenylglycinamide (1.91 g, 6.57 mM) were placed in a 50 mL round bottom flask. DMF (20 mL) was added and the mixture was cooled to 0° C. and treated with diisopropyl ethylamine (3 mL, 17.52 mM). After the addition was complete the cooling bath was removed and the reaction mixture was stirred at room temperature for 16 h. The mixture was diluted with ethyl acetate (120 mL) and the mixture was washed with 1 N HCl (20 mL), water (20 mL) and brine (20 mL). The ethyl acetate was dried with MgSO$_4$, filtered and concentrated. The residue was purified by flash column chromatography on silica gel eluting with 5% diethyl ether in CH$_2$Cl$_2$.

(d) (S)-5-(2-Butoxy-benzoylamino)-1-methyl-1H-indole-2-carboxylic acid {2-[benzyl(methyl)amino]-2-oxo-1-phenylethyl}-amide To a solution of the product of step (c) (120 mg, 0.22 mM), triphenylphosphine (68 mg, 0.26 mM), and an alcohol (0.29 mM) in THF (2 mL) at 0° C. was added DEAD (41 uL, 0.26 mM). The cooling bath was removed and the mixture was stirred at room temperature for 16 hours. The mixture was concentrated to approximately 200 uL and applied to a prep TLC plate (silica gel 60 F254, 1.0 mm, 20 cm×20 cm). The plate was eluted with 5% diethyl ether in CH$_2$Cl$_2$. The band corresponding to product was scraped off the plate. The product was washed from the silica gel with ethyl acetate. The ethyl acetate was concentrated to provide the title product. Mol wt. (calc), 602.74; MS, 603; HPLC, 19.7 minutes.

Examples 87-98 shown in Table 7 were prepared similarly to Example 86.

Example 99

5-[(4'-Trifluoromethyl-biphenyl-2-carbonyl)-amino]-benzofuran-2-carboxylic acid [2-oxo-1-phenyl-2-(propylamino)ethyl]amide

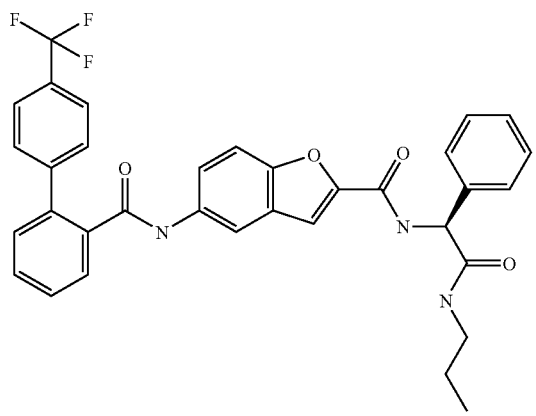

(a) 5-nitrobenzofuran-2-carboxylic acid methyl ester

5-Nitrobenzofuran-2-carboxylic acid (10 g) was dissolved in methanol (200 mL) and chloroform (100 mL), and the mixture was cooled to 0° C. Under stirring conditions was bubbled HCl gas until the solution was saturated. The reaction mixture was stirred at room temperature overnight, and white solid was formed. The precipitate was collected by filtration to afford 9.5 g of the title compound.

(b) 5-aminobenzofuran-2-carboxylic acid methyl ester

The product from step (a) (6.9 g) was dissolved in THF (200 mL), followed by the addition of 10% Pd/C (1 g), and the

TABLE 7

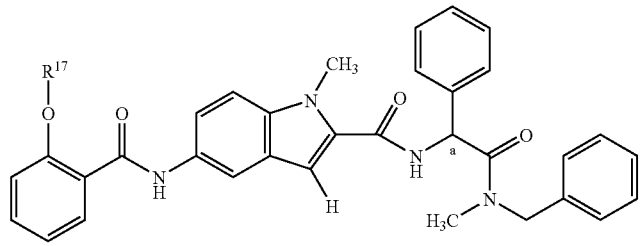

| Example | R$^{17}$ | Mol wt (calc) | MS | HPLC (min) |
|---|---|---|---|---|
| 87 | 2-propyl | 588.71 | 589 | 18.0 |
| 88 | 4-triflouromethylbutyl | 656.71 | 657 | 18.0 |
| 89 | 2-methylpropyl | 602.74 | 603 | 19.7 |
| 90 | 2-methylbutyl | 616.77 | 617 | 21.1 |
| 91 | 2-ethylbutyl | 630.79 | 631 | 22.3 |
| 92 | Allyl | 586.7 | 587 | 17.1 |
| 93 | Cyclopentyl | 614.75 | 615 | 20.0 |
| 94 | Methylcyclohexyl | 642.8 | 643 | 22.7 |
| 95 | Methylcyclopropyl | 600.72 | 601 | 18.5 |
| 96 | 2-phenoxyethyl | 666.78 | 667 | 18.8 |
| 97 | 2-ethoxyethyl | 618.74 | 619 | 16.7 |
| 98 | H | 546.63 | 547 | 15.3 | resulting reaction mixture was hydrogenated under 50 psi of hydrogen for 2 hours. The catalyst was removed by filtration through celite, and the solvent was removed in vacuo to provide 5.9 g of the title compound.

(c) 5-[(4'-Trifluoromethyl-biphenyl-2-carbonyl)-amino]-benzofuran-2-carboxylic acid methyl ester 4'-Trifluoromethyl-2-biphenylcarboxylic acid (9.14 g) was dissolved in $CH_2Cl_2$, followed by the addition of oxalyl chloride (4.49 mL). Under stirring conditions was added DMF (0.5 mL), and the stirring was continued for 1 hour. The solvent and excess oxalyl chloride were removed in vacuo, and the residue was dissolved in $CH_2Cl_2$, followed by the addition of product from step (b) (5.8 g) and pyridine (7.36 mL). The reaction solution was stirred at room temperature overnight. The reaction mixture was concentrated in vacuo, and the residue was dissolved in EtOAc (500 mL), washed with saturated $NaHCO_3$ solution (2×50 mL), water (50 mL), 1N HCl solution (2×50 mL), and brine (50 mL). After drying over $MgSO_4$, the solvent was removed in vacuo to give the crude product which was purified by recrystallization from EtOAc/hexane to afford 8.4 g of the title compound.

(d) 5-[(4'-Trifluoromethyl-biphenyl-2-carbonyl)-amino]-benzofuran-2-carboxylic acid The product from step (c) (8.1 g) was dissolved in THF (100 mL) and methanol (100 mL). Under stirring conditions was added LiOH (2 g) in water (100 mL). The reaction mixture was stirred at room temperature for 30 minutes. The reaction solution was then concentrated in vacuo, acidified by adding 1 N HCl solution. The product was extracted with ether (2×300 mL), and combined organic layers were washed with brine (2×50 mL) and then dried over $MgSO_4$. The organic layer was then concentrated in vacuo to give the crude product which was purified by recrystallization from ether/hexane to give 7.1 g of the title compound.

(e) 5[(4'-Trifluoromethyl-biphenyl-2-carbonyl)-amino]-benzofuran-2-carboxylic acid [2-oxo-1-phenyl-2-(propylamino)ethyl]amide The product from step (d) (100 mg, 0.235 mmol), (S)-N-propyl-2-phenylglycinamide hydrochloride salt (1 eq.) and PyBrop (1.1 eq.) were dissolved in $CH_2Cl_2$ (2 mL), followed by the addition of diisopropylethylamine (3 eq.), and the reaction mixture was stirred at room temperature between 2 hours. The solvent was then evaporated, and the product was purified by prep-TLC using 2:1 EtOAc/hexane as eluting solvent, and the yield was 79 mg.

Examples 100-112 were prepared similarly to Example 99. In Examples 102, 103 and 108, $R^6$ and $R^7$ together with the nitrogen atom to which they are attached form the listed heterocyclyl group.

TABLE 8

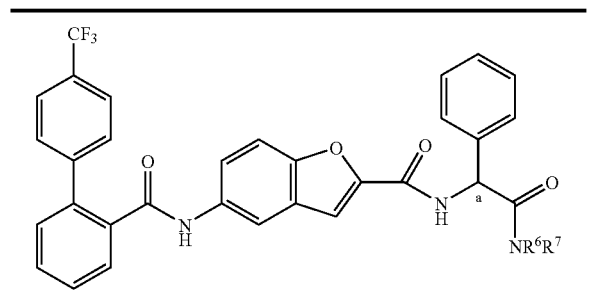

| Example | $R^6$ | $R^7$ | Mol wt (calc) | MS (found) | HPLC (min) |
|---|---|---|---|---|---|
| 100 | H | Cyclopropylmethyl | 611.626 | 612.2 | 15.311 |
| 101 | H | Cyclopropyl | 597.599 | 598.2 | 13.539 |
| 102 | | Piperidin-1yl | 625.653 | 626.2 | 17.696 |

TABLE 8-continued

| Example | $R^6$ | $R^7$ | Mol wt (calc) | MS (found) | HPLC (min) |
|---|---|---|---|---|---|
| 103 | | Morpholin-4-yl | 627.626 | 628.2 | 13.755 |
| 104 | H | Cyclopentyl | 625.653 | 626.2 | 16.677 |
| 105 | H | 3-fluoro-benzyl | 665.65 | 666.2 | 16.705 |
| 106 | H | 2-methyl-but-1-yl | 627.6689 | 628.2 | 17.825 |
| 107 | Methyl | Methyl | 585.588 | 586.2 | 14.26 |
| 108 | | Azetidinyl | 597.599 | 598.2 | 13.51 |
| 109 | H | 4-methoxy-benzyl | 677.686 | 678.2 | 16.075 |
| 110 | H | 3,4-difluoro-benzyl | 683.6409 | 684.2 | 16.955 |
| 111 | H | 2,3-difluoro-benzyl | 683.6409 | 684.2 | 16.961 |
| 112 | H | 2-fluoro-4-trifloromethyl-benzyl | 733.6489 | 733.2 | 18.899 |

Table 9 below provides Examples of additional compounds of the invention, prepared according to the methods described above, in particular, as described for Examples 66-85.

TABLE 9

| Example | $R^1$ | Mol. Wt. (calc) | MS (found) | HPLC (min) |
|---|---|---|---|---|
| 113 | Isopropylmethyl | 524.668 | 525.2 | 14.958 |
| 114 | 2-methoxy-phenyl | 560.658 | 561.2 | 15.07 |
| 115 | 2-methyl-5-chloro-phenyl | 579.104 | 579.2 | 16.683 |
| 116 | 1-hydroxy-cycloprop-1-yl | 552.679 | 553.2 | 13.013 |
| 117 | 2-methyl-4-chloro-phenyl | 579.104 | 579.2 | 16.651 |
| 118 | (Norborn-2-yl)-methyl | 562.718 | 563.2 | 17.288 |
| 119 | Cyclobutyl | 508.625 | 509.2 | 11.734 |
| 120 | phenoxy-ethyl-methyl | 588.712 | 589.2 | 17.118 |
| 121 | 5-bromo-fur-2-yl | 599.489 | 600.2 | 14.651 |
| 122 | 1-phenyl-cyclopent-1-yl | 598.751 | 599.2 | 18.913 |
| 123 | Naphth-1-yl | 580.692 | 581.2 | 15.995 |
| 124 | 3-chloro-thien-2-yl | 571.102 | 571.2 | 15.847 |
| 125 | Perfluoroethyl | 572.539 | 573.2 | 16.771 |
| 126 | 2-(pyrrol-1-yl)-phenyl | 595.707 | 596.2 | 15.497 |
| 127 | Isoquinolin-1-yl | 581.68 | 582.2 | 16.432 |

Pharmaceutical Compositions

Oral solid forms for compounds of the invention, examples of which have been provided above, are preferably tablets, powders or granules which typically contain just the active agent(s) or preferably in combination with adjuvants/excipients to enhance the processing characteristics of the active.

For tablets, the active agent is typically less than 50% (by weight) of the formulation and preferably less than 10%, for example 2.5% by weight. The predominant portion of the formulation comprises fillers, diluents, disintegrants, lubricants and optionally, flavors. The composition of these excipients is well known in the art. According to this invention, the preferred fillers/diluents comprise admixtures of two or more of the following components: avicel, mannitol, lactose (all types), starch, and di-calcium phosphate. The filler/diluent admixtures typically comprises less than 98% of the formulation and preferably less than 95%, for example 93.5%. The preferred disintegrants include Ac-di-sol, Explotab™, starch and sodium lauryl sulphate (SLS)— also known as wetting agent. When present these agents usually comprise less than 10% of the formulation and preferably less than 5%, for example 3%. The preferred lubricant is magnesium stearate. When present this agent usually comprises less than 5% of the formulation and preferably less than 3%, for example 1%. When present these agents comprise less than 60% of the formulation, preferably less than 40%, for example 10-20%. More detailed examples of tablet formulations for the compounds of the invention are shown in Table 10.

The examples shown in Table 10 can be manufactured by standard tabletting processes, for example, direct compression or a wet, dry or melt granulation, melt congealing process and extrusion. The tablet cores may be mono or multilayer(s) and can be coated with appropriate overcoats known in the art.

TABLE 10

Examples of tablet formulations for compounds of formula 1, 2.5% for all formulations below.

| Fillers/Diluents | Disintegrant/ Wetting Agent | Flavors | Lubricant |
|---|---|---|---|
| Avicel/Mannitol 1:2 (93.5%) | Ac-Di-Sol 3% | — | Magnesium Stearate 1% |
| Mannitol/Dcp 2:1 (93.5%) | Ac-Di-Sol 3% | — | Magnesium Stearate 1% |
| Avicel/Dcp 2:1 (93.5%) | Ac-Di-Sol 3% | — | Magnesium Stearate 1% |
| Avicel/ Fast Flo Lactose 1:2 (93.5%) | Ac-Di-Sol 3% | — | Magnesium Stearate 1% |
| Avicel/Mannitol 1:2 (73.5%) | Ac-Di-Sol 3% | Brewers Yeast 20% | Magnesium Stearate 1% |
| Mannitol/Dcp 2:1 (73.5%) | Ac-Di-Sol 3% | Brewers Yeast 20% | Magnesium Stearate 1% |
| Avicel/Mannitol 1:2 (92.5%) | Ac-Di-Sol 3% + Sls 1% | — | Magnesium Stearate 1% |
| Avicel/Mannitol 1:2 (72.5%) | Ac-Di-Sol 3% + Sls 1% | Brewers Yeast 20% | Magnesium Stearate 1% |
| Avicel:Mannitol 1:2 (92.5%) | Explotab 4% | — | Magnesium Stearate 1% |
| Avicel/Mannitol 1:2 (93.5%) | Ac-Di-Sol 3% | — | Sodium Stearyl Fumarate 1% |
| Avicel/Dcp 2:1 (62.5) | Ac-Di-Sol 3% Sls = 1% | Yeast Extract 10% Brewers Yeast 20% | Magnesium Stearate 1% |

Oral liquid forms of the compounds of the invention are preferably solutions, wherein the active compound is fully dissolved. Examples of solvents include all pharmaceutically precedented solvents suitable for oral administration and preferably those in which the compounds of the invention show good solubility i.e., polyethylene glycol, polypropylene glycol, edible oils and glyceryl- and glyceride-based systems. Glyceryl- and glyceride-based systems may preferably include the following agents (and similar chemicals thereof), for example: Captex 355 EP, Crodamol GTC/C, or Labrafac CC, triacetin, Capmul CMC, Migyols (812, 829, 840), Labrafil M1944CS, Peceol and Maisine 35-1. The exact composition of these agents and commercial sources are shown in Table 11. These solvents usually make up the predominant portion of the formulation i.e., greater than 50% and preferably greater than 80%, for example 95% and more preferably greater than 99%. Adjuvants and additives may also be included with the solvents principally as taste-mask agents, palatability and flavoring agents, antioxidants, stabilizers, texture and viscosity modifiers, and solubilizers.

TABLE 11

Trademark, chemical composition and commercial source for some glyceryl and glyceride-based systems

| Trademark | Chemical composition | Commercial Source |
|---|---|---|
| Triacetin | Glyceryl triacetate | Abitec |
| Capmul CMC | Glyceryl caprylate/caprate | Abitec |
| Miglyol 812 | Trigylceride caprate/succinate | Condea |
| Miglyol 829 | Trigylceride aprylate/caprate/succinate | Condea |
| Miglyol 840 | Propylene glycol dicaprylate/dicaprate | Condea |
| Labrafil M1944CS | Oleoyl macrogol-6-glycerides | Gattefosse |
| Maisine 35-1 | Glyceryl monolinoate | Gattefosse |
| Peceol | Glyceryl monooleate | Gattefosse |
| Captex 355 EP | Medium-chain triglyceride | Abitec |
| Crodamol GTC/C | Medium-chain triglyceride | Croda |
| Labrafac CC | Medium-chain triglyceride | Gattefosse |

A preferred oral solution for active compounds of the invention contains up to 1% by weight of active ingredient dissolved in medium-chain triglyceride oils Pharm. Eur. or similar solvents (see table 11).

A more preferred solution contains active compound (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide, of the invention see Example 44, at a concentration up to 0.6 mg per mL in a medium-chain triglyceride oil Pharm. Eur.

A particulary preferred solution contains active compound (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide, of the invention see Example 44, at a concentration up to 0.6 mg per mL in Captex 355 EP, Crodamol GTC/C, or Labrafac CC.

An even more preferred solution contains active compound (S)-N-(2-[benzyl(methyl)amino]-2-oxo-1-phenylethyl)-1-methyl-5-[4'-(trifluoromethyl)[1,1'-biphenyl]-2-carboxamido]-1H-indole-2-carboxamide, of the invention see Example 44, at a concentration of 0.5 mg of per mL in Captex 355 EP, or Crodamol GTC/C.

The preferred solutions above may be prepared in a process involving combining the components with mechanical or ultrasonic agitation at a temperature, in such a fashion that is advantageous to the rate of dissolution.

A more preferable process involves combination of the components with mechanical agitation at a temperature up to 70° C., followed by filtration to ensure solution clarity.

A particularly preferable process involves addition of the active ingredient (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide, of the invention see Example 44, with mechanical agitation, to the Captex 355 EP, Crodamol GTC/C, or Labrafac CC that has been pre-heated to a temperature up to 70° C., followed by cooling and filtration to ensure solution clarity.

An even more preferable process involves addition of the active ingredient (S)-N-{2-[benzyl(methyl)amino]-2-oxo-1-phenylethyl}-1-methyl-5-14'-(trifluoromethyl)[1,1'-biphenyl]-2-carboxamido]-1H-indole-2-carboxamide, of the invention see Example 44, with mechanical agitation, to the Captex 355 EP, Crodamol GTC/C, that has been pre-heated to a temperature 50° C.-70° C. followed by cooling and filtration to ensure solution clarity.

The invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and following examples. Such modifications are intended to fall within the scope of the appended claims.

All references cited herein are incorporated by reference in their entireties for all purposes.

What is claimed is:

1. A method of reversing, alleviating or inhibiting the progress of obesity in an animal in need of treatment thereof, which comprises administering to the animal a therapeutically effective amount of (S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide or a pharmaceutically acceptable salt thereof.

2. The method of claim 1 which comprises administering to the animal a therapeutically effective amount of (S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide.

\* \* \* \* \*